(12) United States Patent
Niwa et al.

(10) Patent No.: US 9,556,279 B2
(45) Date of Patent: Jan. 31, 2017

(54) ANTIBODY VARIANTS COMPOSITION

(75) Inventors: Rinpei Niwa, Tokyo (JP); Mami Tsuchiya, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 907 days.

(21) Appl. No.: 13/038,576

(22) Filed: Mar. 2, 2011

(65) Prior Publication Data
US 2012/0010387 A1 Jan. 12, 2012

Related U.S. Application Data

(60) Provisional application No. 61/309,631, filed on Mar. 2, 2010.

(51) Int. Cl.
*C07K 16/00* (2006.01)
*C07K 16/28* (2006.01)

(52) U.S. Cl.
CPC ....... *C07K 16/2887* (2013.01); *C07K 2317/41* (2013.01); *C07K 2317/522* (2013.01); *C07K 2317/53* (2013.01)

(58) Field of Classification Search
None
See application file for complete search history.

(56) References Cited

U.S. PATENT DOCUMENTS

| | | | |
|---|---|---|---|
| 2004/0136986 A1* | 7/2004 | Raju | 424/144.1 |
| 2007/0148165 A1 | 6/2007 | Shitara et al. | |
| 2008/0138335 A1 | 6/2008 | Takahashi et al. | |
| 2010/0104564 A1* | 4/2010 | Hansen et al. | 424/133.1 |

FOREIGN PATENT DOCUMENTS

| | | |
|---|---|---|
| EP | 1921090 A1 | 5/2008 |
| WO | 2004/063351 A2 | 7/2004 |
| WO | 2005/070963 A1 | 8/2005 |
| WO | 2005/115452 A2 | 12/2005 |
| WO | 2006/019447 A1 | 2/2006 |
| WO | 2006/075668 A1 | 7/2006 |
| WO | 2006/105062 A2 | 10/2006 |
| WO | 2007/011041 A1 | 1/2007 |

OTHER PUBLICATIONS

International Searching Authority, International Search Report issued May 17, 2011 in counterpart International Application No. PCT/JP2011/054549.
European Patent Office, Communication dated Oct. 17, 2013 issued in corresponding European Application No. 11750612.1.

* cited by examiner

*Primary Examiner* — Bradley Duffy
(74) *Attorney, Agent, or Firm* — Sughrue Mion, PLLC

(57) ABSTRACT

Among N-glycoside-linked sugar chains which are bound to the Fc region of an antibody, sugar chains which are bound to Asn at position 297 relates to the activity and stability of the antibody in blood, but there is a possibility that extra sugar chains bound to the amino acid residues at positions other than 297 have influences upon the antibody constant region-mediated activity and a possibility of causing a problem of uniformity as a therapeutic antibody preparation. Accordingly, among N-glycoside-linked sugar chains which bind to the Fc region of the antibody, a method for controlling extra sugar chains which are bound to Asn residues at positions other than position 297 according to the EU index is required. The present invention provides an antibody variant composition, comprising amino acid residues of an Asn-X-Ser/Thr (X represents an amino acid residue other than Pro) sequence at positions other than positions 297 to 299 according to the EU index in an Fc region of a human IgG antibody, in which at least one amino acid substitution selected from an amino acid substitution of Asn to other amino acid residue, an amino acid substitution of X to Pro and an amino acid substitution of Ser/Thr to other amino acid residue is carried out, and a fragment of the antibody variant composition.

4 Claims, 8 Drawing Sheets

Fig. 1
(a)
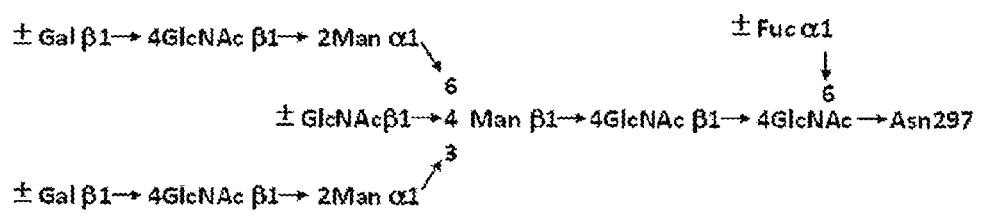
(b)
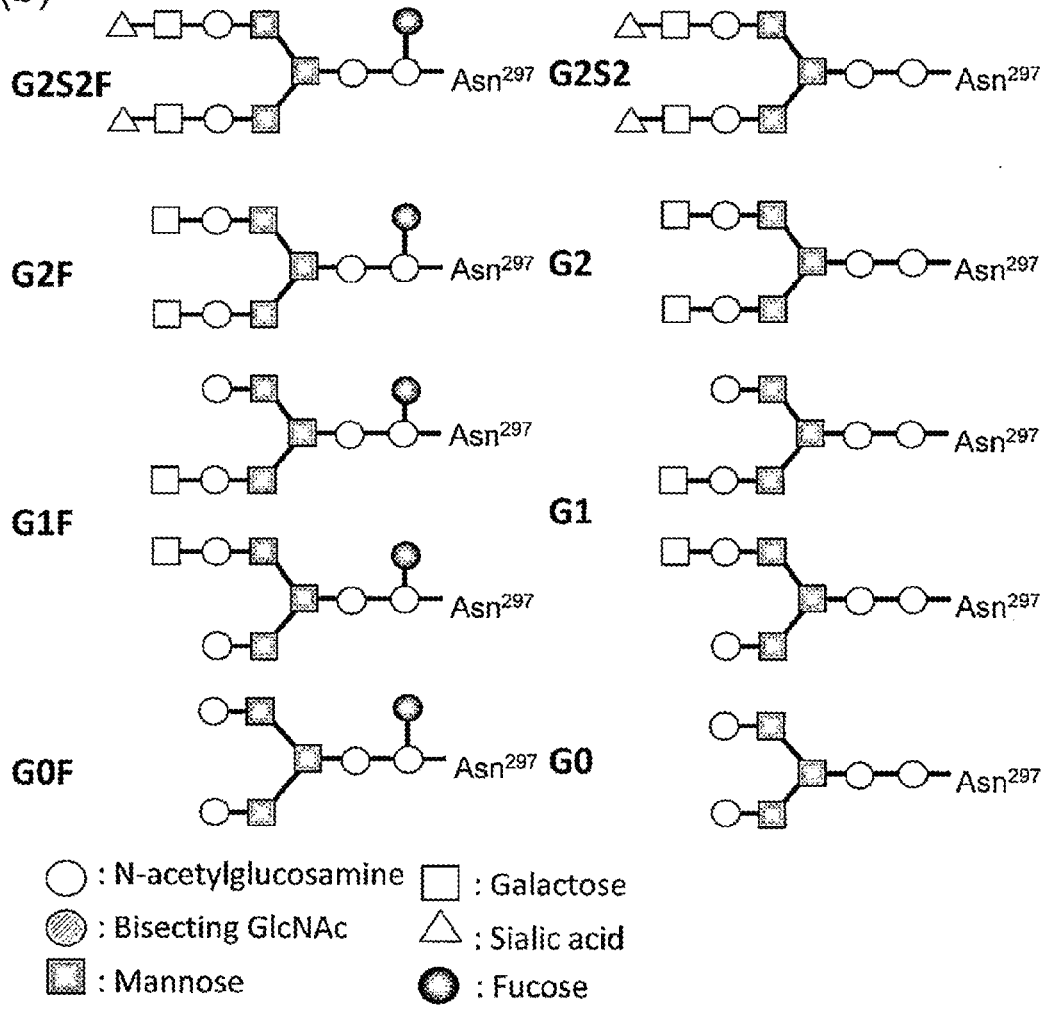

Fig. 2
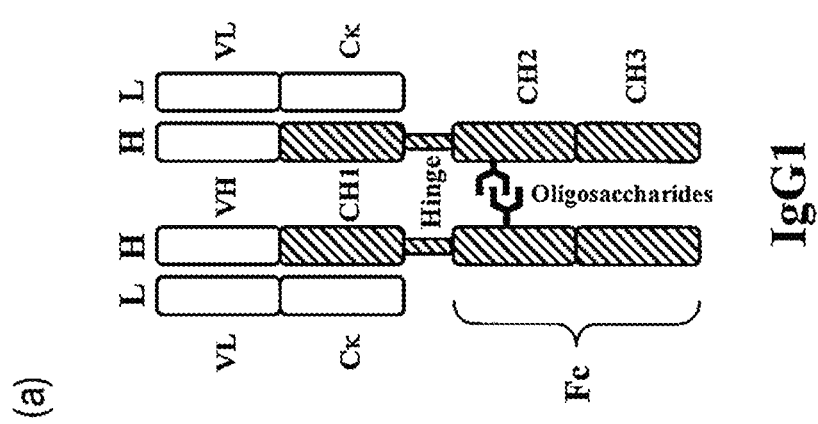
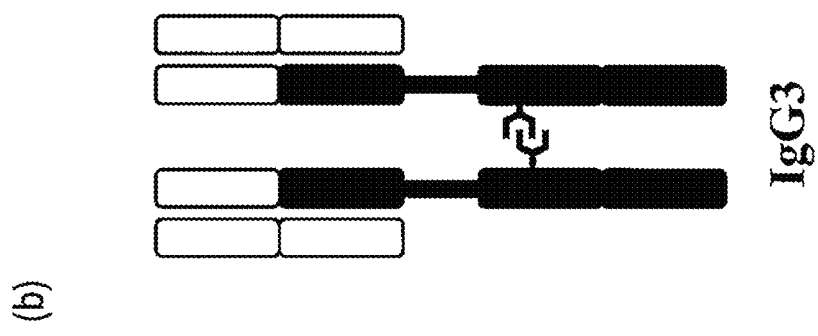
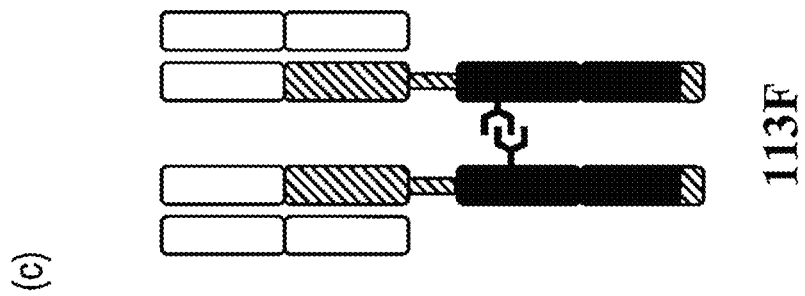

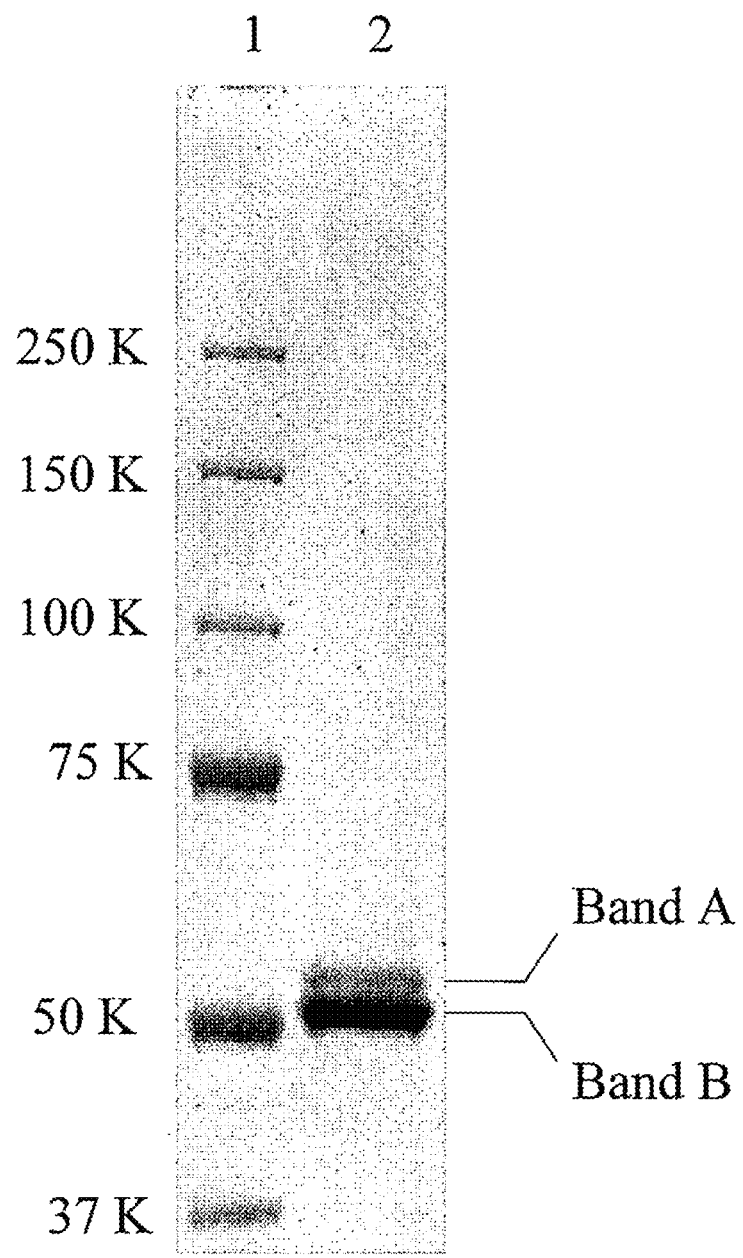

Fig. 4

```
          CH1
         ┌─────►
         120       130       140       150       160       170
IgG1  ASTKGPSVFPLAPSSKSTSGGTAALGCLVKDYFPEPVTVSWNSGALTSGVHTFPAVLQSS
IgG3  ASTKGPSVFPLAPCSRSTSGGTAALGCLVKDYFPEPVTVSWNSGALTSGVHTFPAVLQSS
113F  ASTKGPSVFPLAPSSKSTSGGTAALGCLVKDYFPEPVTVSWNSGALTSGVHTFPAVLQSS

Hinge
                                                  ┌─────►
         180       190       200       210        220
IgG1  GLYSLSSVVTVPSSSLGTQTYICNVNHKPSNTKVDKKVEPKSCDKTHT------------
IgG3  GLYSLSSVVTVPSSSLGTQTYTCNVNHKPSNTKVDKRVELKTPLGDTTHTCPRCPEPKSC
113F  GLYSLSSVVTVPSSSLGTQTYICNVNHKPSNTKVDKKVEPKSCDKTHT------------
                                                             CH2
                                                            ┌─────►
                                                            230       240       250
IgG1  ------------------------------CPPCPAPELLGGPSVFLFPPKPKDT
IgG3  DTPPPCPRCPEPKSCDTPPPCPRCPEPKSCDTPPPCPRCPAPELLGGPSVFLFPPKPKDT
113F  ------------------------------CPRCPAPELLGGPSVFLFPPKPKDT 260       270       280       290       300       310
IgG1  LMISRTPEVTCVVVDVSHEDPEVKFNWYVDGVEVHNAKTKPREEQYNSTYRVVSVLTVLH
IgG3  LMISRTPEVTCVVVDVSHEDPEVQFKWYVDGVEVHNAKTKPREEQFNSTFRVVSVLTVLH
113F  LMISRTPEVTCVVVDVSHEDPEVQFKWYVDGVEVHNAKTKPREEQFNSTFRVVSVLTVLH
                                    *
                                              CH3
                                             ┌─────►
         320       330       340             350       360       370
IgG1  QDWLNGKEYKCKVSNKALPAPIEKTISKAKGQPREPQVYTLPPSRDELTKNQVSLTCLVK
IgG3  QDWLNGKEYKCKVSNKALPAPIEKTISKTKGQPREPQVYTLPPSREEMTKNQVSLTCLVK
113F  QDWLNGKEYKCKVSNKALPAPIEKTISKTKGQPREPQVYTLPPSREEMTKNQVSLTCLVK
                                  *                   *

380       390       400       410       420       430
IgG1  GFYPSDIAVEWESNGQPENNYKTTPPVLDSDGSFFLYSKLTVDKSRWQQGNVFSCSVMHE
IgG3  GFYPSDIAVEWESSGQPENNYNTTPPMLDSDGSFFLYSKLTVDKSRWQQGNIFSCSVMHE
113F  GFYPSDIAVEWESSGQPENNYNTTPPMLDSDGSFFLYSKLTVDKSRWQQGNIFSCSVMHE
                            *** *

440
IgG1  ALHNHYTQKSLSLSPGK
IgG3  ALHNRFTQKSLSLSPGK
113F  ALHNHYTQKSLSLSPGK
```

Fig. 6
(a)
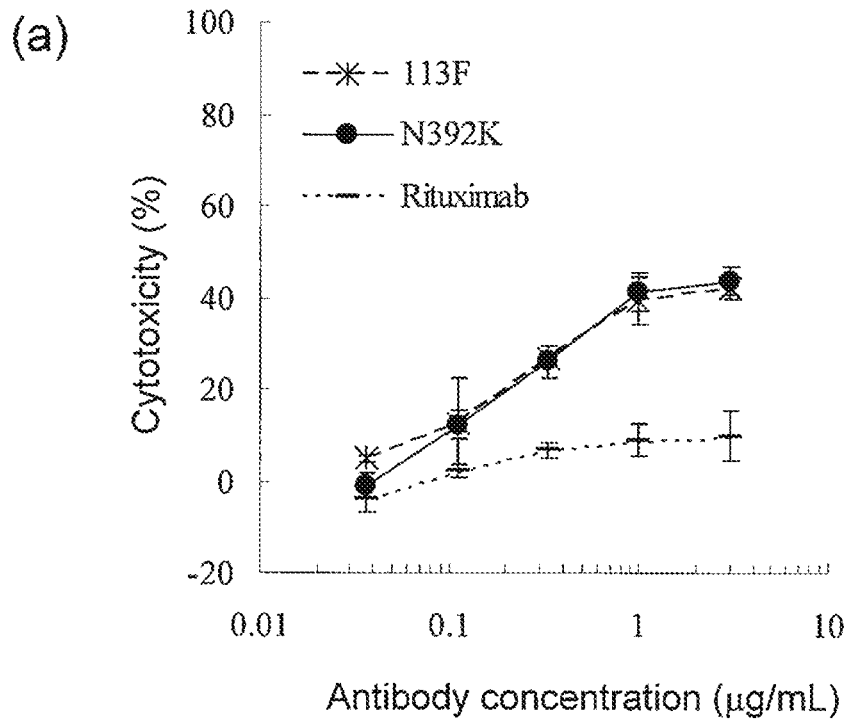
(b)
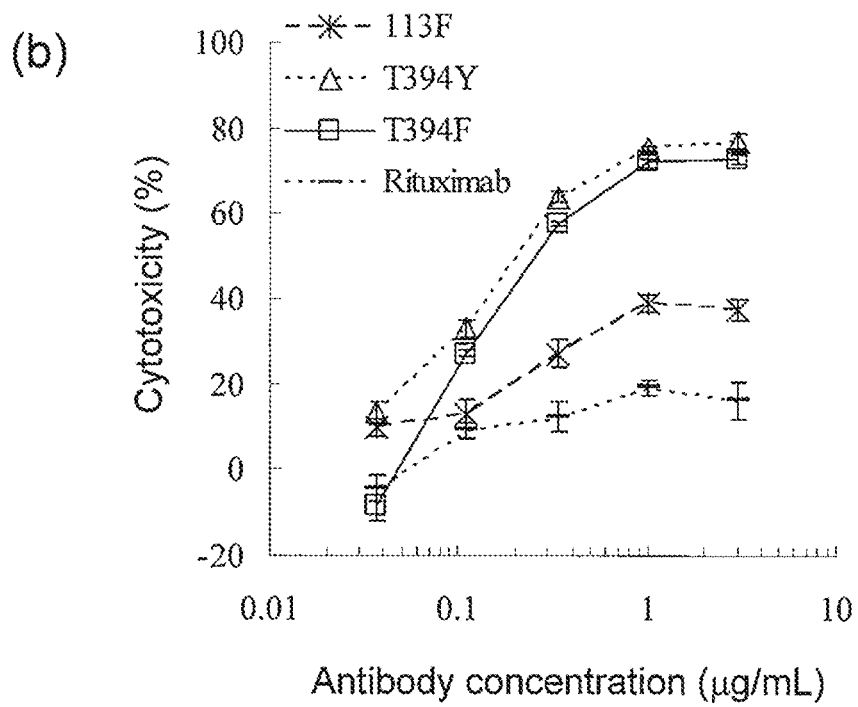

Fig. 7
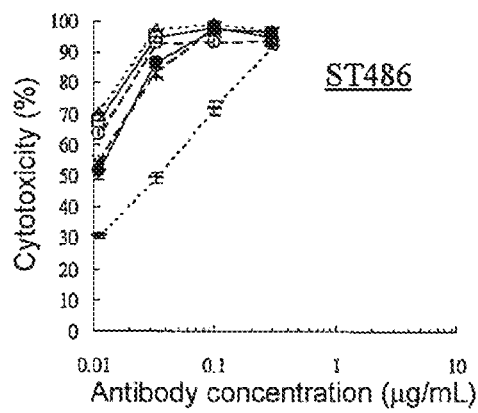
(a)
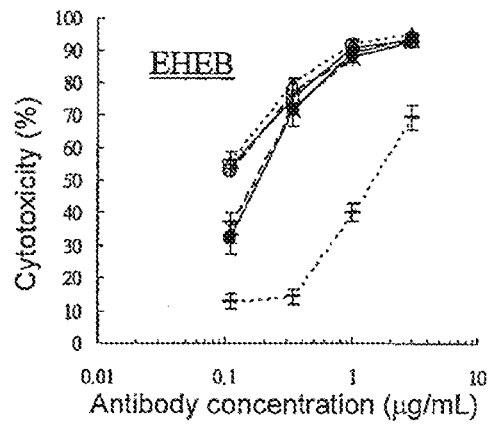
(b)
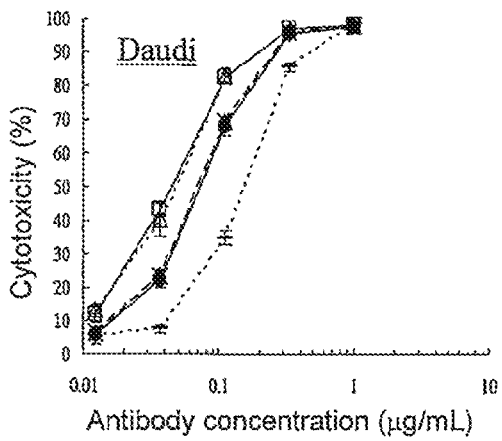
(c)
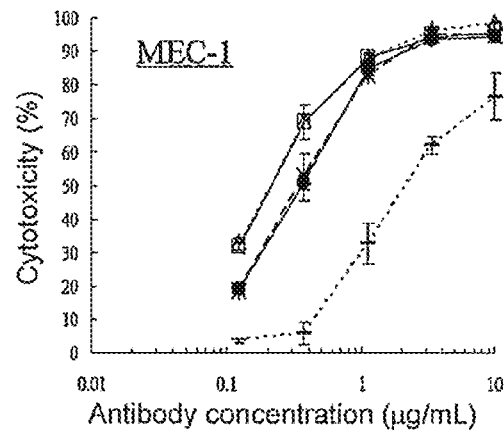
(d)
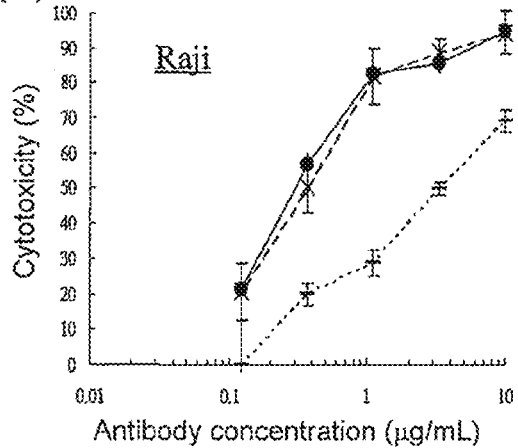
(e)
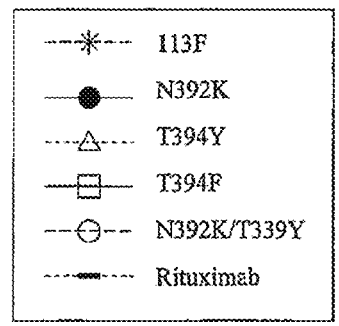

ANTIBODY VARIANTS COMPOSITION

BACKGROUND OF THE INVENTION

1. Field of the Invention

This invention relates to an antibody variant composition in which, among N-glycoside-linked sugar chains which are bound to the Fc region of an antibody, sugar chains which are bound to Asn residues at position other than position 297 according to the EU index are decreased or deleted; an antibody variant composition in which, among N-glycoside-linked sugar chains which are bound to the Fc region of an antibody, extra sugar chains which are bound to Asn residues at positions other than position 297 according to the EU index are decreased or deleted and effector activity of the antibody is maintained; a DNA encoding the antibody variant molecules; a cell capable of producing the antibody variant composition, a process for producing the antibody variant composition; and a method for reducing extra sugar chains which are bound to Asn residues at position other than position 297 according to the EU index among the N-glycoside-linked sugar chains which bind to the Fc region of the antibody.

2. Brief Description of the Background Art

Since antibodies have high binding activity and binding specificity and high stability in blood, their applications to the diagnostic, preventive and therapeutic agents of various human diseases have been attempted (Non-patent Document 1). In addition, human chimeric antibodies or humanized antibodies were prepared from non-human animal antibodies making use of recombinant techniques (Non-patent Documents 2 to 5).

A human chimeric antibody comprises an antibody variable region of a non-human animal antibody and a constant region of a human antibody. A humanized antibody is an antibody in which complementarity determining regions (hereinafter referred to as CDR) of a non-human animal antibody is substituted with CDRs of a human antibody.

The human chimeric antibodies and humanized antibodies resolved problems possessed by non-human animal antibodies such as mouse antibodies, such as the high immunogenicity, low effector function and short blood half-life, and applications of monoclonal antibodies to pharmaceutical preparations were made possible by using them (Non-patent Documents 6 to 9). In the Unites States, for example, a plural of humanized antibodies have already been approved as an antibody for cancer treatment, and are on the market (Non-patent Document 10).

These human chimeric antibodies and humanized antibodies actually show effects to a certain degree at clinical level, but therapeutic antibodies having higher effects are required.

For example, in the case of single administration of Rituxan (registered tradename) (Non-patent Document 11) (manufactured by IDEC/Roche/Genentech) which is a human chimeric antibody to CD20, it was reported that its response rate for recurrent low malignancy non-Hodgkin lymphoma patients in the phase III clinical test is no more than 48% (complete remission 6%, partial remission 42%), and its average duration of response is 12 months (Non-patent Document 12).

In the case of combination use of Rituxan (registered tradename) and chemotherapy (CHOP: Cyclophosphamide, Doxorubicin, Vincristine), it was reported that its response ratio for recurrent low malignancy and follicular non-Hodgkin lymphoma patients by the phase II clinical test is 95% (complete remission 55%, partial remission 45%), but side effects due to CHOP were found (Non-patent Document 13).

In the case of single administration of Herceptin (registered tradename) (manufactured by Genentech) which is a humanized antibody to HER2, it was reported that its response ratio for metastatic breast cancer patients in the phase III clinical test is only 15%, and its average duration of response is 9.1 months (Non-patent Document 14).

The human antibody molecule is also called immunoglobulin (hereinafter referred to as Ig) and classified into isotypes of IgA, IgD, IgE, IgG, and IgM based on its molecular structure.

An antibody molecule of human IgG (hereinafter referred to as IgG) type which is mainly used as a therapeutic antibody is an antibody molecule comprises two heavy chains (hereinafter referred to as H chain) and two light chains (hereinafter referred to as L chain).

An H chain comprises individual domain structures which are respectively called an H chain variable region (hereinafter referred to as VH), CH1, hinge, CH2 and CH3 domains from the N-terminal. Also, the CH2 domain and CH3 domain in combination are called Fc region.

An L chain comprises individual domain structures which are respectively called an L chain variable region (hereinafter referred to as VL) and an L chain constant region (hereinafter referred to as CL) from the N-terminal.

The H chain of the IgG type antibody includes four subclasses consisting of IgG1, IgG2, IgG3 and IgG4. The H chains of the individual IgG subclasses are homologous with each other at almost 95% amino acid sequence identity in the constant region, except for highly-variable hinges.

Although individual IgG subclasses have highly homologous with each other in the amino acid sequence, they have different biological activity in strength (Non-patent Document 15). Examples of the biological activities include an effector function such as a complement-dependent cytotoxicity (hereinafter referred to as CDC activity), an antibody-dependent cellular cytotoxicity (hereinafter referred to as ADCC activity) and a phagocytic activity. These activities play an important role in eliminating foreign substances and pathogens in the living body.

A family of Fcy receptor (hereinafter referred to as FcγR) is expressed on the surface of various leukocytes such as natural killer cells (hereinafter referred to as NK cell), monocytes, macrophages, granulocytes and the like.

FcγR is classified into active type FcγR such as FcγRI, FcγRIIa, FcγRIIIa and FcγRIIIb and inhibitory type FcγR such as FcγRIIb. IgG antibodies, particularly IgG1 and IgG3 in human, strongly bind to these receptors so that they induce ADCC activity and phagocytosis by leucocytes.

ADCC activity means a cell lysis reaction which is generated by cytotoxic molecules released from NK cell, such as perforin and granzyme, as a result that an antibody bound to an antigen mainly binds to FcγRIIIa on the NK cell surface via the Fc moiety (Non-patent Documents 16 and 17). In general, ADCC activity shows an order of IgG1>IgG3>>IgG4≥IgG2 (Non-patent Documents 18 and 19). A binding site to FcγRIIIa on the Fc of the antibody is present in CH2 domain, and a crystal structure analysis shows that one molecule of FcγRIIIa binds to the space between two CH2 domains (Non-patent Document 20).

CDC activity means a reaction in which an antibody bound to its antigen activates reaction cascade of a group of serum proteins called complement system and finally lyses the target cell. CDC activity is high in human IgG1 and IgG3 and generally shows an order of IgG3≥IgG1>>IgG2≈IgG4. The complement system is classified into respective components of C1 to C9, and most of them are enzyme precursors which express the enzyme activity by partial degradation.

CDC activity induces the cell lysis reaction by starting from the binding of C1q as one component of C1 to the Fc region of an antibody on the target cell, advancing activation cascade by partial degradation of respective component by the components of the previous step, and finally forming a pore forming unit which is called membrane attack complex formed by C5 to C9 on the cell membrane of target cell (Non-patent Documents 16 and 17). An Fc region amino acid substitution study suggests that the binding site of C1q on the Fc region is present in the CH2 domain (Non-patent Document 21)

Importance of the above-mentioned effector function is recognized also in the drug effect mechanism of a therapeutic antibody to be used in clinical practice. The above-mentioned Rituxan (registered trademark) is a human chimeric antibody of IgG1 subclass and exhibits ADCC activity and CDC activity in vitro (Non-patent Document 22).

Further, regarding its clinical effect, Rituxan (registered trademark) is suggested to actually exhibit the effector function in the human body of patients, since Rituxan (registered trademark) exhibits high therapeutic effect in patients having FcγRIIIa genotype which shows strong ADCC activity (Non-patent Document 23), the complement components in blood are quickly consumed after administration (Non-patent Document 24), expression of CD59 which is a factor to inhibit CDC activity is increased in the cancer cells of patients who recurred after administration (Non-patent Document 25), and the like.

Herceptin (registered trademark) is also an IgG1 subclass humanized antibody, and it was reported to exhibit high therapeutic effects in patients having FcγRIIIa genotype which shows strong ADCC activity (Non-patent Document 26).

In addition, since human IgG escaped from degradation by lysosome by binding to a neonatal Fc receptor (neonatal Fc receptor for IgG; FcRn, hereinafter referred to as FcRn) which is expressed on such as vascular endothelial cell, under low pH conditions in endosome, it has a long blood half-life for 7 days (IgG3) to 21 days (IgG1, IgG2 and IgG4). Based on study on the Fc amino acid residue substitution it is suggested that the binding site of the antibody Fc and FcRn is present in the interface of CH2 domain and CH3 domain (Non-patent Document 27).

Based on the above, the human IgG1 antibody is most suitable as a therapeutic antibody since it has higher ADCC activity and CDC activity and further has longer half-life in human blood than other subclasses.

C1q is known to bind to the Fc region of the antibody molecule. The binding constants (Ka) in the binding of C1q to a monomeric antibody molecule in human IgG1, IgG2, IgG3 and IgG4 are $1.2 \times 10^4$, $0.64 \times 10^4$, $2.9 \times 10^4$ and $0.44 \times 10^4$ respectively (Non-patent Document 28). As discussed the above, especially CH2 domain among the Fc region is important (Non-patent Document 29).

Further in detail, regarding EU index (Non-patent Document 30), it is known that Len 235 (Non-patent Document 31), Asp 270, Lys 322, Pro 329 and Pro 331 (Non-patent Document 32) in the CH2 are important in human IgG1, and Glu 233, Leu 234, Leu 235, Gly 236 (Non-patent Document 33), and Lys 322 (Non-patent Document 34) are important for human IgG3.

Attempts to enhance CDC activity by preparing a IgG variant by introducing amino acid substitutions in human IgG heavy chain constant region, and thereby increasing its binding activity to C1q.

Idusogie et al. reported that CDC activity is enhanced about 2-fold at the maximum when Lys at position 326 or Glu at position 333 according to the EU index in the CH2 domain of the heavy chain constant region of an anti-CD20 chimeric antibody Rituxan (registered trademark) comprising a human IgG1 type constant region and a mouse-derived variable region is substituted with other amino acid (Non-patent Document 35, Patent Document 2).

Idusogie et al. further showed that the CDC activity of IgG2 which was about one per several hundreds of the CDC activity of IgG1 increases to about ½s of the CDC activity of IgG1 when Lys at position 326 or Glu at position 333 according to the EU index in the human IgG2 type antibody is substituted with other amino acid (Patent Documents 3 to 5).

In addition, Dall'Acqua et al. reported that by applying various amino acid substitutions to the hinge region of a human IgG1 type anti-EphA2 antibody, plural of variants are exhibit higher C1q binding activity and higher CDC activity than those of the antibody before the substitutions (Non-patent Document 35).

Different from the techniques for introducing amino acid substitutions, an example in which CDC activity is enhanced by a combination of naturally existing sequences is also known. Shitara et al. found that when the full CH2 domain of human IgG1 and the full CH3 domain or a part of its N terminal side of human IgG1 are substituted with the sequence of human IgG3, the C1q binding activity and the CDC activity are greatly increased than those of IgG1 and IgG3 (Patent Document 6, Non-patent Document 36).

Two types are existed in the sugar chains bound to a protein, that is, N-glycoside-linked sugar chain and O-glycoside-linked sugar chain. The sugar chain which is linked to the N atom of amide group in the side chain of Asn in the protein is N-glycoside-linked sugar chain, and the sugar chain which is linked to the O atom of a hydroxyl group in the side chain of Ser and Thr in the protein is O-glycoside-linked sugar chain.

The N-glycoside-linked sugar chain includes three types, that is, a high mannose type sugar chain, a complex type sugar chain and a hybrid type sugar chain.

The process of biosynthesis of N-glycoside-linked sugar chain starts in the rough-surfaced endoplasmic reticulum from the attachment of dolichol-pyrophosphoric acid-oligosaccharide containing 9 molecules of mannose (Man) $[(Glc)_3(Man)_9(GlcNAc)_2]$ to the Asn residue of a consensus sequence Asn-X-Ser/Thr (X is any amino acid other than proline) of the N-glycoside-linked sugar chain. Thereafter, the sugar chain intermediate is converted into high mannose types such as Man8 type, Man7 type, Man6 type and Man5 type by various enzymes to synthesize complex type sugar chains to which N-acetylglucosamine, galactose, sialic acid, fucose and the like, instead of mannose, is linked (Non-patent Document 37).

However, it is known that the N-glycoside-linked sugar chain is not linked to all of the Asn-X-Ser/Thr sequences in a protein and is not linked further depending on the peripheral amino acid sequences and three-dimensional structure. Particularly, it is known that the addition of sugar chain hardly occurs to the Asn residue of Asn-X-Ser/Thr when the amino acid next to the C-terminal side of Asn-X-Ser/Thr is Pro (Non-patent Documents 38 and 39).

It is known that a complex-type N-glycoside-linked sugar chain binds to only Asn at position 297 of the CH2 domain in the constant region of the human IgG (Non-patent Document 40), however it is not known that the sugar chain binds to other position. It is known only that extra N-glycoside-linked sugar chain is linked to Asn at position 471 of constant region of mouse IgG3 (Non-patent Document 41).

On the other hand, a sequence of Asn-Thr-Thr is present at positions 392 to 394 of the CH3 domain in the human IgG3 type constant region, but the amino acid at position 395 is Pro (Non-patent Document 42), and actually, addition of sugar chain to Asn at position 392 of IgG3 is not known.

It is known that ADCC activity of human IgG is changed depending on the structure of the complex-type N-glycoside-linked sugar chain to be added to the Asn at position 297 (a typical schematic illustration of complex-type sugar chain is shown in FIG. 1) (Patent Document 7).

Although there are reports stating that the ADCC activity of antibodies changes depending on the containing amounts of galactose and N-acetylglucosamine in the sugar chains to be linked to the antibodies (Non-patent Documents 43 to 46), a substance which exerts most influence upon ADCC activity is the fucose that performs α1,6 bond to the reducing terminal of N-acetylglucosamine (hereinafter referred to as a core fucose in some cases).

An IgG antibody comprising a complex-type N-glycoside-linked sugar chain having no core fucose shows markedly higher ADCC activity than that of an IgG antibody comprising complex-type N-glycoside-linked sugar chain having core fucose (Non-patent Documents 47 and 48, Patent Document 7).

As the cells which produce an antibody composition comprising complex-type N-glycoside-linked sugar chains having no core fucose, cells in which α1,6-fucosyltransferase gene was knocked out are known (Patent Documents 8 and 9).

All of FcγR-dependent activities such as ADCC activity, phagocytosis, CDC activity and FcRn binding activity are important for the therapeutic effect of a therapeutic antibody.

However, since all of the C1q binding which is the initial stage of inducing CDC activity, binding to FcγR which is the initial stage of inducing ADCC activity and binding to FcRn which contributes to the long blood half life are effected via the antibody Fc region of the antibody, there is a possibility that these activities are decreased when an amino acid substitution is introduced into the Fc region of the antibody.

Idusogie et al. reported that ADCC activity is greatly decreased in the case of introducing an amino acid point mutation into the CH2 domain of CDC activity-enhanced IgG1 (Non-patent Document 49).

Also, Dall'Acqua et al. reports a phenomenon that introduction of amino acid mutation into the CH2 domain of IgG1 for increasing binding activity to FcRn decreases ADCC activity at the same time (Non-patent Document 50).

Interestingly, these reports show that although the binding sites to FcγRIIIa, C1q and FcRn in the Fc are positioned at slightly different site, the amino acid substitution for changing each binding activity has unexpected influences upon other binding sites.

The amino acid at position 392 of the IgG heavy chain constant region is positioned at the interface of two CH3 domains in the antibody molecule (Non-patent Document 51). Since the amino acid positioned at the interface plays an important role in the association of two heavy chain molecules (Non-patent Document 52), for example, when the amino acid at position 392 is modified, there is a possibility that it has unexpected influences upon the three-dimensional structure and various biological activities of the antibody molecule.

CITATION LIST

Patent Document

Patent Document 1: EP0327378
Patent Document 2: US2003/0158389
Patent Document 3: WO00/42072
Patent Document 4: US2004/0132101
Patent Document 5: US2005/0054832
Patent Document 6: WO2007/011041
Patent Document 7: WO00/61739
Patent Document 8: WO02/31140
Patent Document 9: WO03/85107

Non-patent Document

Non-patent Document 1: *Monoclonal Antibodies: Principles and Applications*, Wiley-Liss, Inc., (1995)
Non-patent Document 2: *Nature*, 312, 643 (1984)
Non-patent Document 3: *Proc. Natl. Acad. Sci. USA*, 81, 6851 (1984)
Non-patent Document 4: *Nature*, 321, 522 (1986)
Non-patent Document 5: *Nature*, 332, 323 (1988)
Non-patent Document 6: *Immunol. Today*, 21, 364 (2000)
Non-patent Document 7: *Immunol. Today*, 21, 403 (2000)
Non-patent Document 8: *Ann. Allergy Asthma Immunol.*, 81, 105 (1998)
Non-patent Document 9: *Nature Biotechnol.*, 16, 1015 (1998)
Non-patent Document 10: *Nature Reviews Cancer*, 1, 119 (2001)
Non-patent Document 11: *Curr. Opin. Oncol.*, 10, 548 (1998)
Non-patent Document 12: *J. Clin. Oncol.*, 16, 2825 (1998)
Non-patent Document 13: *J. Clin. Oncol.*, 17, 268 (1999)
Non-patent Document 14: *J. Clin. Oncol.*, 17, 2639 (1999)
Non-patent Document 15: *Monoclonal Antibodies: Principles and Applications*, Wiley-Liss, Inc., (1995)
Non-patent Document 16: *Chemical Immunology*, 65, 88 (1997)
Non-patent Document 17: *Immunol. Today*, 20, 576 (1999)
Non-patent Document 18: *Nature*, 332, 323 (1988)
Non-patent Document 19: *Journal of Experimental Medicine*, 166, 1351 (1987)
Non-patent Document 20: *Nature*, 406, 267 (2000)
Non-patent Document 21: *J. Immunol.*, 166, 2571 (2001)
Non-patent Document 22: *Oncogene*, 22, 7359 (2003)
Non-patent Document 23: *Blood*, 99, 754 (2002)
Non-patent Document 24: *J. Immunol.*, 172, 3280 (2004)
Non-patent Document 25: *J. Clin. Oncol.*, 21, 1466 (2003)
Non-patent Document 26: *J. Clin. Oncol.*, 26, 1789 (2008)
Non-patent Document 27: *Nature Reviews Immunology*, 7, 715 (2007)
Non-patent Document 28: *Biochemistry*, 15, 5175 (1976)
Non-patent Document 29: *Journal of Experimental Medicine*, 173, 1025 (1991)
Non-patent Document 30: *Proc. Natl. Acad. Sci. U.S.A.*, 63, 78 (1969)
Non-patent Document 31: *Immunology*, 86, 319 (1995)
Non-patent Document 32: *J. Immunol.*, 164, 4178 (2000)
Non-patent Document 33: *Mol. Immunol.*, 34, 1019 (1997)
Non-patent Document 34: *Mol. Immunol.*, 37, 995 (2000)

Non-patent Document 35: *The Journal of Immunology*, 177, 1129 (2006)
Non-patent Document 36: *Cancer Research*, 68, 3863 (2008)
Non-patent Document 37: *Molecular Cell Biology*, Third Edition, W. H. Freeman and company, New York, N.Y. and Oxford (1995)
Non-patent Document 38: *Protein Engineering*, 3, 433 (1990)
Non-patent Document 39: *Biochemistry*, 37, 6833 (1998)
Non-patent Document 40: *Immunology*, Fifth Edition, Mosby International Ltd (1998)
Non-patent Document 41: *Mol. Immunol*, 34, 593 (1997)
Non-patent Document 42: *Sequences of Proteins of Immunological Interest*, Fifth Edition, US Dept. Health and Human Services (1991)
Non-patent Document 43: *Human Antib Hybrid*, 5, 143 (1994)
Non-patent Document 44: *Hum Antib Hybrid*, 6, 82 (1995)
Non-patent Document 45: *Nat. Biotechnol.*, 17, 176 (1999)
Non-patent Document 46: *Biotechnol. Bioeng.*, 74, 288 (2001)
Non-patent Document 47: *J. Biol. Chem.*, 277, 26733 (2002)
Non-patent Document 48: *J. Biol. Chem.*, 278, 3466 (2003)
Non-patent Document 49: *The Journal of Immunology*, 166, 2571 (2001)
Non-patent Document 50: *J. Biol. Chem.*, 281, 23514, (2006)
Non-patent Document 51: *Protein Engineering*, 9, 617 (1996)
Non-patent Document 52: *Immunology*, 105, 9 (2002)

SUMMARY OF THE INVENTION

Among the N-glycoside-linked sugar chains which bind to the Fc region of an antibody, the sugar chain that binds to Asn at position 297 relates to the activity and blood stability of the antibody, but there is a possibility that extra sugar chains linked to the amino acid residues at positions other than position 297 have influences upon the antibody constant region-mediated activity and a possibility of causing a problem of uniformity as a therapeutic antibody preparation. Accordingly, among the N-glycoside-linked sugar chains which bind to the Fc region of an antibody, a method for controlling extra sugar chains which bind to the Asn residues at positions other than position 297 according to the EU index is required.

Accordingly, an object of the present invention is to provide an antibody variant composition in which, among the N-glycoside-linked sugar chains which bind to the Fc region of an antibody, sugar chains which bind to Asn residues at positions other than position 297 according to the EU index are decreased or deleted.

Based on the above-mentioned problems, the inventors conducted examinations and found that, among the N-glycoside-linked sugar chains which bind to the Fc region of an antibody, sugar chains which bind to Asn residues at positions other than position 297 according to the EU index are decreased or deleted by carrying out at least one amino acid substitution selected from an amino acid substitution of Asn to other amino acid residue, an amino acid substitution of X to Pro and an amino acid substitution of Ser/Thr to other amino acid residue in amino acid residues of an Asn-X-Ser/Thr (X is an amino acid residue other than Pro) sequence at positions other than positions of 297 to 299 according to the EU index in the Fc region of a human IgG antibody, and thus accomplished the present invention.

The antibody variant composition and the fragment of the antibody variant composition according to the present invention include an antibody variant composition in which, among the N-glycoside-linked sugar chains which bind to the Fc region of an antibody, sugar chains which bind to Asn residues at positions other than position 297 according to the EU index are decreased or deleted; an antibody variant composition in which, among the N-glycoside-linked sugar chains which bind to the antibody Fc region, extra sugar chains which bind to Asn residues at positions other than position 297 according to the EU index are decreased or deleted and effector activity of the antibody is maintained; and fragments of the antibody variant compositions.

Since in the antibody variant compositions and fragments of the antibody variant compositions of the present invention, among the N-glycoside-linked sugar chains which bind to the Fc region of an antibody, sugar chains which bind to Asn residues at positions other than position 297 according to the EU index are decreased or deleted. Accordingly they do not have influences upon the antibody constant region-mediated activity by extra sugar chains bound to the amino acid residues at positions other than position 297 and do not cause a problem of uniformity as a therapeutic antibody preparation and therefore are markedly useful.

BRIEF DESCRIPTION OF THE DRAWINGS

FIGS. 1(*a*) and (*b*) represent typical structure of complex-type N-glycoside-linked sugar chain (complex type sugar chain).

FIG. 2(*a*) to (*c*) represent structures of the 113F type antibody which is IgG1/IgG3 domain swapped antibody and has a high CDC activity.

FIG. 3 is an illustration showing an SDS-PAGE image of GM2-113F. Lane 1 is molecular weight markers and lane 2 is an analyzed result of GM2-113F. Molecular weights of the molecular weight markers are shown in the left side of FIG. 3.

FIG. 4 shows a comparison of amino acid sequences of H chain constant regions of IgG1 antibody, IgG3 antibody and the 113F type antibody. The amino acid residues shown by a thick character are sites which are amino acids different from those of the IgG1 antibody and IgG3 antibody. The asterisk represents the residue on which an amino acid substitution was carried out in this study.

In FIG. 5, a dotted line in a part of a vector represents that the nucleotide sequences other than the H chain constant region are not confirmed after PCR.

FIGS. 6 (*a*) and (*b*) show measurement results of CDC activity for CD20 transfectant KC1156 at various concentrations of 113F antibody, N392K, T394Y, T394F and rituximab. In the graph, the ordinate represents cytotoxicity (%) and the abscissa represents antibody concentration. The test was carried out by N=3.

FIG. 7 (*a*) to (*e*) show measurement results of CDC activity for CD20-positive tumor cell lines Raji, Daudi, ST486, EHEB and MEC-1 at various concentrations of 113F antibody, N392K, T394Y, T394F, N392K/T339Y and rituximab. In the graph, the ordinate represents cytotoxicity (%) and the abscissa represents antibody concentration. The test was carried out by N=3.

DETAILED DESCRIPTION OF THE INVENTION

Figure 5:
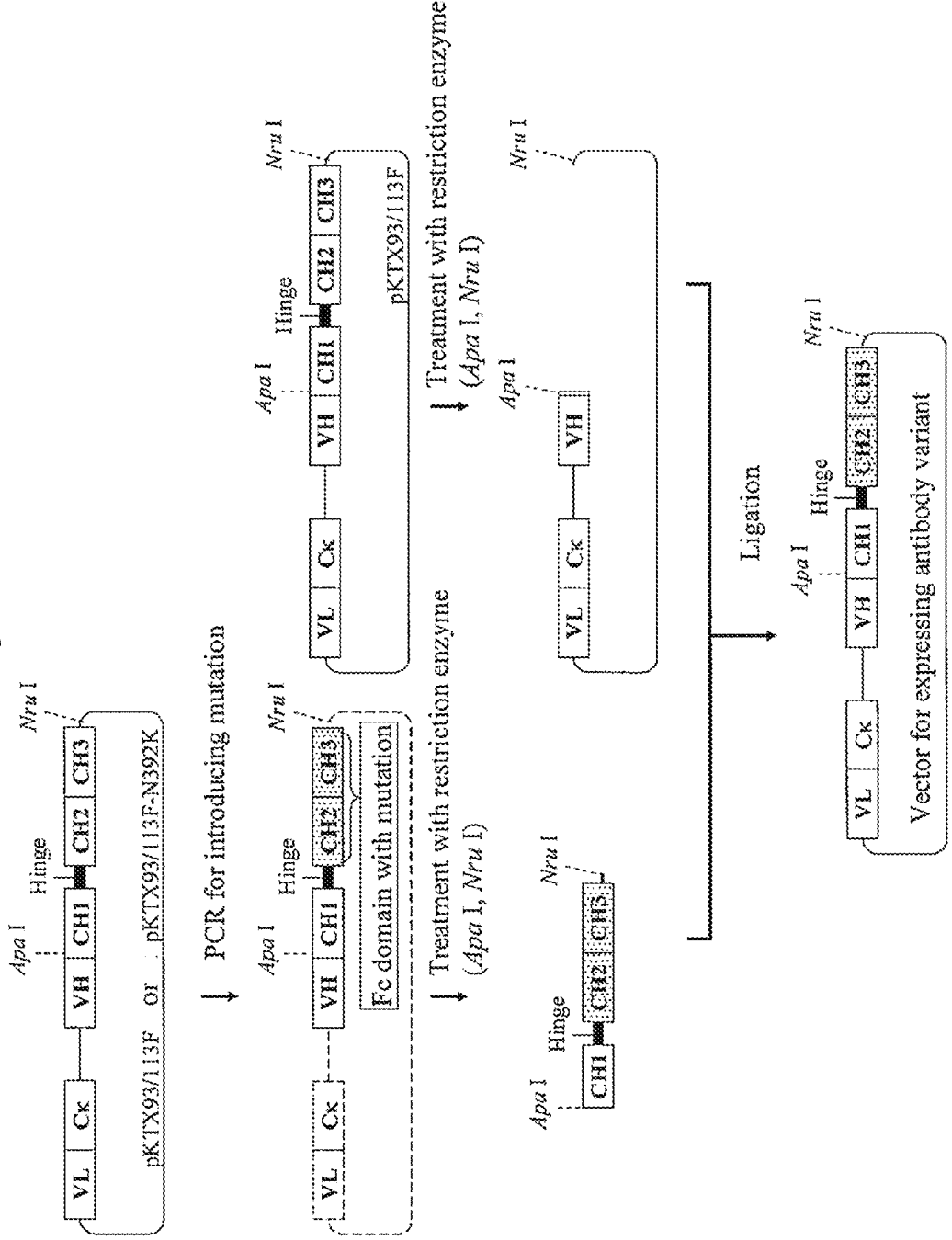
FIG. 5 shows a preparation procedure of expression vector.

The invention relates to the following 1 to 18.

1. An antibody variant composition, comprising amino acid residues of an Asn-X-Ser/Thr (X is an amino acid residue other than Pro) sequence other than at positions 297 to 299 according to the EU index in an Fc region of a human IgG antibody, in which at least one amino acid substitution selected from an amino acid substitution of Asn to other amino acid residue, an amino acid substitution of X to Pro and an amino acid substitution of Ser/Thr to other amino acid residue is carried out, and a fragment of the antibody variant composition.

2. The antibody variant composition or the fragment of the antibody variant composition thereof described in the above item 1, wherein an N-glycoside-linked sugar chain is bound to Asn in the Asn-X-Ser/Thr (X is an amino acid residue other than Pro) sequence at positions other than positions 297 to 299 according to the EU index in the Fc region of the human IgG antibody.

3. The antibody variant composition and or the fragment of the antibody variant composition described in the above item 1 or 2, wherein the Asn-X-Ser/Thr (X is an amino acid residue other than Pro) sequence at positions other than positions 297 to 299 according to the EU index is the amino acid residues at positions 392 to 394 according to the EU index.

4. The antibody variant composition or the fragment of the antibody variant composition described in any one of the above items 1 to 3, wherein at least one amino acid residue of amino acid residues at positions 392 to 394 according to the EU index is substituted with the following amino acid residues:

position 392 according to the EU index: Gly, Ala, Val, Leu, Ile, Met, Pro, Asp, Gln, Glu, Lys, Arg, His, Phe, Tyr or Trp;

position 393 according to the EU index: Pro;

position 394 according to the EU index: Leu, Asn, Asp, Lys, Phe, Tyr or Trp.

5. The antibody variant composition or the fragment of the antibody variant composition described in any one of the above items 1 to 4, wherein the Fc region of a human IgG antibody comprises the amino acid sequence of SEQ ID NO:1.

6. The antibody variant composition or the fragment of the antibody variant composition described in any one of the above items 1 to 5, which comprises a CH1 domain and a hinge domain, in which the CH1 domain and the hinge domain comprise an amino acid sequence derived from the human IgG1 antibody.

7. The antibody variant composition or the fragment of the antibody variant composition described in any one of the above items 1 to 6, which comprises an Fc region in which Thr at position 339 according to the EU index is substituted with an amino acid residue of Asn or Tyr.

8. The antibody variant composition or the fragment of the antibody variant composition described in any one of the above items 1 to 7, which comprises an antibody Fc region in which Met at position 397 according to the EU index is substituted with at least one amino acid residue selected from Gln, Asn, Asp and Phe.

9. A DNA encoding the amino acid sequence of the antibody variant composition or the fragment of the antibody variant composition described in any one of the above items 1 to 8.

10. A vector which comprises the DNA obtainable in the above item 9.

11. A transformant obtained by introducing the vector described in the above item 10 into a host cell.

12. A process for producing the antibody variant composition or the fragment of the antibody variant composition described in any one of the above items 1 to 8, which comprises culturing the transformant described in the above item 11 in a medium, to form and accumulate the antibody variant composition or the fragment of the antibody variant composition described in any one of the above items 1 to 8 in the culture, and purifying the antibody variant composition or the fragment of the antibody variant composition from the culture.

13. A method for reducing N-glycoside-linked sugar chains which are bound to Asn residues in an Asn-X-Ser/Thr (X is an amino acid residues other than Pro) sequence at positions other than positions 297 to 299 according to the EU index in an Fc region of a human IgG antibody, which comprises carrying out at least one amino acid substitution selected from an amino acid substitution of Asn to other amino acid residue, an amino acid substitution of X to Pro and an amino acid substitution of Ser/Thr to other amino acid residue in amino acid residues in the Asn-X-Ser/Thr sequence.

14. The method described in the above item 13, wherein an N-glycoside-linked sugar chain is bound to Asn residue in the Asn-X-Ser/Thr (X is an amino acid residue other than Pro) sequence at positions other than positions 297 to 299 according to the EU index in the Fc region of the human IgG antibody.

15. The method described in the above item 13 or 14, wherein the Asn-X-Ser/Thr (X is an amino acid residue other than Pro) sequence at positions other than at EU index positions of 297 to 299 according to the EU index is at positions 392 to 394 according to the EU index.

16. The method described in any one of the above items 13 to 15, wherein at least one amino acid residue of amino acid residues at positions 392 to 394 according to the EU index is substituted with the following amino acid residues:

position 392 according to the EU index: Gly, Ala, Val, Leu, Ile, Met, Pro, Asp, Gln, Glu, Lys, Arg, His, Phe, Tyr or Trp;

position 393 according to the EU index: Pro;

position 394 according to the EU index: Leu, Asn, Asp, Lys, Phe, Tyr or Trp.

17. The method described in any one of the above items 13 to 16, wherein the Fc region of the human IgG antibody comprises the amino acid sequence of SEQ ID NO:1.

18. The method described in any one of the above items 13 to 17, wherein the human IgG antibody comprises a CH1 domain and a hinge domain, and wherein the CH1 domain and the hinge domain comprise an amino acid sequence derived from the human IgG1 antibody.

The antibody variant composition and the fragment of the antibody variant composition of the present invention are the antibody variant composition in which at least one amino acid substitution selected from an amino acid substitution of Asn to other amino acid residue, an amino acid substitution of X to Pro and an amino acid substitution of Ser/Thr to other amino acid residue is carried out in amino acid residues of an Asn-X-Ser/Thr (X is an amino acid residues other than Pro) sequence at positions other than positions 297 to 299 according to the EU index by Kabat et al. in the Fc region of a human IgG antibody, and a fragment of the antibody variant composition.

According to the invention, the EU index represents *Sequence of Proteins of Immunological Interest,* 5th edition (1991). All of the positions of amino acid residues shown below are numbered based on the EU index unless otherwise noted.

The Asn-X-Ser/Thr sequence means a common sequence in which a sugar chain tends to bind to the $NH_2$ group of Asn residue (hereinafter referred to as an N-glycoside-linked sugar chain consensus sequence or simply as a consensus sequence).

In the invention, examples of the Asn-X-Ser/Thr (X is an amino acid residue other than Pro) sequence at positions other than positions 297 to 299 according to the EU index in the Fc region of a human IgG antibody include Asn in positions 392 to 394.

In addition, specific examples of the antibody variant composition of the present invention include an antibody variant composition in which at least one amino acid substitution selected from an amino acid substitution of Asn to other amino acid residue, an amino acid substitution of X to Pro and an amino acid substitution of Ser/Thr to other amino acid residue is carried out in the Asn-X-Ser/Thr (X is an amino acid residue other than Pro) sequence at positions 392 to 394 according to the EU index in the Fc region of the antibody.

More specific examples of the antibody variant composition of the present invention include the antibody variant composition in which at least one amino acid residue of amino acid residues at positions 392 to 394 according to the EU index in the Fc region of the antibody is substituted with the following amino acid residues, and the like:

position 392 according to the EU index: Gly, Ala, Val, Leu, Ile, Met, Pro, Asp, Gln, Glu, Lys, Arg, His, Phe, Tyr or Trp;

position 393 according to the EU index: Pro;

position 394 according to the EU index: Leu, Asn, Asp, Lys, Phe, Tyr or Trp.

Examples of the Fc region of the human IgG antibody of the present invention include the Fc region in which at least the amino acid sequence of positions 393 to 394 according to the EU index in the Fc region has Asn-Thr-Thr, specifically the Fc region in which an amino acid sequence at positions 231 to 434 according to the EU index are human IgG1 and an amino acid sequence at positions 435 to 447 according to the EU index are human IgG3, further specifically the Fc region comprising the amino acid sequence of SEQ ID NO:1.

Specific examples of the antibody variant composition of the invention include the antibody variant composition in which Asn at position 392 according to the EU index in the Fc region of the human IgG antibody comprising the amino acid sequence of SEQ ID NO:1, is substituted with one amino acid residue selected from Gly, Ala, Val, Leu, Ile, Met, Pro, Asp, Gln, Glu, Lys, Arg, His, Phe, Tyr and Trp, the antibody variant composition in which Thr at position 393 according to the EU index in the Fc region of the human IgG antibody is substituted with Pro, the antibody variant composition in which Thr at position 394 according to the EU index in the Fc region of the human IgG antibody is substituted with one amino acid residue selected from Leu, Asn, Asp, Lys, Phe, Trp and Tyr, and the like.

More specific examples of the antibody variant composition of the invention include the antibody variant composition in which Asn at position 392 according to the EU index in the Fc region of the human IgG antibody comprising the amino acid sequence of SEQ ID NO:1 is substituted with Lys, an antibody variant composition comprising the amino acid sequence of SEQ ID NO:3, and the like.

Further, examples of the antibody variant composition of the invention include the antibody variant composition in which Thr at position 339 according to the EU index in the Fc region of the human IgG antibody comprising the amino acid sequence of SEQ ID NO:1 is substituted with Tyr in addition to the above-mentioned amino acid substitutions, and the antibody variant composition in which Met at position 397 according to the EU index in the Fc region of the human IgG antibody comprising the amino acid sequence of SEQ ID NO:1 is substituted with one amino acid residue selected from Gln, Asn, Asp and Phe in addition to the above-mentioned amino acid substitutions.

In addition, examples of the antibody variant of the present invention include the antibody variant composition comprising the amino acid sequence of SEQ ID NO:3 in which Thr at position 339 according to the EU index is substituted with Tyr and the antibody variant composition comprising the amino acid sequence of SEQ ID NO:3 in which Met at position 397 according to the EU index is substituted with one amino acid residue selected from Gln, Asn, Asp and Phe.

According to the invention, in the amino acid residues of the Asn-X-Ser/Thr (X is an amino acid residue other than Pro) sequence at positions other than positions 297 to 299 according to the EU index in the Fc region of a human IgG antibody, the amino acid residue to be substituted with any amino acid residue of Asn, X and Ser/Thr can be selected by taking the position where amino acid residue substitution is carried out and the amino acid residue after the substitution into consideration in such a manner that a new N-glycoside-linked sugar chain consensus sequence is not made as a result of the amino acid substitution.

By substituting the above-mentioned amino acid residues, the antibody variant composition of the invention results in the reduction or deletion of N-glycoside-linked sugar chains which bind to the Asn residue of the Asn-X-Ser/Thr (X is an amino acid residue other than Pro) sequence at positions other than positions 297 to 299 according to the EU index in the Fc region of a human IgG antibody and has the effector activity equal to or higher than that of the antibody before carrying out the amino acid residue substitution.

Specific examples of the antibody variant composition of the present invention include the antibody variant composition which does not have a sugar chain bound to Asn residue at position 392 according to the EU index and which has an effector activity equal to or higher than those of the antibody before carrying out the amino acid substitution.

In the present invention, "sugar chains which bind to Asn residues are decreased or deleted" means that sugar chains substantially are not bound in an antibody variant composition after carrying out the amino acid substitution as compared with the antibody variant composition before carrying out the amino acid substitution.

In the present invention, "sugar chains substantially are not bound" means that the content of sugar chains which bind to the modified site of the amino acid residue is not detected or is below the detection limit, when subjected to the sugar chain analysis described below.

The antibody variant of the present invention may be any protein as long as it is a protein having a Fc variant and having a binding activity to a target molecule. Specific examples include a monoclonal antibody having a Fc variant, a fusion protein (hereinafter also referred to as immunoadhesin) in which a receptor or a ligand is fused with the Fc region, an Fc fusion protein in which plural Fc regions are fused with the Fc region of an antibody, and the like.

The antibody fragment having binding activity to a target molecule includes Fab, Fab', F(ab')$_2$, scFv, diabody, dsFv, a peptide comprising CDR, and the like.

The antibody variant of the present invention means a protein having a Fc variant.

In the present invention, the Fc variant means an Fc region in which the amino acid substitution is carried out so that sugar chains which bind to the N-glycoside-linked sugar chain consensus sequence at position EU index 297 to 299 according to the EU index among the N-glycoside-linked sugar chains bound to the Fc region are decreased or deleted.

Namely, the Fc variant of the present invention means an Fc region in which the N-glycoside-linked sugar chain consensus sequences are decreased or deleted so that an N-glycoside-linked sugar chain binds to Asn at position 297 according to the EU index in the Fc region and the other extra N-glycoside linked sugar chains do not bind to the Fc region.

In addition, the antibody Fc region or merely Fc in the present invention is any amino acid sequence as long as an amino acid sequence is the Fc amino acid sequence of naturally existing immunogloblin or its allotype reported by Kabat et al. [*Sequences of Proteins of Immunological Interest*, Fifth Edition (1991)], or the Fc amino acid sequence in which the amino acid sequence is modified for the purpose of regulation of an effector activity, antibody stability, extension of half-life in blood and the like (WO00/42072, WO2006/033386, WO2006/105338, WO2005/070963, WO2007/011041 and WO2008/145142). In addition, the antibody Fc region may be any Fc region as long as an Fc region has a binding activity to Fc receptor, and/or an Fc region has an effector activity through Fc region and Fc receptor.

Namely, the antibody variant composition of the present invention means an antibody variant composition comprising the Fc variant in which extra binding of N-glycoside-linked sugar chains to the Fc region other than the amino acid residue at position 297 according to the EU index is decreased or deleted and which has a controlled binding activity to Fc receptor and/or a controlled effector activity.

In the invention, the monoclonal antibody is an antibody secreted by a single clone antibody-producing cell, and recognizes only one epitope (also called antigen determinant) and has uniform amino acid sequence (primary structure). The antibody variant composition of the present invention is an antibody variant substantially having a property of a monoclonal antibody and included in a monoclonal antibody.

Examples of the epitope include a single amino acid sequence, a three-dimensional structure comprising the amino acid sequence, a sugar chain-bound amino acid sequence, a three-dimensional structure comprising a sugar chain-bound amino acid sequence, and the like, recognized and bound by a monoclonal antibody.

The antibody molecule is also called immunoglobulin (hereinafter referred to as Ig), and the human antibody is classified into isotypes of IgA1, IgA2, IgD, IgE, IgG1, IgG2, IgG3, IgG4 and IgM based on its molecular structure. IgG1, IgG2, IgG3 and IgG4 having relatively high homology in amino acid sequences are generically called IgG.

The antibody molecule comprises polypeptides called a heavy chain (hereinafter referred to as H chain) and a light chain (hereinafter referred to as L chain).

Also, the H chain comprises an H chain variable region (hereinafter referred to as VH) and an H chain constant region (hereinafter referred to as CH), and an L chain comprises an L chain variable region (hereinafter referred to as VL) and the L chain constant region (hereinafter referred to as CL) from its N-terminal.

The CH is known to be classified into subclasses of α, δ, ε, γ and μ chain. The CH is further constituted by domains of a CH1 domain, a hinge domain, a CH2 domain and a CH3 domain.

The domain means a functional constitution unit constituting each polypeptide included in the antibody molecule. Also, the CH2 domain and the CH3 domain in combination are called a Fc region or merely Fc. The CL is classified as Cλ chain and Cκ chain.

The CH1 domain, the hinge domain, the CH2 domain, the CH3 domain and the Fc region in the present invention are defined by positions of amino acid residues from the N-terminal according to the EU index.

Specifically, CH1 is defined as the amino acid sequence at positions 118 to 215 according to the EU index, the hinge is defined as the amino acid sequence at positions 216 to 230 according to the EU index, CH2 is defined as the amino acid sequence at positions 231 to 340 according to the EU index, and CH3 is defined as the amino acid sequence at positions 341 to 447 according to the EU index.

The antibody variant of the present invention includes especially a human chimeric antibody (hereinafter simply referred to as a chimeric antibody), a humanized antibody (also referred to as a Complementarity Determining Region (CDR)-grafted antibody), a human antibody and the like.

The chimeric antibody is an antibody which comprises VH and VL of an antibody derived from an animal other than a human (non-human animal), and CH and CL of a human antibody. The non-human animal may be any animal such as a mouse, a rat, a hamster or a rabbit, so long as a hybridoma can be prepared therefrom.

A hybridoma is a cell producing a monoclonal antibody having desired antigen specificity which is obtained by cell fusion of a B cell obtained by immunizing a non-human animal with an antigen, with a myeloma cell derived from a mouse or the like. Accordingly, the variable region constituting the antibody produced by the hybridoma comprises an amino acid sequence of a non-human animal antibody.

The human chimeric antibody can be produced by obtaining cDNAs encoding VH and VL from a monoclonal antibody-producing hybridoma derived from a non-human animal, inserting them into an expression vector for animal cell comprising DNAs encoding CH and CL of human antibody to thereby construct a human chimeric antibody expression vector, and then introducing the vector into an animal cell to express the antibody.

The humanized antibody is the antibody in which amino acid sequences of CDRs of VH and VL of a non-human animal antibody are grafted into appropriate positions of VH and VL of a human antibody. The region other than CDRs of VH and VL is referred to as a framework region (hereinafter referred to as FR).

The humanized antibody can be produced by constructing cDNA encoding an amino acid sequence of VH comprising amino acid sequences of CDRs in VH of a non-human animal and amino acid sequences of FRs in VH of a human antibody and also constructing a cDNA encoding an amino acid sequence of VL comprising amino acid sequences of CDRs in VL of a non-human animal and amino acid sequences of FR in VL of a human antibody; inserting them into an expression vector for animal cell comprising DNAs encoding CH and CL of a human antibody to thereby construct a humanized antibody expression vector; and then introducing the expression vector into an animal cell to express the humanized antibody.

The human antibody is originally an antibody naturally existing in the human body, but it also includes antibodies obtained from a human antibody phage library or a human antibody-producing transgenic animal, which is prepared based on the recent advance in genetic engineering, cell engineering and developmental engineering techniques.

The antibody existing in the human body can be prepared, for example by isolating a human peripheral blood lymphocyte, immortalizing it by infecting with EB virus or the like and then cloning it to thereby obtain lymphocytes capable of producing the human antibody, culturing the lymphocytes thus obtained, and purifying the human antibody from the culture.

The phage library of human antibody is a library in which antibody fragments such as Fab and scFv are expressed on the phage surface by inserting a gene encoding an antibody prepared from a human B cell into a phage gene.

A phage expressing the antibody fragment having the desired antigen binding activity can be recovered from the library, using its activity to bind to the antigen-immobilized substrate as the index. The antibody fragment can be converted further into a human antibody molecule comprising two full H chains and two full L chains by genetic engineering techniques.

A human antibody-producing transgenic animal is an animal in which the human antibody gene is integrated into cells. Specifically, a human antibody-producing transgenic animal can be prepared by introducing a gene encoding a human antibody into a mouse ES cell, grafting the ES cell into an early stage embryo of other mouse and then developing it.

The human antibody is prepared from the human antibody-producing transgenic non-human animal by obtaining a human antibody-producing hybridoma by a hybridoma preparation method usually carried out in non-human mammals, culturing the obtained hybridoma and forming and accumulating the human antibody in the culture.

In the antibody variant of the present invention, the amino acid sequences of VH and VL may be any of amino acid sequences of VH and VL in a human antibody, amino acid sequences of VH and VL in a non-human animal antibody or amino acid sequences of a humanized antibody in which CDRs of a non-human animal are grafted to the framework of a human antibody.

Specific examples include amino acid sequences of VH and VL of a non-human animal antibody produced by a hybridoma, amino acid sequences of VH and VL of a humanized antibody, amino acid sequences of VH and VL of a human antibody, and the like.

The amino acid sequence of CL in the antibody variant of the present invention may be either an amino acid sequence of a human antibody or an amino acid sequence from a non-human animal, but it is preferably Cκ or Cλ of an amino acid sequence of a human antibody.

As the CH of the antibody variant, any CH can be used, so long as it belongs to human immunoglobulin (hIg), and those belonging to the hIgG class are preferred, and any one of the subclasses belonging to the hIgG class, such as γ1 (IgG1), γ2 (IgG2), γ3 (IgG3) and γ4 (IgG4), can be used.

In addition, the amino acid sequence of the CH of the antibody variant of the present invention include not only a naturally existing immunoglobulin CH sequence (including allotypes in each subclass) but also a chimeric type CH sequence combining two or more naturally existing immunoglobulin CH sequences, other amino acid sequences of CH into which an amino acid substitution is introduced in order to regulate effector activity of an antibody.

Examples of the CH of the antibody variant of the present invention include an CH comprising a Fc variant in which at least one amino acid substitution selected from the amino acid substitution of Asn to an amino acid residue other than Ser/Thr, the amino acid substitution of Thr to Pro, and the amino acid substitution of Thr to the other amino acid residue, in Asn, Thr and Thr at positions 392, 393 and 394 according to the EU index, respectively, in the Fc region comprising the amino acid sequence of SEQ ID NO:1 is carried out.

Examples of the CH of the antibody variant of the present invention include a CH comprising a Fc variant in which, in the Fc region comprising the amino acid sequence of SEQ ID NO:1, at least one amino acid substitution selected from the amino acid substitution of Asn at position 392 according to the EU index to one amino acid residue selected from Gly, Ala, Val, Leu, Ile, Met, Pro, Asp, Gln, Glu, Lys, Arg, His, Phe, Tyr and Trp, the amino acid substitution of Thr at position 393 according to the EU index to Pro and the amino acid substitution of Thr at position 394 according to the EU index to one amino acid residue selected from Leu, Asn, Asp, Lys, Phe, Trp and Tyr, is carried out, and the like.

More specific examples of the CH of the antibody variant of the present invention include a CH comprising a Fc variant in which Asn at position 392 according to the EU index in the Fc region comprising the amino acid sequence of SEQ ID NO:1 is substituted with Lys.

Further, examples of the CH of the antibody variant of the present invention include a CH comprising a Fc variant in which Thr at position 339 according to the EU index in the Fc region comprising the amino acid sequence of SEQ ID NO:1 is substituted with Tyr in addition to the above-mentioned amino acid substitutions, a CH comprising a Fc variant in which Met at position 397 according to the EU index in the Fc region comprising the amino acid sequence represented by SEQ ID NO:1 is substituted with one amino acid residue selected from Gln, Asn, Asp and Phe in addition to the above-mentioned amino acid substitutions.

In addition, examples of the CH of the antibody variant of the invention include a CH comprising human IgG1 derived CH1 and hinge domain as a CH domain other than the Fc region.

Examples of the CH of the antibody variant of the present invention include the CH comprising a CH1 and a hinge domain which comprise an amino acid sequence derived from an IgG1 antibody in which at least one amino acid substitution selected from the amino acid substitution of Asn to an amino acid residue other than Ser/Thr, the amino acid substitution of Thr to Pro, and the amino acid substitution of Thr to the other amino acid residue in Asn, Thr and Thr at positions 392, 393 and 394 according to the EU index, respectively, of the Fc region comprising the amino acid sequence of SEQ ID NO:1 is carried out; the CH in which at least one amino acid substitution selected from the amino acid substitution of Asn to an amino acid residue other than Ser/Thr, the amino acid substitution of Thr to Pro, and the amino acid substitution of Thr to the other amino acid residue in Asn, Thr and Thr at positions 392, 393 and 394 according to the EU index, respectively, of the CH of SEQ ID NO:2 is carried out; and the like.

The "effector activity" means an antibody-dependent activity which is induced via an Fc region of an antibody. As the effector activity, an antibody-dependent cellular cytotoxicity (ADCC activity), a complement-dependent cytotoxicity (CDC activity) and an antibody-dependent phagocytosis (ADP activity) by phagocytic cells such as macrophages or dendritic cells, and the like are known.

In the present invention, CDC activity and ADCC activity may be measured using a known measuring method [*Cancer Immunol. Immunother.*, 36, 373 (1993)].

The ADCC activity means an activity to induce cytotoxicity for target cell by activating immune cells (such as natural killer cells) due to the binding of an antibody bound to antigen on the surface of the target cell with an Fc receptor of an immune cell via the Fc region of the antibody.

The Fc receptor (hereinafter referred to as FcR) is a receptor which binds to an Fc region of an antibody and induces various effector activities due to the binding with the antibody.

The FcR corresponds to the subclass of the antibody. IgG, IgE, IgA and IgM are specifically bound to FcγR, FcεR, FcαR and FcμR, respectively.

In addition, the FcγR includes subtypes, such as FcγRI (CD64), FcγRII (CD32) and FcγRIII (CD16) and these subtypes include isoforms, namely, FcγRIA, FcγRIB, FcγRIC, FcγRIIA, FcγRIIB, FcγRIIC, FcγRIIIA, FcγRIIIB, respectively. These different subtypes are expressed on different cell type (*Annu. Rev. Immunol.*, 9, 457-492 (1991)).

In human, FcγRIIIB is expressed specifically on neutrophils, FcγRIIIA is expressed on monocytes, Natural Killer cells (NK cells) and a part of T cells. The binding to an antibody via FcγRIIIA induces NK cell-dependent ADCC activity.

The CDC activity means an activity in which an antibody linked to its antigen on a target cell injures the target cell by activating a series of cascade (complement activation pathway) comprising a group of complement-related proteins in blood. Also, it can induce migration and activation of immunocyte by the protein fragments produced by the activation of complement.

The cascade of CDC activity starts by forming a C1 complex through the linking of C1q comprising a binding domain with the antibody Fc region to the Fc region and its linking to two serine proteases C1r and C1s.

The antibody variants of the present invention in which the sugar chains bound to Asn residues at positions other than position 297 bound to the Fc region are decreased or deleted have the effector activity, C1q binding activity, FcR binding activity and ADCC activity and/or CDC activity that are equal to or higher than those of the antibodies in which sugar chains bind to Asn residues at position other than position 297.

In addition, the antibody variant composition of the invention has C1q binding activity, FcR binding activity and ADCC activity and/or CDC activity which are substantially equal to or higher than those of the antibody before amino acid substitution (to be referred also to as parent antibody).

The term "has substantially C1q binding activity, FcR binding activity and ADCC activity and/or CDC activity which are equal to or higher than those of the parent antibody" means that at least one of activities selected from FcR binding activity, ADCC activity and CDC activity are equal to or higher than the activities of the parent antibody when the antibody variants of the invention and the parent antibody are simultaneously analyzed in the same experimental condition.

The term "substantially equal as compared with the activity of the parent antibody before carrying out the amino acid substitution" means that, when the activity of parent antibody is regarded as 100%, the activity of the antibody variants is preferably 75%, more preferably 80%, further preferably 85%, more further preferably 90%, more further preferably 95%, more further preferably 96%, more further preferably 97%, more further preferably 98%, particular preferably 99%, most preferably 100% or more. In addition, the term "equal or higher as compared with the activity of parent antibody before carrying out the amino acid substitution" means that it has the activity of preferably 100%, more preferably 110%, further preferably 120%, more further preferably 130%, particularly preferably 140%, most preferably 150% or more.

Accordingly, the antibody variants of the present invention can control C1q binding activity, FcR binding activity and ADCC activity and/or CDC activity of the antibody variants, and also can reduce or delete the sugar chains which binds to the Asn residues at positions other than position 297 by carrying out at least one amino acid substitution selected from the amino acid substitution of Asn to other amino acid residue, the amino acid substitution of X to Pro and the amino acid substitution of Ser/Thr to other amino acid residue in the Asn-X-Ser/Thr (X is an amino acid residue other than Pro) consensus sequence at positions other than position 297 according to the EU index.

Further, in the antibody variant compositions of the present invention, amount of the polymer (association product) and/or amount of the antibody degradation products contained in the composition are reduced. The polymer means a product in which two or more of one antibody molecules (monomer) are polymerized via a bond such as hydrophobic bond, hydrogen bond and the like, and examples include a dimer, a trimer, an oligomer in which several molecules are polymerized, a polymer in which several or more molecules are polymerized, and the like.

In addition, sometimes the polymer is referred to as aggregate. Also, the antibody degradation product may be any substance as long as it is a degradation product of an antibody molecule which can be produced enzymatically or non-enzymatically, and examples include a fragmented antibody, oxidized product, deamidation product, isomerization product and the like.

Accordingly, the antibody variant composition of the present invention containing at least one amino acid substitution selected from the amino acid substitution of Asn to other amino acid residue, amino acid substitution of X to Pro and amino acid substitution of Ser/Thr to other amino acid residue in the Asn-X-Ser/Thr (X is an amino acid residue other than Pro) consensus sequence at positions other than position 297 according to the EU index is useful as an antibody pharmaceutical preparation since the amount of polymer and/or the amount of antibody variant degradation product is reduced in preparing and producing the antibody. More specific examples of the antibody variant composition include the antibody variant composition in which the amino acid residue at position 392 according to the EU index is substituted with Lys.

The antibody fragment in the present invention includes Fab, Fab', F(ab')$_2$, scFv, diabody, dsFv, a peptide comprising CDR, and the like.

An Fab is an antibody fragment having a molecular weight of about 50,000 and having antigen binding activity, in which about a half of the N-terminal side of H chain and the entire L chain, among fragments obtained by treating IgG with a protease, papain (cleaving an amino acid residue of the H chain at position 224), are bound together through a disulfide bond (S—S bond).

An F(ab')$_2$ is an antibody fragment having antigen binding activity and having a molecular weight of about 100,000 which is somewhat larger than one in which Fab are bound via an S—S bond in the hinge region, among fragments obtained by treating IgG with a protease, pepsin (by cleaving an amino acid residue of the H chain at position 234).

An Fab' is an antibody fragment having a molecular weight of about 50,000 and having antigen binding activity, which is obtained by cleaving an S—S bond in the hinge region of the F(ab')$_2$.

An scFv is a VH-P-VL or VL-P-VH polypeptide in which one chain VH and one chain VL are linked using an appropriate peptide linker (P) having 12 or more residues and is an antibody fragment having antigen binding activity.

A diabody is an antibody fragment which forms a dimer comprising two scFv having equal to or different antigen binding specificity, and the diabody has divalent antigen binding activity to the same antigen or two specific antigen binding activities to different antigens.

A dsFv is obtained by binding polypeptides in which one amino acid residue of each of VH and VL is substituted with a cysteine residue via an S—S bond between the cysteine residues.

A peptide comprising a CDR is constituted by including at least one region or more of CDRs of VH or VL. A peptide comprising plural of CDRs can be produced by binding directly or via an appropriate peptide linker.

The peptide comprising a CDR can be produced by constructing DNA encoding CDRs of VH and VL of the antibody variant of the present invention, inserting the DNA into an expression vector for prokaryote or an expression vector for eukaryote, and then introducing the expression vector into a prokaryote or eukaryote to express the peptide. The peptide comprising a CDR can also be produced by a chemical synthesis method such as Fmoc method or tBoc method.

The antibody variant composition of the present invention includes antibodies having any specificity, and is preferably the antibody which recognizes a tumor-related antigen, an antibody which recognizes the allergy- or inflammation-related antigen, an antibody which recognizes cardiovascular disease-related antigen, the antibody which recognizes an autoimmune disease-related antigen or the antibody which recognizes a viral or bacterial infection-related antigen, and more preferably the antibody which recognizes a tumor-related antigen.

The tumor-related antigen includes CD1a, CD2, CD3, CD4, CD5, CD6, CD7, CD9, CD10, CD13, CD19, CD20, CD21, CD22, CD25, CD28, CD30, CD32, CD33, CD38, CD40, CD40 ligand (CD40L), CD44, CD45, CD46, CD47, CD52, CD54, CD55, CD59, CD63, CD64, CD66b, CD69, CD70, CD74, CD80, CD89, CD95, CD98, CD105, CD134, CD137, CD138, CD147, CD158, CD160, CD162, CD164, CD200, CD227, adrenomedullin, angiopoietin related protein 4 (ARP4), aurora, B7-H1, B7-DC, integlin, bone marrow stromal antigen 2 (BST2), CA125, CA19.9, carbonic anhydrase 9 (CA9), cadherin, cc-chemokine receptor (CCR) 4, CCR7, carcinoembryonic antigen (CEA), cysteine-rich fibroblast growth factor receptor-1 (CFR-1), c-Met, c-Myc, collagen, CTA, connective tissue growth factor (CTGF), CTLA-4, cytokeratin-18, DF3, E-catherin, epidermal growth factor receptor (EGFR), EGFRvIII, EGFR2 (HER2), EGFR3 (HER3), EGFR4 (HER4), heparin-binding epidermal growth factor-like growth factor (HB-EGF), endoglin, epithelial cell adhesion molecule (EpCAM), endothelial protein C receptor (EPCR), ephrin, ephrin receptor (Eph), EphA2, endotheliase-2 (ET2), FAM3D, fibroblast activating protein (FAP), Fc receptor homolog 1 (FcRH1), ferritin, fibroblast growth factor-8 (FGF-8), FGF8 receptor, basic FGF (bFGF), bFGF receptor, FGF receptor (FGFR) 3, FGFR4, FLT1, FLT3, folate receptor, Frizzled homologue 10 (FZD10), frizzled receptor 4 (FZD-4), G250, G-CSF receptor, ganglioside (such as GD2, GD3, GM2 and GM3), globo H, gp75, gp88, GPR-9-6, heparanase I, hepatocyte growth factor (HGF), HGF receptor, HLA antigen (such as HLA-DR), HM1.24, human milk fat globule (HMFG), hRS7, heat shock protein 90 (hsp90), idiotype epitope, insulin-like growth factor (IGF), IGF receptor (IGFR), interleukin (such as IL-6, IL-12, and IL-15), interleukin receptor (such as IL-2R, IL-3R, IL-6R, IL-10R and IL-15R), integrin, immune receptor translocation associated-4 (IRTA-4), kallikrein 1, KDR, KIR2DL1, KIR2DL2/3, KS1/4, lamp-1, lamp-2, laminin-5, Lewis y, sialyl Lewis x, lymphotoxin-beta receptor (LTBR), LUNX, melanoma-associated chondroitin sulfate proteoglycan (MCSP), mesothelin, MICA, Mullerian inhibiting substance-type II receptor (MISIIR), mucin, neural cell adhesion molecule (NCAM), Necl-5, Notch1, osteopontin, platelet-derived growth factor (PDGF), PDGF receptor, platelet factor-4 (PF-4), phosphatidylserine, Prostate Specific Antigen (PSA), prostate stem cell antigen (PSCA), prostate specific membrane antigen (PSMA), Parathyroid hormone related protein/peptide (PTHrP), receptor activator of NF-kappaB ligand (RANKL), receptor for hyaluronic acid mediated motility (RHAMM), ROBO1, SART3, semaphorin 4B (SEMA4B), secretory leukocyte protease inhibitor (SLPI), SM5-1, sphingosine-1-phosphate, tumor-associated glycoprotein-72 (TAG-72), transferrin receptor (TfR), TGF-beta, Thy-1, Tie-1, Tie2 receptor, T cell immunoglobulin domain and mucin domain 1 (TIM-1), human tissue factor (hTF), Tn antigen, tumor necrosis factor (TNF), Thomsen-Friedenreich antigen (TF antigen), TNF receptor, tumor necrosis factor-related apoptosis-inducing ligand (TRAIL), TRAIL receptor (such as DR4 and DR5), system ASC amino acid transporter 2(ASCT2), trkC, TROP-2, TWEAK receptor Fn14, urokinase plasminogen activator receptor (uPAR), type IV collagenase, urokinase receptor, vascular endothelial growth factor (VEGF), VEGF receptor (such as VEGFR1, VEGFR2 and VEGFR3), vimentin, VLA-4 and the like.

The antibody which recognizes a tumor-related antigen includes anti-GD2 antibody [Anticancer Res., 13, 331 (1993)], anti-GD3 antibody [Cancer Immunol. Immunother., 36, 260 (1993)], anti-GM2 antibody [Cancer Res., 54, 1511 (1994)], anti-HER2 antibody [Proc. Natl. Acad. Sci. USA, 89, 4285 (1992), EP Patent No. 882794], anti-CD52 antibody [Proc. Natl. Acad. Sci. USA, 89, 4285 (1992)], anti-CD4 antibody, anti-MAGE antibody [British J. Cancer, 83, 493 (2000)], anti-CCR4 antibody (U.S. Pat. No. 6,989,145, WO2009/086514), anti-HM1.24 antibody [Molecular Immunol., 36, 387 (1999), WO2002/057316], anti-parathyroid hormone-related protein (PTHrP) antibody [Cancer, 88, 2909 (2000)], anti-basic fibroblast growth factor antibody, anti-fibroblast growth factor 8 antibody [Proc. Natl. Acad. Sci. USA, 86, 9911 (1989)], anti-basic fibroblast growth factor receptor antibody, anti-fibroblast growth factor 8 receptor antibody [J. Biol. Chem., 265, 16455 (1990)], anti-insulin-like growth factor antibody [J. Neurosci. Res., 40, 647 (1995)], anti-insulin-like growth factor receptor antibody [J. Neurosci. Res., 40, 647 (1995)], anti-PSMA antibody [J. Urology, 160, 2396 (1998)], anti-VEGF antibody [Cancer Res., 57, 4593 (1997)], anti-VEGFR antibody [Oncogene, 19, 2138 (2000), WO96/30046], anti-c-Met antibody (U.S. Pat. No. 7,498,420), anti-CD20 antibody [Rituxan (registered trademark), Curr. Opin. Oncol., 10, 548 (1998), U.S. Pat. No. 5,736,137], anti-HER2 antibody [Herceptin (registered trademark), U.S. Pat. No. 5,725,856], anti-HER2 antibody (WO2008/100624, WO2007/077028), anti-Bip antibody (WO2008/105560), anti-CD10 antibody, anti-HB-EGF antibody (WO2007/142277), anti-EGFR antibody (Erbitux (registered trademark), WO1996/402010), anti-Apo-2R antibody (WO98/51793), anti-ASCT2 antibody (WO2010/008075), anti-5T4 antibody (U.S. Application Publication No. 2006/0088522), anti-CA9 antibody (U.S. Pat. No. 7,378,091), anti-CEA antibody [*Cancer Res.*, 55 (23 suppl): 5935s-5945s, (1995)], anti-LewisY antibody, antifolate receptor antibody (WO2005/080431), anti-TROP-2 antibody (U.S. Pat. No. 6,794,494), anti-CD38 antibody, anti-CD33 antibody [Mylotag (registered trademark)], anti-CD22 antibody (Epratuzumab), anti-EpCAM antibody, anti-A33 antibody, anti-IL-3Rα antibody (WO2010/126066), anti-uPAR antibody (U.S. Patent No. 2008/0152587), TRAIL2 antibody (WO2002/94880), and the like.

The antibody which recognizes an allergy- or inflammation-related antigen includes anti-interleukin 6 antibody [*Immunol. Rev.*, 127, 5 (1992)], anti-interleukin 6 receptor antibody [*Molecular Immunol.*, 31, 371 (1994)], anti-interleukin 5 antibody [*Immunol. Rev.*, 127, 5 (1992)], anti-interleukin 5 receptor antibody, anti-interleukin 4 antibody [*Cytokine*, 3, 562 (1991)], anti-interleukin 4 receptor antibody [*J. Immunol. Meth.*, 217, 41 (1998)], anti-interleukin 10 receptor (IL-10R) antibody (WO2009/154995), anti-tumor necrosis factor antibody [*Hybridoma*, 13, 183 (1994)], anti-tumor necrosis factor receptor antibody [*Molecular Pharmacol.*, 58, 237 (2000)], anti-CCR4 antibody [*Nature*, 400, 776 (1999)], anti-CCR5 antibody, anti-CCR6 antibody, anti-chemokine antibody [Peri et al., *J. Immuno. Meth.*, 174, 249-257 (1994)], anti-chemokine receptor antibody [*J. Exp. Med.*, 186, 1373 (1997)] or the like. The antibody which recognizes a cardiovascular disease-related antigen includes anti-GpIIb/IIIa antibody [*J. Immunol.*, 152, 2968 (1994)], anti-platelet-derived growth factor antibody [*Science*, 253, 1129 (1991)], anti-platelet-derived growth factor receptor antibody [*J. Biol. Chem.*, 272, 17400 (1997)], anti-blood coagulation factor antibody [*Circulation*, 101, 1158 (2000)], anti-IgE antibody [Xolair (registered trademark)], anti-CD22 antibody (Epratuzumab), anti-BAFF antibody (Belimumab), anti-$\alpha_v\beta_3$ antibody, anti-$\alpha_4\beta_7$ antibody and the like.

The antibody which recognizes virus- or bacterial infection-related antigen includes anti-gp120 antibody [*Structure*, 8, 385 (2000)], anti-type A influenza virus matrix protein 2 (M2) antibody (WO2003/078600), anti-CD4 antibody [*J. Rheumatology*, 25, 2065 (1998)], anti-CCR5 antibody, anti-verotoxin antibody [*J. Clin. Microbiol.*, 37, 396 (1999)], and the like.

Furthermore, the antibody variant of the present invention has binding activity to protein A.

To have binding activity to protein A means that the antibody variant composition can be purified by using the protein A.

The binding activity to protein A can be measured by ELISA, surface plasmon resonance or the like. Specifically, the antibody composition is allowed to react with protein A solid-phased on a plate and then is further allowed to react with an antibody which recognizes the variously labeled antibodies, and the binding activity can be measured by determining the antibody composition bound to protein A.

The protein A binding activity similar to that of the IgG1 antibody means that when the binding activity or affinity of the antibody variant composition of the present invention or the IgG1 antibody to protein A is measured, the binding activity or activity having affinity is substantially similar to that of the IgG1 antibody.

Also, the antibody composition is allowed to react with protein A bound to a carrier such as sepharose at high pH conditions such as a pH of about 5 to 8, followed by washing, and then the binding activity can be measured by determining the antibody composition eluted at low pH conditions such as a pH of about 2 to 5.

It is almost unknown that sugar chains are bound to the other Asn residues at positions other than position 297 in Fc region of the antibody, although the N-glycoside-linked sugar chains are bound to Asn residue at position 297 in Fc region of the antibody molecule. Accordingly, in general, two sugar chains are bound per one antibody molecule.

The N-glycoside-linked sugar chain which is bound to Asn residue at position 297 in Fc region include a complex-type sugar chain in which the non-reducing terminal side of the core structure (tri-mannosyl core structure) comprises one or plural of parallel side chains of galactose-N-acetylglucosamine (hereinafter referred to as "Gal-GlcNAc") and the non-reducing terminal side of Gal-GlcNAc further comprises a structure of sialic acid, bisecting N-acetylglucosamine or the like.

In the present invention, a core fucose or α1,6-fucose means a sugar structure in which 1-position of fucose is bound to 6-position of N-acetylglucosamine (hereinafter referred to as GlcNAc) in the reducing end through α-bond in the complex N-glycoside-linked sugar chain. In addition, the sugar chain in which fucose is not bound to N-acetylglucosamine in the reducing end in the complex N-glycoside-linked sugar chain is called as having no fucose or called as a sugar chain without a core fucose.

In addition, in the present invention, the core structure or tri-mannosyl core structure means Manα1-6 (Manα1-3) Manβ1-4GlcNAcβ1-4GlcNAc structure.

In the present invention, the complex-type N-glycoside-linked sugar chain is represented by the following formula:

[Chem 1]

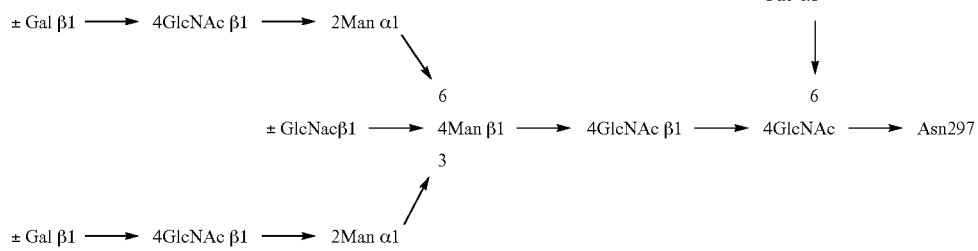

The antibody variant composition may comprise an antibody molecule having the same sugar chain structure or an antibody molecule having different sugar chain structures, so long as it is an antibody molecule in which the N-glycoside-linked sugar chain is bound to the Asn residue at position 297 in Fc region and has the above sugar chain structure.

That is, the antibody variant composition of the present invention means a composition comprising antibody variant molecules having the same or different sugar chain structure(s) (A typical complex-type sugar chain structure is shown in FIG. 1).

Furthermore, among the antibody variant compositions of the present invention, the antibody composition comprising an antibody molecule having Fc region in which a complex-type N-glycoside-linked sugar chain is bound to the Asn residue at position 297, and having sugar chains without core fucose among the total complex-type N-glycoside-linked sugar chains which bind to Fc contained in the composition, has high ADCC activity in addition to CDC activity.

As the ratio of sugar chains without core fucose antibodies having any ratio are included, so long as the ADCC activity of antibody is increased. The ratio is preferably 20% or more, more preferably 51% to 100%, still more preferably 80% to 100%, particularly preferably 90% to 99% and most preferably 100%.

In the present invention, the sugar chain without core fucose may have any sugar chain structure in the non-reducing terminal, so long as fucose is not bound to N-acetylglucosamine in the reducing terminal in the above formula.

In the present invention, the case where fucose is not bound to N-acetylglucosamine in the reducing terminal in the sugar chain (no core fucose) means that fucose is not substantially bound. An antibody composition in which fucose is not substantially bound specifically refers to an antibody composition in which fucose is not substantially detected, i.e., the content of fucose is below the detection limit, when subjected to the sugar chain analysis described in 4 below. An antibody composition in which fucose is not bound to N-acetylglucosamine in the reducing terminals of all sugar chains has highest ADCC activity.

The ratio of antibody molecules having sugar chains in which fucose is not bound to N-acetylglucosamine in the reducing terminal in the sugar chains contained in the composition which comprises an antibody molecule having complex-type N-glycoside-linked sugar chains in Fc can be determined by releasing the sugar chains from the antibody molecule using a known method such as hydrazinolysis or enzyme digestion [*Biochemical Experimentation Methods 23—Method for Studying Glycoprotein Sugar Chain* (Japan Scientific Societies Press), edited by Reiko Takahashi (1989)], carrying out fluorescence labeling or radioisotope labeling of the released sugar chains and then separating the labeled sugar chains by chromatography.

Also, the ratio of antibody molecules having sugar chains in which fucose is not bound to N-acetylglucosamine in the reducing terminal in the sugar chains contained in the composition which comprises an antibody molecule having complex-type N-glycoside-linked sugar chains in Fc region can be determined by analyzing the released sugar chains with the HPAED-PAD method [*J. Liq. Chromatogr.*, 6, 1577 (1983)].

The transformant producing the antibody variant composition of the present invention can be obtained by introducing, into an animal cell, an antibody variant composition expression vector into which DNAs encoding a variable region and a constant region of an antibody molecule are inserted.

The antibody variant expression vector is constructed as described below.

Each of the above DNAs encoding CH and CL is introduced into a vector for expression of antibody variant to produce an antibody variant composition expression vector.

The vector for expression of antibody variant includes pAGE107 (Japanese Published Unexamined Patent Application No. 22979/91; Miyaji H. et al., *Cytotechnology*, 3, 133-140 (1990)), pAGE103 (Mizukami T. and Itoh S., *J. Biochem.*, 101, 1307-1310 (1987)), pHSG274 (Brady G. et al., *Gene*, 27, 223-232 (1984)), pKCR (O'Hare K. et al., *Proc. Natl. Acad. Sci. USA*, 78, 1527-1531 (1981)), pSG1βd2-4 (Miyaji H. et al., *Cytotechnology*, 4, 173-180 (1990)) and the like.

The promoter and enhancer used as the vector for expression of antibody variant include SV40 early promoter and enhancer (Mizukami T. and Itoh S., *J. Biochem.*, 101, 1307-1310 (1987)), LTR promoter and enhancer of Moloney mouse leukemia virus (Kuwana Y. et al., *Biochem. Biophys. Res. Commun.*, 149, 960-968 (1987)), immunoglobulin H chain promoter (Mason J. O. et al., *Cell*, 41, 479-487 (1985)) and enhancer (Gillies S. D. et al., *Cell*, 33, 717-728 (1983)) and the like.

The vector for expression of antibody variant composition may be either of a type in which genes encoding the H chain and L chain exist on separate vectors or of a type in which both genes exist on the same vector (tandem type). In respect of easiness of construction of an antibody variant composition expression vector, easiness of introduction into animal cells, and balance between the expression amounts of the H and L chains of an antibody in animal cells, a tandem type of the vector for expression of antibody variant composition is more preferred (Shitara K. et al., *J. Immunol. Methods*, 167, 271-278 (1994)).

The tandem type vector for expression of the antibody variant composition includes pKANTEX93 (WO97/10354), pEE18 (Bentley K. J. et al., *Hybridoma*, 17, 559-567 (1998)) and the like.

cDNAs encoding VH and VL of antibodies for various antigens are cloned into the upstream of DNAs encoding CH and CL of the constructed vector for expression of the antibody variant composition to thereby construct the antibody variant composition expression vector.

A method for introducing the expression vector into a host cell includes electroporation (Japanese Published Unexamined Patent Application No. 257891-90; Miyaji H. et al., *Cytotechnology*, 3, 133-140 (1990)) and the like.

The host cell producing the antibody variant composition of the present invention may be any host cell which is generally used in production of a recombinant protein, such as an animal cell, a plant cell or a microorganism.

The host cell producing the antibody variant composition of the present invention includes a CHO cell derived from a Chinese hamster ovary tissue, a rat myeloma cell line YB2/3HL.P2.G11.16Ag.20 cell, a mouse myeloma cell line NS0 cell, a mouse myeloma SP2/0-Ag14 cell, a BHK cell derived from a Syrian hamster kidney tissue, a human leukemia cell line Namalwa cell, a PER.C6 cell derived from human retinoblastoma, a HEK 293 cell derived from embryonic kidney tissue, an NM-F9 cell derived from human myeloid leukemia, an embryonic stem cell, a fertilized egg cell and the like.

As the host cell, a host cell for producing a pharmaceutical composition comprising a recombinant glycoprotein, an embryonic stem cell or fertilized egg cell for producing a non-human transgenic animal which produces a pharmaceutical composition comprising a recombinant glycoprotein, a plant cell for producing a transgenic plant which produces a pharmaceutical composition comprising a recombinant glycoprotein and the like are preferable.

Examples of the parent cell include a cell in which a genomic gene of an enzyme relating to synthesis of GDP-L-fucose, an enzyme relating to sugar chain modification of a core fucose in the reducing end of the complex-type N-glycoside-linked sugar chain, or a protein relating to transport of GDP-L-fucose to the Golgi body is modified or a cell before carrying out gene modification. For example, the following cells are preferable.

A parent cell of the NS0 cell includes NS0 cells disclosed in the references such as *BIO/TECHNOLOGY*, 10, 169 (1992); and *Biotechnol. Bioeng.*, 73, 261 (2001). In addition, examples include NS0 cell line (RCB0213) which is registered in Riken Cell Bank or a substrain prepared by adapting these cells in various serum free medium.

A parent cell of the SP2/0-Ag14 cell include SP2/0-Ag14 cell disclosed in the references such as *J. Immunol.*, 126, 317 (1981), *Nature*, 276, 269 (1978) and *Human Antibodies and Hybridomas*, 3, 129 (1992). In addition, examples include SP2/0-Ag14 cell (ATCC CRL-1581) which is registered in ATCC or a substrain (such as ATCC CRL-1581.1) prepared by adapting these cells in various serum free medium.

A parent cell of the CHO cell derived from a Chinese hamster ovary tissue include CHO cell disclosed in the references such as *Journal of Experimental Medicine*, 108, 945 (1958), *Proc. Natl. Acad. Sci. USA*, 60, 1275 (1968), *Genetics*, 55, 513 (1968), *Chromosoma*, 41, 129 (1973), *Methods in Cell Science*, 18, 115 (1996), *Radiation Research*, 148, 260 (1997), *Proc. Natl. Acad. Sci. USA*, 77, 4216 (1980), *Proc. Natl. Acad. Sci. USA*, 60, 1275 (1968), *Cell*, 6, 121 (1975), *Molecular Cell Genetics*, Appendix I, II (p 883-900).

In addition, examples include CHO-K1 cell (ATCC CCL-61) which is registered in ATCC, DUXB11 cell (ATCC CRL-9096), Pro-5 cell (ATCC CRL-1781) and commercially available CHO-S cell (manufactured by Lifetechnologies; Cat#11619) or a substrain prepared by adapting these cells in various serum free medium.

A parent cell of the rat myeloma cell line YB2/3HL.P2.G11.16Ag.20 cell include a cell line established using a Y3/Ag1.2.3 cell (ATCC CRL-1631). Specific examples include the YB2/3HL.P2.G11.16Ag.20 cells disclosed in the references such as *J. Cell. Biol.*, 93, 576 (1982), *Methods Enzymol.*, 73B, 1 (1981). In addition, examples include YB2/3HL.P2.G11.16Ag.20 cell (ATCC CRL-1662) which is registered in ATCC or a substrain prepared by adapting these cells in various serum free medium.

The host cell capable of expressing an antibody variant composition having high ADCC activity as well as high CDC activity includes a host cell resistant to a lectin which recognizes a core fucose, such as a host cell capable of producing an antibody composition comprising an antibody molecule having complex-type N-glycoside-linked sugar chains in the Fc region, wherein the ratio of sugar chains in which fucose is not bound to N-acetylglucosamine in the reducing terminal of the sugar chains among the total complex-type N-glycoside-linked sugar chains which bind to the Fc region contained in the composition is 20% or more. Examples include cells in which activity of at least one protein described in the following (a) to (c) is decreased or deleted, and the like:

(a) an enzyme relating to synthesis of an intracellular sugar nucleotide, GDP-L-fucose; GDP-mannose 4,6-dehydratase (GMD), Fx, GDP-beta-L-fucose pyrophosphorylase (GFPP) and fucokinase;
(b) an enzyme relating to the modification of a sugar chain in which 1-position of fucose is bound to 6-position of N-acetylglucosamine in the reducing terminal through α-bond in a complex-type N-glycoside-linked sugar chain; α1,6-fucosyltransferase (FUT8);
(c) a protein relating to transport of GDP-L-fucose to the Golgi body; GDP-L-fucose transporter.

In addition, examples include an enzyme or a transporter protein having at least 80% or more identity, preferably 85% or more identity, more preferably 90% or more identity, still more preferably 95% or more identity, particularly preferably 97% or more identity, and most preferably 99% or more identity when the amino acid sequence of it is compared with these enzymes or the transporter protein and calculated using an analysis soft such as BLAST [*J. Mol. Biol.*, 215, 403 (1990)] or FASTA [*Methods in Enzymology*, 183, 63 (1990)], and having an activity of the enzyme or the transporter.

Specific examples of the above host cell producing the antibody variants of the present invention include a CHO cell in which a gene encoding α1,6-fucosyltransferase (FUT8) is knocked out; a CHO cell in which a gene encoding GDP-mannose 4,6-dehydratase (GMD) is knocked out; a CHO cell in which a gene encoding GDP-L-fucose transporter is knocked out; and the like (WO02/31140, WO03/85107).

The method for obtaining a cell in which the above enzyme activity is decreased or deleted may by any method, so long as it is a method for decreasing or deleting the objective enzyme activity. Examples include the following (a) to (e):
(a) gene disruption targeting at a gene encoding the enzyme;
(b) introduction of a dominant-negative mutant of a gene encoding the enzyme;
(c) introduction of a mutation into the enzyme;
(d) suppression of transcription or translation of a gene encoding the enzyme;
(e) selection of a cell line resistant to a lectin which recognizes a sugar chain structure in which 1-position of fucose is bound to 6-position of N-acetylglucosamine in the reducing terminal through α-bond in a N-glycoside-linked sugar chain; and the like.

As the lectin which recognizes a sugar chain structure in which 1-position of fucose is bound to 6-position of N-acetylglucosamine in the reducing terminal through α-bond in a N-glycoside-linked sugar chain, any lectin capable of recognizing the sugar chain structure can be used. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*), Aleuria aurantia lectin AAL (lectin derived from *Aleuria aurantia*) and the like.

The "cell resistant to a lectin" refers to a cell in which growth is not inhibited by the presence of a lectin at an effective concentration. The "effective concentration" is a concentration higher than the concentration that does not allow the normal growth of a cell prior to the genome modification (hereinafter referred to also as parent cell line), preferably equal to the concentration that does not allow the normal growth of a cell prior to the genome modification, more preferably 2 to 5 times, further preferably 10 times, most preferably 20 or more times the concentration that does not allow the normal growth of a cell prior to the modification of the genomic gene.

The effective concentration of lectin that does not inhibit growth may be appropriately determined according to each cell line. It is usually 10 μg/ml to 10 mg/ml, preferably 0.5 mg/ml to 2.0 mg/ml.

The transgenic animal used in the present invention include a transgenic animal in which a genome gene is modified so as to delete the activity of an enzyme relating to synthesis of GDP-L-fucose, an enzyme relating to modification of a core fucose of a sugar chain in a complex-type N-glycoside-linked sugar chain or a protein relating to transport of GDP-L-fucose to the Golgi body; and the like.

Specific examples include a transgenic animal in which a gene encoding α1,6-fucosyltransferase is knocked out, a transgenic animal in which a gene encoding GDP-mannose 4,6-dehydratase is knocked out, a transgenic animal in which a gene encoding GDP-L-fucose transporter is knocked out.

The antibody variant of the present invention includes an antibody conjugate in which a radioisotope, an agent having a low molecular weight, an agent having a high molecular weight, a protein or a therapeutic antibody is bound to the antibody variant or the fragment thereof chemically or using genetic engineering method.

In addition, the antibody variant composition of the present invention may be a pharmaceutical composition in which the antibody variant of the present invention and the following therapeutic agent such as an agent having a low molecular weight, an agent having a high molecular weight, an immunostimulator and cytokine are administered simultaneously or sequentially, or a combination drug prepared by mixing each pharmaceutical component. The combination drug prepared by mixing each pharmaceutical component comprising a fusion antibody in which at least one agent is bound to the antibody variant or the antibody fragment thereof of the present invention.

In addition, after a pharmaceutical kit comprising each agent is prepared, these agents may be administered to a patient simultaneously or sequentially, or be administered after mixing these agents.

The antibody conjugate of the present invention can be produced by chemically conjugating a radioisotope, an agent having a low molecular weight, an agent having a high molecular weight, an immunostimulator, a protein, a therapeutic antibody or the like to the N-terminal side or C-terminal side of an H chain or an L chain of the antibody variant or the antibody fragment thereof of the present invention, an appropriate substituent or side chain of the antibody or the antibody fragment thereof of the present invention, further a sugar chain in the antibody or the antibody fragment or the like [*Antibody Engineering Handbook*, published by Chijin Shokan (1994)].

Also, the antibody conjugate can be genetically produced by linking a DNA encoding the antibody variant or the antibody fragment thereof of the present invention to other DNA encoding a protein or a therapeutic antibody to be conjugated, inserting the DNA into a vector for expression, and introducing the expression vector into an appropriate host cell.

The radioisotope includes $^{111}$I, $^{131}$I, $^{125}$I, $^{90}$Y, $^{64}$Cu, $^{99}$Tc, $^{77}$Lu, $^{153}$Sm, $^{186}$Re, $^{188}$Re, $^{211}$At, $^{212}$Bi and the like. The radioisotope can directly be conjugated with the antibody by Chloramine-T method or the like. Also, a substance chelating the radioisotope can be conjugated with the antibody.

The chelating agent includes 1-isothiocyanatobenzyl-3-methyldiethylene-triaminepentaacetic acid (MX-DTPA) and the like.

The agent having a low molecular weight includes an anti-tumor agent such as an alkylating agent, a nitrosourea agent, a metabolism antagonist, an antibiotic substance, an alkaloid derived from a plant, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor [*Rinsho Syuyo-gaku* (Clinical Oncology), Gan to Kagaguryoho-Sha (1996)], a steroid agent such as hydrocortisone and prednisone, a nonsteroidal agent such as aspirin and indomethacin, immune-regulating agent such as aurothiomalate, penicillamine, immuno-suppressing agent such as cyclophosphamide and azathioprine, anti-inflammatory agent such as anti-histamine agent, for example, chlorpheniramine maleate and clemastine [*Ensho to Kouensho-Ryoho* (Inflammation and Anti-inflammation Therapy), Ishiyaku Shuppann (1982)] and the like.

Examples of the antitumor agent include amifostine (Ethyol), cisplatin, dacarbazine (DTIC), dactinomycin, mecloretamin (nitrogen mustard), streptozocin, cyclophosphamide, iphosphamide, carmustine (BCNU), lomustine (CCNU), doxorubicin (adriamycin), epirubicin, gemcitabine (Gemsal), daunorubicin, procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotea), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, iphosphamide, idarubicin, mesna, irinotecan (CPT-11), nogitecan, mitoxantrone, topotecan, leuprolide, megestrol, melfalan, mercaptopurine, hydroxycarbamide, plicamycin, mitotane, pegasparagase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI 571), elrotinib, FMS-like tyrosine kinase 3 (Flt3) inhibitor, vascular endothelial growth facotr receptor (VEGFR) inhibitor, fibroblast growth factor receptor (FGFR) inhibitor, epidermal growth factor receptor (EGFR) inhibitor such as Iressa and Tarceva, radicicol, 17-allylamino-17-demethoxygeldanamycin, rapamycin, amsacrine, all-trans-retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestin substances, estrogen substances, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, voltezomib, allopurinol, calicheamicin, ibritumomab tiuxetan, Targretin, ozogamine, clarithromycin, leucovorin, ifosfamide, ketoconazole, aminoglutethimide, suramin, methotrexate, maytansinoid DM1, maytansinoid DM4 and derivatives thereof, and the like.

The method for conjugating the agent having low molecular weight with the antibody includes a method in which the agent and an amino group of the antibody are conjugated through glutaraldehyde, a method in which an amino group of the agent and a carboxyl group of the antibody are conjugated through water-soluble carbodiimide, and the like.

The agent having a high molecular weight includes polyethylene glycol (hereinafter referred to as "PEG"), albumin, dextran, polyoxyethylene, styrene-maleic acid copolymer, polyvinylpyrrolidone, pyran copolymer, hydroxypropylmethacrylamide, and the like.

By binding these compounds having a high molecular weight to an antibody or antibody fragment, the following effects are expected: (1) improvement of stability against various chemical, physical or biological factors, (2) remarkable prolongation of half life in blood, (3) disappearance of immunogenicity, suppression of antibody production, and the like [*Bioconjugate Drug*, Hirokawa Shoten (1993)].

For example, the method for binding PEG to an antibody includes a method in which an antibody is allowed to react with a PEG-modifying reagent [*Bioconjugate Drug*, Hirokawa Shoten (1993)].

The PEG-modifying reagent includes a modifying agent of s-amino group of lysine (Japanese Published Unexamined Patent Application No. 178926/86), a modifying agent of a carboxyl group of aspartic acid and glutamic acid (Japanese Published Unexamined Patent Application No. 23587/81), a modifying agent of a guanidino group of arginine (Japanese Published Unexamined Patent Application No. 117920/90) and the like.

The immunostimulator may be any natural products known as immunoadjuvants. Examples of an agent enhancing immunogen include $\beta(1\rightarrow3)$glucan (lentinan, schizophyllan), $\alpha$-galactosylceramide and the like.

The protein includes a cytokine or a growth factor which activates an immunocompetent cell, such as NK cell, macrophage or neutrophil, a toxic protein, and the like.

Examples of the cytokine or the growth factor include interferon (hereinafter referred to as "INF")-$\alpha$, INF-$\beta$, INF-$\gamma$, interleukin (hereinafter referred to as "IL")-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF), Fas ligand (FasL), TRAIL ligand (Apo2L) and the like.

The toxic protein includes ricin, diphtheria toxin, attenuated diphtheria toxin, CRM197, ONTAK and the like, and also includes a toxic protein wherein mutation is introduced into a protein in order to control the toxicity.

The therapeutic antibody includes an antibody against an antigen in which apoptosis is induced by binding of the antibody, an antibody against an antigen participating in formation of pathologic state of tumor, an antibody which regulates immunological function and an antibody relating to angiogenesis in the pathologic part.

The antigen in which apoptosis is induced by binding of the antibody includes cluster of differentiation (hereinafter "CD") 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, epidermal growth factor receptor (EGFR) and the like.

The antigen participating in formation of pathologic state of tumor or the antigen for the antibody which regulates immunological function includes CD40, CD40 ligand, 137 family molecule (CD80, CD86, CD274, B7-DC, B7-H2, B7-H3, B7-H4), ligand of B7 family molecule (CD28, CTLA-4, ICOS, PD-1, BTLA), OX-40, OX-40 ligand, CD137, tumor necrosis factor (TNF) receptor family molecule (DR4, DR5, TNFR1, TNFR2), TNF-related apoptosis-inducing ligand receptor (TRAIL) family molecule, receptor family of TRAIL family molecule (TRAIL-R1, TRAIL-R2, TRAIL-R3, TRAIL-R4), receptor activator of nuclear factor kappa B ligand (RANK), RANK ligand, CD25, folic acid receptor 4, cytokine [IL-1$\alpha$, IL-1$\beta$, IL-4, IL-5, IL-6, IL-10, IL-13, transforming growth factor (TGF) $\beta$, TNF$\alpha$, etc.], receptors of these cytokines, chemokine (SLC, ELC, 1-309, TARC, MDC, CTACK, etc.) and receptors of these chemokines.

The antigen for the antibody which inhibits angiogenesis in the pathologic part includes vascular endothelial growth factor (VEGF), angiopoietin, fibroblast growth factor (FGF), EGF, platelet-derived growth factor (PDGF), insulin-like growth factor (IGF), erythropoietin (EPO), TGF$\beta$, IL-8, Ephrin, SDF-1; and receptors thereof; and the like.

An antibody conjugate with a protein or therapeutic antibody can be produced by linking a cDNA encoding a monoclonal antibody or antibody fragment to a cDNA encoding the protein, constructing a DNA encoding the fusion antibody, inserting the DNA into an expression vector for prokaryote or eukaryote, and then introducing the expression vector into a prokaryote or eukaryote to express the antibody conjugate.

In the case where the above antibody conjugate is used for the detection method, method for quantitative determination, detection reagent, reagent for quantitative determination or diagnostic agent in the present invention, examples of the agent to which the antibody variant or the antibody fragment thereof includes a label used in routine immunological detecting or measuring method.

The label includes enzymes such as alkaline phosphatase, peroxidase and luciferase, luminescent materials such as acridinium ester and lophine, fluorescent materials such as fluorescein isothiocyanate (FITC) and tetramethyl rhodamine isothiocyanate (RITC), and the like.

The antibody variant of the present invention can be a therapeutic agent for any disease as long as antigens specifically bound by the antibodies are expressed in diseases. The therapeutic agent for the above-mentioned cancers, autoimmune diseases, allergic diseases, inflammatory diseases, cardiovascular diseases, or diseases in which an antigen relating to infection with a virus or microorganism is expressed is preferable.

The antibody variant of the present invention is effective for a treatment of a causal cell of a cancer, an autoimmune disease or the like since the antibody does not have unnecessary binding of sugar chain to Fc region and have a high effector activity.

Example of the cancers include, blood cancer, head and neck cancer, glioma, tongue cancer, laryngeal cancer, esophageal cancer, gastric cancer, pancreatic cancer (such as pancreatic head cancer, pancreatic body cancer, pancreatic tail cancer and pancreatic ductal cancer), small intestine cancer, colon cancer lung cancer (such as small cell lung cancer, large cell lung cancer, adenocarcinoma and squamous cell carcinoma), mesothelioma, liver cancer, gallbladder cancer, bile duct cancer, kidney cancer, uterine cancer (such as cervical cancer and endometrial cancer), ovarian cancer, ovarian germ cell tumors, prostate cancer, bladder cancer, osteosarcoma, skin cancer, fungal diseases fungoides, Ewing sarcoma, malignant bone tumor, melanoma and the like.

Examples of the blood cancers include leukemia, chronic myelogenous leukemia, acute myeloid leukemia, chronic lymphocytic leukemia, acute lymphocytic leukemia, T cell-derived cancer and the like. Specific examples include cutaneous T cell lymphoma (CTCL), peripheral T-cell lymphoma (PTCL), anaplastic large cell lymphoma (ALCL), acute lymphocytic leukemia (ALL), multiple myeloma, Hodgkin's lymphoma, or non-Hodgkin's lymphoma (such as Burkitt lymphoma, lymphoblastic lymphoma, diffuse large B-cell lymphoma, anaplastic large cell lymphoma, MANTL lymphoma and follicular lymphoma), and the like.

Examples of the autoimmune diseases include Hashimoto's disease, Graves' disease, idiopathic thrombocytopenic purpura, idiopathic neutropenia, megaloblastic anemia, hemolytic anemia, myasthenia gravis, psoriasis, pemphigus, pemphigoid, Crohn's disease, ulcerative colitis, ankylosing spondylitis, multiple sclerosis, type I diabetes, hepatitis, myocarditis, Sjogren's syndrome, rheumatoid arthritis, systemic lupus erythematosus (SLE), antiphospholipid antibody syndrome, polymyositis, dermatomyositis, cutaneous systemic sclerosis, post-transplant rejection and the like.

Examples of the allergic diseases include acute or chronic airway hyperresponsiveness, bronchial asthma, atopic dermatitis, allergic rhinitis and the like.

Processes for producing the antibody variant composition of the present invention are described below in detail.

1. Process for Producing Antibody Variant Composition

The antibody variant composition of the present invention can be obtained, for example, by expressing it in a host cell using the methods described in *Molecular Cloning*, Second Edition; *Current Protocols in Molecular Biology; Antibodies, A Laboratory manual*, Cold Spring Harbor Laboratory, 1988 (hereinafter referred to as *Antibodies*); *Monoclonal Antibodies: principles and practice*, Third Edition, Acad. Press 1993 (hereinafter referred to as *Monoclonal Antibodies*); *Antibody Engineering, A Practical Approach*, IRL Press at Oxford University Press, 1996 (hereinafter referred to as *Antibody Engineering*); and the like, for example, in the following manner.

(1) Construction of an Antibody Variant Composition Expression Vector of the Present Invention The antibody variant composition expression vector of the present invention is an expression vector for animal cell into which genes encoding H chain and L chain constant regions of the antibody molecule contained in the antibody variant composition of the present invention are introduced.

The vector for expression of the antibody variant composition can be constructed by cloning each of the genes encoding H chain and L chain constant regions of the antibody molecule contained in the antibody variant composition into a vector for expression of animal cell.

The gene encoding the H chain constant region of an antibody molecule contained in the antibody variant composition of the present invention can be produced by cloning genes encoding the H chain constant regions of IgG1 antibody and then ligating gene fragments encoding desired amino acid sequences.

Also, the total DNA can be synthesized by using synthetic DNAs and synthesis using PCR can also be carried out (*Molecular Cloning*, Second Edition). Furthermore, it can be produced by combining these techniques.

In the present invention, in the amino acid residues of the sequence of Asn-X-Ser/Thr (X is an amino acid other than proline) at positions other than positions 297 to 299 according to the EU index in the Fc region of a human IgG antibody, an amino acid residue to be substituted with any amino acid residue of Asn, X, and Ser/Thr can be determined by taking into consideration the amino acid sequence of the N terminal or C terminal of the N-glycoside-linked sugar chain consensus sequence.

Namely, an appropriate amino acid substitution can be carried out after considering a site for the amino acid substitution and an amino acid residue after substitution so that new N-glycoside-linked sugar chain consensus sequence is not generated as the result of amino acid substitutions. In the present invention, specifically, design can be determined in the following manner.

In the Fc region of a human antibody (SEQ ID NO:1), examples of the N-linked sugar chain consensus sequence at positions other than positions 297 to 299 according to the EU index include Asn-Thr-Thr at positions 392 to 394. The amino acid sequence of back and forth position thereof is Asn389-Asn390-Tyr391-Asn392-Thr393-Thr394-Pro395-Pro396 (see FIG. 4).

When the amino acid substitution of Asn392 to Ser/Thr is carried out, a new consensus sequence 390Asn-391Tyr-392Ser/Thr would be generated since Asn exists at position 390. Therefore, Asn392 is preferably substituted with an amino acid residue selected from Gly, Ala, Val, Leu, Ile, Met, Pro, Asp, Gln, Glu, Lys, Arg, His, Phe, Tyr and Trp. In addition, Thr393 is preferably substituted with Pro, and 394Thr is preferably substituted with an amino acid residue other than Ser/Thr.

Accordingly, appropriate substitution site of amino acid substitution and appropriate amino acid residue can be determined by considering amino acid residues (1 to 3 residues) which exist near the N-glycoside-linked sugar chain consensus sequence and design the amino acid sequence after amino acid substitutions.

The expression vector for animal cell may by any vector, so long as the above gene encoding the constant region of an antibody molecule can be introduced and expressed. Examples include pKANTEX93 [*Mol. Immunol.*, 37, 1035 (2000)], pAGE107 [*Cytotechnology*, 3, 133 (1990), pAGE103 [*J. Biochem.*, 101, 1307 (1987)], pHSG274 [*Gene*, 27, 223 (1984)], pKCR [*Proc. Natl. Acad. Sci. U.S.A.*, 78, 1527 (1981)], pSG1βd2-4 [*Cytotechnology*, 4, 173 (1990)] and the like.

The promoter and enhancer used for the expression vector for animal cell include SV40 early promoter and enhancer [*J. Biochem.*, 101, 1307 (1987)], LTR of Moloney mouse leukemia virus [*Biochem. Biophys. Res. Commun.*, 149, 960 (1987)], immunoglobulin H chain promoter [*Cell*, 41, 479 (1985)] and enhancer [*Cell*, 33, 717 (1983)] and the like.

The vector for expression of the antibody variant composition of the present invention may be either of a type in which genes encoding the H chain and L chain of antibody, respectively, are present on separate vectors or of a type in which both genes exist on the same vector (hereinafter referred to as tandem type). In respect of easiness of construction of the antibody variant composition expression vector of the present invention, easiness of introduction into animal cells, and balance between the expression amounts of the H and L chains of the antibody in animal cells, a tandem type of the vector for expression of the antibody variant composition is more preferred (*J. Immunol. Methods*, 167, 271 (1994)).

The constructed antibody variant composition expression vector of the present invention can be used for expression of the human chimeric antibody, the humanized antibody and the human antibody in animal cells.

(2) Obtaining of cDNA Encoding V Region of Non-Human Animal Antibody cDNAs encoding an H chain variable region (hereinafter referred to as "VH") and an L chain variable region (hereinafter referred to as "VL") of a non-human animal antibody such as a mouse antibody can be obtained in the following manner.

A cDNA is synthesized by using mRNA extracted from a hybridoma cell which produces any antibody as a template. The synthesized cDNA is cloned into a vector such as a phage or a plasmid to obtain a cDNA library.

Each of a recombinant phage or recombinant plasmid comprising a cDNA encoding VH and a recombinant phage or recombinant plasmid comprising a cDNA encoding the L chain V region is isolated from the above library by using cDNA encoding C region or V region of a known mouse antibody as the probe.

Full length nucleotide sequences of VH and VL of the mouse antibody of interest on the recombinant phage or recombinant plasmid are determined, and full length amino acid sequences of VH and VL are deduced from the nucleotide sequences.

Hybridoma cells producing any non-human animal-derived antibody can be obtained by immunizing a non-human animal with an antigen bound to the antibody, preparing hybridomas from antibody-producing cells of the immunized animal and myeloma cells according to a known method [*Molecular Cloning, Second Edition; Current Protocols in Molecular Biology; Antibodies, A Laboratory manual*, Cold Spring Harbor Laboratory, 1988 (hereinafter referred to as *Antibodies*); *Monoclonal Antibodies: principles and practice*, Third Edition, Acad. Press 1993 (hereinafter referred to as *Monoclonal Antibodies*), *Antibody Engineering, A Practical Approach*, IRL Press at Oxford University Press, 1996 (hereinafter referred to as *Antibody Engineering*)], selecting cloned hybridomas, culturing the selected hybridomas and purifying cells from the culture supernatant.

As the non-human animal, any animal can be used so long as hybridoma cells can be prepared from the animal. Suitable animals include mouse, rat, hamster and rabbit.

The methods for preparing total RNA from a hybridoma cell include the guanidine thiocyanate-cesium trifluoroacetate method [*Methods in Enzymol.*, 154, 3 (1987)] and RNeasy kit (manufactured by QIAGEN).

The methods for preparing mRNA from the total RNA include the oligo (dT) immobilized cellulose column method [*Molecular Cloning, A Laboratory Manual*, Cold Spring Harbor Lab. Press 1989].

Examples of the kits for preparing mRNA from a hybridoma cell include Fast Track mRNA Isolation Kit (manufactured by Invitrogen) and Quick Prep mRNA Purification Kit (manufactured by Pharmacia).

The methods for synthesizing the cDNA and preparing the cDNA library include conventional methods [*Molecular Cloning, A Laboratory Manual*, Cold Spring Harbor Lab. Press (1989), *Current Protocols in Molecular Biology*, Supplement 1-34], or methods using commercially available kits.

Examples of the commercially available kits include SuperScript (registered trade name) Plasmid System for cDNA Synthesis and Plasmid Cloning (manufactured by GIBCO BRL) and ZAP-cDNA Synthesis Kit (manufactured by Stratagene).

In preparing the cDNA library, the vector for integrating the cDNA synthesized using the mRNA extracted from a hybridoma cell as a template may be any vector so long as the cDNA can be integrated.

Examples of suitable vectors include ZAP Express [*Strategies*, 5, 58 (1992)], pBluescript II SK(+) [*Nucleic Acids Research*, 17, 9494 (1989)], λZAP II (manufactured by STRATAGENE), λgt10, λgt11 [*DNA Cloning: A Practical Approach*, I, 49 (1985)], Lambda BlueMid (manufactured by Clontech), λExCell, pT7T3 18U (manufactured by Pharmacia), pcD2 [*Mol. Cell. Biol.*, 3, 280 (1983)], pUC18 [*Gene*, 33, 103 (1985)] and the like.

As *Escherichia coli* for introducing the cDNA library constructed with a phage or plasmid vector, any *Escherichia coli* can be used so long as the cDNA library can be introduced, expressed and maintained.

Examples of suitable *Escherichia coli* include XL1-Blue MRF' [*Strategies*, 5, 81 (1992)], C600 [*Genetics*, 39, 440 (1954)], Y1088, Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

The methods for selecting the cDNA clones encoding VH and VL of a non-human animal-derived antibody from the cDNA library include colony hybridization or plaque hybridization [*Molecular Cloning, A Laboratory Manual*, Cold Spring Harbor Laboratory Press New York, 1989] using an isotope- or fluorescence-labeled probe.

It is also possible to prepare the cDNAs encoding VH and VL by preparing primers and carrying out PCR [*Molecular Cloning, A Laboratory Manual*, Cold Spring Harbor Laboratory Press New York (1989), *Current Protocols in Molecular Biology*, Supplement 1-34] using the cDNA or cDNA library as a template.

The nucleotide sequences of the cDNAs selected by the above methods can be determined by cleaving the cDNAs with appropriate restriction enzymes, cloning the fragments into a plasmid such as pBluescript SK(-) (manufactured by STRATAGENE), and then analyzing the sequences by generally employed nucleotide sequence analyzing methods such as the dideoxy method of Sanger, et al. [*Proc. Natl. Acad. Sci. USA*, 74, 5463 (1977)] or by use of nucleotide sequence analyzers such as ABI PRISM 377 DNA Sequencer (manufactured by Applied Biosystems).

The full length of amino acid sequences of VH and VL are deduced from the determined nucleotide sequences and compared with the full length of amino acid sequences of VH and VL of a known antibody [*Sequences of Proteins of Immunological Interest*, US Dept. Health and Human Services (1991)], whereby it can be confirmed that the obtained cDNAs encode amino acid sequences which completely comprise VH and VL of the antibody including secretory signal sequences.

Further, when the amino acid sequence of an antibody variable region or the nucleotide sequence of DNA encoding the variable region is already known, the DNA can be obtained by the following methods.

When the amino acid sequence is known, the DNA can be obtained by designing a DNA sequence encoding the variable region taking into consideration the frequency of codon usage [*Sequences of Proteins of Immunological Interest*, US Dept. Health and Human Services (1991)], synthesizing several synthetic DNAs constituting approximately 100-150 nucleotides based on the designed DNA sequence, and carrying out PCR using the synthetic DNAs or synthesizing complete length of DNA sequence. When the nucleotide sequence is known, the DNA can be obtained by same method described in the above.

(3) Analysis of the Amino Acid Sequence of the V Region of an Antibody from a Non-Human Animal By comparing the full length of amino acid sequences of VH and VL of the antibody including secretory signal sequences with the amino acid sequences of VH and VL of a known antibody [*Sequences of Proteins of Immunological Interest*, US Dept. Health and Human Services (1991)], it is possible to deduce the length of the secretory signal sequences and the N-terminal amino acid sequences and further to know the subgroup to which the antibody belongs. In addition, the amino acid sequences of CDRs of VH and VL can be deduced in a similar manner.

(4) Construction of a Human Chimeric Antibody Expression Vector

A human chimeric antibody expression vector can be constructed by inserting the cDNAs encoding VH and VL of the antibody of a non-human animal into sites upstream of the genes encoding CH and CL of the human antibody in the vector for expression of antibody variant composition described in the above 1 (1).

For example, the human chimeric antibody expression vector can be constructed by ligating the cDNAs encoding VH and VL of the antibody of a non-human animal respectively to synthetic DNAs comprising the 3'-terminal nucleotide sequences of VH and VL of an antibody of a non-human animal and the 5'-terminal nucleotide sequences of CH and CL of a human antibody and also having recognition sequences for appropriate restriction enzymes at both ends, and inserting them into sites upstream of the genes encoding CH and CL of the human antibody in the vector for expression of antibody variant composition described in the above 1 (1) so as to express them in an appropriate form.

(5) Construction of cDNA Encoding V Region of a Humanized Antibody cDNAs encoding VH and VL of the humanized antibody can be constructed in the following manner. First, amino acid sequences of FRs of VH and VL of the human antibody for grafting CDRs of VH and VL of the non-human animal-derived antibody are selected.

The amino acid sequences of FRs of VH and VL of the human antibody may be any of those from human antibodies. Suitable sequences include the amino acid sequences of FRs of VHs and VLs of human antibodies registered at databases such as Protein Data Bank, and the amino acid sequences common to subgroups of FRs of VHs and VLs of human antibodies [*Sequences of Proteins of Immunological Interest*, US Dept. Health and Human Services, 1991].

In order to prepare the humanized antibody having a sufficient activity among these, it is preferred to select amino acid sequences having a homology of as high as possible (at least 60% or more) with the amino acid sequences of FRs of VH and VL of the desired non-human animal-derived antibody.

Next, the amino acid sequences of CDRs of VH and VL of the desired non-human animal-derived antibody are grafted to the selected amino acid sequences of FRs of VH and VL of the human antibody to design amino acid sequences of VH and VL of the humanized antibody. The designed amino acid sequences are converted into DNA sequences taking into consideration the frequency of codon usage in the nucleotide sequences of antibody genes [*Sequences of Proteins of Immunological Interest*, US Dept. Health and Human Services, 1991], and DNA sequences encoding the amino acid sequences of VH and VL of the humanized antibody are designed. The designed DNA sequences are fully synthesized.

Cloning into the vector for expression of the recombinant antibody composition of the present invention constructed in the above 1 (1) can be easily carried out by introducing recognition sequences for appropriate restriction enzymes to the 5'-terminals of synthetic DNAs present on both ends. After the PCR, the amplification products are cloned into a plasmid such as pBluescript SK(–) (manufactured by STRATAGENE) and the nucleotide sequences are determined by the method described in the above 1 (2) to obtain a plasmid carrying DNA sequences encoding the amino acid sequences of VH and VL of the desired humanized antibody.

(6) Substitution of the Amino Acid Sequence of V Region of a Humanized Antibody

It is known that a humanized antibody prepared merely by grafting CDRs of VH and VL of a non-human animal-derived antibody to FRs of VH and VL of a human antibody has a lower antigen-binding activity compared with the original non-human animal-derived antibody [*BIO/TECHNOLOGY*, 9, 266 (1991)].

This is probably because in VH and VL of the original non-human animal-derived antibody, not only CDRs but also some of the amino acid residues in FRs are involved directly or indirectly in the antigen-binding activity, and such amino acid residues are substituted with amino acid residues of FRs of VH and VL of the human antibody by CDR grafting.

In order to solve this problem, attempts have been made in the preparation of a humanized antibody to raise the lowered antigen-binding activity by identifying the amino acid residues in the amino acid sequences of FRs of VH and VL of the human antibody which are directly relating to the binding to an antigen or which are indirectly relating to it through interaction with amino acid residues in CDRs or maintenance of the three-dimensional structure of the antibody, and modifying such amino acid residues to those derived from the original non-human animal-derived antibody [*BIO/TECHNOLOGY*, 9, 266 (1991)].

In the preparation of the humanized antibody, it is most important to efficiently identify the amino acid residues in FR which are relating to the antigen-binding activity. For the efficient identification, construction and analyses of the three-dimensional structures of antibodies have been carried out by X ray crystallography [*J. Mol. Biol.*, 112, 535 (1977)], computer modeling [*Protein Engineering*, 7, 1501 (1994)], and the like. These studies on the three-dimensional structures of antibodies have provided much information useful for the preparation of humanized antibodies However, there is no established method for preparing a humanized antibody that is adaptable to any type of antibodies. That is, at present, it is still necessary to make trial-and-error approaches, e.g., preparation of several substitutions for each antibody and examination of each substitution for the correlation with the antigen-binding activity.

Substitution of the amino acid residues in FRs of VH and VL of a human antibody can be achieved by PCR as described in the above 1 (5) using synthetic DNAs for substitution. The nucleotide sequence of the PCR amplification product is determined by the method described in the above 1 (2) to confirm that the desired substitution has been achieved.

(7) Construction of a Humanized Antibody Expression Vector

The humanized antibody expression vector can be constructed by inserting the cDNAs encoding VH and VL of the humanized antibody constructed in the above 1 (5) and (6) into sites upstream of the genes encoding CH and CL of the human antibody in the vector for expression of the antibody variant composition of the present invention described in the above 1 (1).

For example, the humanized antibody expression vector can be constructed by introducing recognition sequences for appropriate restriction enzymes to the 5'-terminals of synthetic DNAs present on both ends among the synthetic DNAs used for constructing VH and VL of the humanized antibody in the above 1 (5) and (6), and inserting them into sites upstream of the genes encoding CH and CL of the human antibody in the vector for expression of the recombinant antibody of the present invention described in the above 1 (1) so as to express them in an appropriate form.

(8) Stable Production of a Humanized Antibody

Transformants capable of stably producing the human chimeric antibody or the humanized antibody can be obtained by introducing the human chimeric antibody or humanized antibody expression vectors described in the above 1 (4) and (7) into appropriate animal cells.

Introduction of the humanized antibody expression vector into an animal cell can be carried out by electroporation [Japanese Published Unexamined Patent Application No. 257891/90; *Cytotechnology*, 3, 133 (1990)], and the like As the animal cell for introducing the human chimeric antibody or humanized antibody expression vector, any animal cell capable of producing the human chimeric antibody or the humanized antibody can be used.

Specific examples of the animal cells include mouse myeloma cell lines NS0 and SP2/0, Chinese hamster ovary cells CHO/dhfr- and CHO/DG44, rat myeloma cell lines YB2/0 and IR983F, Syrian hamster kidney-derived BHK cell, and human myeloma cell line Namalwa. Chinese hamster ovary cell CHO/DG44 and rat myeloma cell line YB2/0 are preferred.

After the introduction of the human chimeric antibody or humanized antibody expression vector, the transformant capable of stably producing the human chimeric antibody or the humanized antibody can be selected using a medium for animal cell culture containing an agent such as G418 sulfate (hereinafter referred to as G418; manufactured by SIGMA) according to the method described in Japanese Published Unexamined Patent Application No. 257891/90.

Examples of the media for animal cell culture include RPMI1640 medium (manufactured by Nissui Pharmaceutical Co., Ltd.), GIT medium (manufactured by Nihon Pharmaceutical Co., Ltd.), EX-CELL 302 medium (manufactured by JRH), IMDM medium (manufactured by GIBCO BRL), Hybridoma-SFM medium (manufactured by GIBCO BRL), and media prepared by adding various additives such as fetal calf serum (hereinafter referred to as FCS) to these media. By culturing the obtained transformant in the medium, the human chimeric antibody or the humanized antibody can be produced and accumulated in the culture supernatant.

The amount and the antigen-binding activity of the human chimeric antibody or the humanized antibody produced in the culture supernatant can be measured by enzyme-linked immunosorbent assay [hereinafter referred to as ELISA; *Antibodies: A Laboratory Manual*, Cold Spring Harbor Laboratory, Chapter 14 (1998); *Monoclonal Antibodies: Principles and Practice*, Academic Press Limited (1996)] or the like.

The amount of the human chimeric antibody or the humanized antibody to be produced by the transformant can be increased by utilizing a DHFR gene amplification system or the like according to the method described in Japanese Published Unexamined Patent Application No. 257891/90.

The human chimeric antibody or the humanized antibody can be purified from the culture supernatant of the transformant using a protein A column [*Antibodies: A Laboratory Manual*, Cold Spring Harbor Laboratory, Chapter 8 (1988); *Monoclonal Antibodies: Principles and Practice*, Academic Press Limited (1996)].

In addition, purification methods generally employed for the purification of proteins can also be used. For example, the purification can be carried out by combinations of gel filtration, ion exchange chromatography, ultrafiltration and the like.

The molecular weight of the H chain, L chain or whole antibody molecule of the purified human chimeric antibody or humanized antibody can be measured by SDS-denatured polyacrylamide gel electrophoresis [hereinafter referred to as SDS-PAGE; *Nature*, 227, 680 (1970)], Western blotting [*Antibodies: A Laboratory Manual*, Cold Spring Harbor Laboratory, Chapter 12 (1988); *Monoclonal Antibodies: Principles and Practice*, Academic Press Limited (1996)], and the like.

Shown above is the method for producing the antibody composition using an animal cell as the host. The antibody composition can also be produced using yeast, an insect cell, a plant cell, an animal individual or a plant individual by similar methods.

Accordingly, when the host cell is capable of expressing the antibody molecule, the antibody variant composition of the present invention can be produced by introducing a gene encoding the antibody into the host cell which expresses the antibody molecule, culturing the cell, and purifying the desired antibody composition from the culture.

When yeast is used as the host cell, YEP13 (ATCC 37115), YEp24 (ATCC 37051), YCp50 (ATCC 37419), and the like can be used as the expression vector.

As the promoter, any promoters capable of expressing in yeast strains can be used. Suitable promoters include promoters of genes of the glycolytic pathway such as hexosekinase, PHO5 promoter, PGK promoter, GAP promoter, ADH promoter, gal 1 promoter, gal 10 promoter, heat shock protein promoter, MFα1 promoter and CUP 1 promoter.

Examples of suitable host cells are microorganisms belonging to the genera *Saccharomyces*, *Schizosaccharomyces*, *Kluyveromyces*, *Trichosporon* and *Schwanniomyces*, and specifically, *Saccharomyces cerevisiae*, *Schizosaccharomyces pombe*, *Kluyveromyces lactis*, *Trichosporon pullulans*, *Schwanniomyces alluvius* and the like.

Introduction of the recombinant vector can be carried out by any of the methods for introducing DNA into yeast, for example, electroporation [*Methods Enzymol.*, 194, 182 (1990)], the spheroplast method [*Proc. Natl. Acad. Sci. USA*, 84, 1929 (1978)], the lithium acetate method [*J. Bacteriology*, 153, 163 (1983)] and the method described in *Proc. Natl. Acad. Sci. USA*, 75, 1929 (1978).

When an animal cell is used as the host cell, pcDNAI, pcDM8 (commercially available from Funakoshi Co., Ltd.), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840 (1987)], pcDNAI/Amp (manufactured by Invitrogen Corp.), pREP4 (manufactured by Invitrogen Corp.), pAGE103 [*J. Biochemistry*, 101, 1307 (1987)], pAGE210, and the like can be used as the expression vector.

As the promoter, any promoters capable of expressing in animal cells can be used. Suitable promoters include the promoter of IE (immediate early) gene of cytomegalovirus (CMV), SV40 early promoter, the promoter of a retrovirus, metallothionein promoter, heat shock promoter, SRα promoter, and the like. The enhancer of IE gene of human CMV may be used in combination with the promoter.

Examples of suitable host cells are human-derived Namalwa cells, monkey-derived COS cells, Chinese hamster-derived CHO cells, HBT5637 (Japanese Published Unexamined Patent Application No. 299/88), rat myeloma cells, mouse myeloma cells, cells derived from Syrian hamster kidney, embryonic stem cells, fertilized egg cells and the like.

When an insect cell is used as the host cell, the protein can be expressed by the methods described in *Current Protocols in Molecular Biology; Baculovirus Expression Vectors, A Laboratory Manual*, W.H. Freeman and Company, New York (1992); *BIO/TECHNOLOGY*, 6, 47 (1988), and the like.

That is, the expression vector and a baculovirus are cotransfected into insect cells to obtain a recombinant virus in the culture supernatant of the insect cells, and then insect cells are infected with the recombinant virus, whereby the protein can be expressed.

The gene introducing vectors useful in this method include pVL1392, pVL1393, pBlueBacIII (products of Invitrogen Corp.) and the like.

An example of the baculovirus is Autographa californica nuclear polyhedrosis virus, which is a virus infecting insects belonging to the family Barathra.

Examples of the insect cells are *Spodoptera frugiperda* ovarian cells Sf9 and Sf21 [*Current Protocols in Molecular Biology; Baculovirus Expression Vectors, A Laboratory Manual*, W.H. Freeman and Company, New York (1992)] and *Trichoplusia ni* ovarian cell High 5 (manufactured by Invitrogen Corp.).

Cotransfection of the above expression vector and the above baculovirus into insect cells for the preparation of the recombinant virus can be carried out by the calcium phosphate method (Japanese Published Unexamined Patent Application No. 227075/90), lipofection [*Proc. Natl. Acad. Sci. USA*, 84, 7413 (1987)], and the like.

When a plant cell is used as the host cell, Ti plasmid, tobacco mosaic virus vector, and the like can be used as the expression vector.

As the promoter, any promoters capable of expressing in plant cells can be used. Suitable promoters include 35S promoter of cauliflower mosaic virus (CaMV), rice actin 1 promoter, and the like.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

Introduction of the recombinant vector can be carried out by any of the methods for introducing DNA into animal cells, for example, electroporation [*Cytotechnology*, 3, 133 (1990)], the calcium phosphate method (Japanese Published Unexamined Patent Application No. 227075/90), lipofection [*Proc. Natl. Acad. USA*, 84, 7413 (1987)], the injection method (*Manipulating the Mouse Embryo, A Laboratory Manual*), the method using particle gun (gene gun) (Japanese Patent Nos. 2606856 and 2517813), the DEAE-dextran method [*Biomanual Series 4-Methods of Gene Transfer, Expression and Analysis* (Yodosha), edited by Takashi Yokota and Kenichi Arai (1994)] and the virus vector method (*Manipulating the Mouse Embryo, A Laboratory Manual*).

Expression of the gene encoding the antibody can be carried out not only by direct expression but also by secretory production, expression of a fusion protein of the Fc region and another protein, and the like according to the methods described in *Molecular Cloning*, Second Edition.

The antibody composition can be produced by culturing the transformant obtained as above in a medium, allowing the antibody molecules to produce and accumulate in the culture, and recovering them from the culture. Culturing of the transformant in a medium can be carried out by conventional methods for culturing the host cell.

For the culturing of the transformant obtained by using a eukaryote such as yeast as the host, any of natural media and synthetic media can be used insofar as it is a medium suitable for efficient culturing of the transformant which contains carbon sources, nitrogen sources, inorganic salts, and the like which can be assimilated by the host used.

As the carbon sources, any carbon sources that can be assimilated by the microorganisms can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate, calcium carbonate and the like.

Culturing is usually carried out under aerobic conditions, for example, by shaking culture or submerged spinner culture under aeration. The culturing temperature is preferably 15 to 40° C., and the culturing period is usually 16 hours to 7 days. The pH is maintained at 3.0 to 9.0 during the culturing. The pH adjustment is carried out by using an organic or inorganic acid, an alkali solution, urea, calcium carbonate, ammonia, and the like If necessary, antibiotics such as ampicillin and tetracycline may be added to the medium during the culturing.

When a microorganism transformed with a recombinant vector using an inducible promoter is cultured, an inducer may be added to the medium, if necessary. For example, in the case of a microorganism transformed with a recombinant vector using lac promoter, isopropyl-β-D-thiogalactopyranoside or the like may be added to the medium; and in the case of a microorganism transformed with a recombinant vector using trp promoter, indoleacrylic acid or the like may be added.

Culturing is usually carried out under conditions of pH 6.0 to 8.0 at 30 to 40° C. for 1 to 7 days in the presence of 5% $CO_2$.

If necessary, antibiotics such as kanamycin and penicillin may be added to the medium during the culturing.

For the culturing of the transformant obtained by using an insect cell as the host, generally employed media such as TNM-FH medium (manufactured by Pharmingen, Inc.), Sf-900 II SFM medium (manufactured by Life Technologies, Inc.), ExCell 400 and ExCell 405 (manufactured by JRH Biosciences, Inc.) and Grace's Insect Medium [*Nature*, 195, 788 (1962)] can be used as the medium.

Culturing is usually carried out under conditions of pH 6.0 to 7.0 at 25 to 30° C. for 1 to 5 days.

If necessary, antibiotics such as gentamicin may be added to the medium during the culturing.

The transformant obtained by using a plant cell as the host may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, and the like can be used as the medium.

Culturing is usually carried out under conditions of pH 5.0 to 9.0 at 20 to 40° C. for 3 to 60 days.

If necessary, antibiotics such as kanamycin and hygromycin may be added to the medium during the culturing.

As described above, the antibody composition can be produced by culturing, according to a conventional culturing method, the transformant derived from an animal cell or a plant cell and carrying an expression vector into which DNA encoding the antibody molecule has been integrated, allowing the antibody composition to form and accumulate, and recovering the antibody composition from the culture.

Expression of the gene encoding the antibody can be carried out not only by direct expression but also by secretory production, fusion protein expression, and the like according to the methods described in *Molecular Cloning*, Second Edition.

The antibody composition may be produced by intracellular expression in host cells, may be produced by extracellular secretion from host cells or may be produced on outer membranes of host cells. A desirable production method can be adopted by changing the kind of the host cells used or the structure of the antibody molecule to be produced.

When the antibody composition is produced in host cells or on outer membranes of host cells, it is possible to force the antibody composition to be secreted outside the host cells by applying the method of Paulson, et al. [*J. Biol. Chem.*, 264, 17619 (1989)], the method of Lowe, et al. [*Proc. Natl. Acad. Sci. USA,* 86, 8227 (1989); *Genes Develop.*, 4, 1288 (1990)], or the methods described in Japanese Published Unexamined Patent Application No. 336963/93, WO94/23021, and the like That is, it is possible to force the desired antibody molecule to be secreted outside the host cells by inserting DNA encoding the antibody molecule and DNA encoding a signal peptide suitable for the expression of the antibody molecule into an expression vector, introducing the expression vector into the host cells, and then expressing the antibody molecule by use of recombinant DNA techniques.

It is also possible to increase the amount of the antibody composition to be produced by utilizing a gene amplification system using a dihydrofolate reductase gene or the like according to the method described in Japanese Published Unexamined Patent Application No. 227075/90.

Further, the antibody composition can be produced using an animal individual into which a gene is introduced (non-human transgenic animal) or a plant individual into which a gene is introduced (transgenic plant) constructed by redifferentiating the animal or plant cells into which genes are introduced.

When the transformant is an animal individual or plant individual, the antibody composition can be produced by rearing or cultivating the animal or plant in a usual manner, allowing the antibody composition to form and accumulate therein, and collecting the antibody composition from the animal individual or plant individual.

Production of the antibody composition using an animal individual can be carried out, for example, by producing the desired antibody composition in an animal constructed by introducing the gene according to known methods [*American Journal of Clinical Nutrition,* 63, 639S (1996); *American Journal of Clinical Nutrition,* 63, 627S (1996); *Bio/Technology,* 9, 830 (1991)].

In the case of an animal individual, the antibody composition can be produced, for example, by raising a non-human transgenic animal into which DNA encoding the antibody molecule is introduced, allowing the antibody composition to form and accumulate in the animal, and collecting the antibody composition from the animal. The places where the antibody composition is formed and accumulated include milk (Japanese Published Unexamined Patent Application No. 309192/88), egg or the like of the animal. As the promoter in this process, any promoters capable of expressing in an animal can be used. Preferred promoters include mammary gland cell-specific promoters such as α casein promoter, β casein promoter, β lactoglobulin promoter and whey acidic protein promoter.

Production of the antibody composition using a plant individual can be carried out, for example, by cultivating a transgenic plant into which DNA encoding the antibody molecule is introduced according to known methods [*Soshiki Baiyo (Tissue Culture),* 20 (1994); *Soshiki Baiyo (Tissue Culture),* 21 (1995); *Trends in Biotechnology,* 15, 45 (1997)], allowing the antibody composition to form and accumulate in the plant, and collecting the antibody composition from the plant.

When the antibody variant composition produced by the transformant into which the gene encoding the antibody molecule is introduced is expressed in a soluble form in cells, the cells are recovered by centrifugation after the completion of culturing and suspended in an aqueous buffer, followed by disruption using a sonicator, French press, Manton Gaulin homogenizer, Dynomill or the like to obtain a cell-free extract.

A purified preparation of the antibody composition can be obtained by centrifuging the cell-free extract to obtain the supernatant and then subjecting the supernatant to ordinary means for isolating and purifying enzymes, e.g., extraction with a solvent, salting-out with ammonium sulfate, and the like, desalting, precipitation with an organic solvent, anion exchange chromatography using resins such as diethylaminoethyl (DEAE)-Sepharose and DIAION HPA-75 (manufactured by Mitsubishi Chemical Corporation), cation exchange chromatography using resins such as S-Sepharose FF (manufactured by Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

Also, when the antibody composition is expressed by forming an inclusion body in cells, the cells are similarly recovered and disrupted, followed by centrifugation to recover the inclusion body of the antibody composition as a precipitate fraction. The recovered inclusion body of the antibody composition is solubilized with a protein-denaturing agent. The solubilized antibody solution is diluted or dialyzed, whereby the antibody composition is renatured to have normal three-dimensional structure. Then, a purified preparation of the antibody composition can be obtained by the same isolation and purification methods as described above.

When the antibody composition is extracellularly secreted, the antibody composition or its derivative can be recovered in the culture supernatant. That is, the culture is treated by the same means as above, e.g., centrifugation, to obtain the culture supernatant. A purified preparation of the antibody composition can be obtained from the culture supernatant by using the same isolation and purification methods as described above.

The purified antibody variant composition of the present invention is a composition comprising solely antibody molecules to which no sugar chain is bound, except for Asn at position 297 according to the EU index in the Fc region. Namely, the purified antibody variant composition of the present invention is a composition only comprising antibody variant molecules in which the sugar chain binds to only Asn at position 297 according to the EU index in the Fc region.

In addition, since the antibody variant composition of the present invention after purification is an antibody composition comprising uniform antibody molecules to which extra sugar chains are not bound, except for Asn at position 297 according to the EU index in the Fc region, it is more useful than an antibody composition comprising antibody molecules to which extra sugar chains are bound.

2. Preparation of Antibody Variant Composition-Producing Cell of the Present Invention In the antibody variant composition of the present invention, the antibody variant composition having high ADCC activity in which sugar chains bound to Asn at position other than position 297 are decreased or deleted can be prepared by controlling a core fucose of the sugar chain which binds to Asn at position 279 in the Fc region of the antibody. A cell in which a core fucose is controlled can be prepared using the following method.

Specifically, a cell in which an enzyme relating to the sugar chain modification of a core fucose bound to Asn at position 297 in the Fc region of the antibody is selected, wherein the enzyme includes an enzyme relating to the synthesis of GDP-L-fucose, an enzyme relating to transport to Golgi body, or a enzyme relative to the binding of a core fucose. A cell can be also obtained by various artificial techniques described below. These obtained cells can be used as a host cell. The details are described below.

Specifically, a cell in which a core fucose is controlled can be prepared by a method for decreasing or deleting an enzymatic activity relating the sugar chain modification of a core fucose, or method for increasing an activity of a core fucose cleavage enzyme.

Examples of the enzyme relating to the sugar chain modification of a core fucose include an enzyme relating to the synthesis or transport of GDP-L-fucose and an enzyme relating to the binding of a core fucose to a complex type N-glycoside-linked sugar chain.

Specific examples of the enzyme relating to the synthesis or transport of GDP-L-fucose include GDP-mannose 4,6-dehydratase (hereinafter referred to as GMD), GDP-4-keto-6-deoxy-D-mannose-3,5-epimerase (hereinafter referred to as Fx), GDP-beta-L-fucose pyrophosphorylase (hereinafter referred to as GFPP), fucokinase, GDP-L-fucose transporter and the like.

Examples of the enzymes relating to the binding of a core fucose to a complex type N-glycoside-linked sugar chain include α1,6-fucosyltransferase (hereinafter referred to as FUT8), α-L-fucosidase, and the like.

The cell for producing the antibody variant composition of the present invention include a cell in which one of the above enzyme activities is decreased or deleted or a cell in which plural of the above enzyme activities are decreased or deleted. In addition, a cell in which the enzyme activity relating to the sugar chain modification of a core fucose is originally low may can be used by further decreasing or deleting the enzyme activity relating to the sugar chain modification of a core fucose.

(1) Gene Disruption Technique Targeting at a Gene Encoding an Enzyme

The host cell used for preparing a cell which produces an antibody having a high ADCC activity (hereinafter referred to as a high ADCC activity antibody) can be prepared by disrupting a gene encoding an enzyme relating to the sugar chain modification of a core fucose.

The gene as used herein includes DNA and RNA.

The method of gene disruption may be any method capable of disrupting the gene encoding the enzyme. Useful methods include the antisense method, the ribozyme method, the homologous recombination method, the RNA-DNA oligonucleotide method (hereinafter referred to as the RDO method), the RNA interference method (hereinafter referred to as the RNAi method), the method using a retrovirus and the method using a transposon, and the like. These methods are specifically described below.

Examples of the host cell for producing the antibody variant composition of the present invention include yeast, an animal cell, an insect cell and a plant cell having a gene of a target enzyme relating to a fucose modification or having no gene of the enzyme relating to a fucose modification originally. Specifically, any host cell described in the above 1 can be used.

When a plant cell is used as a host cell, a protein having human type sugar chains can be produced by decreasing or deleting a gene encoding an enzyme relating to binding of α1,3-fucose and a gene encoding an enzyme relating to binding β1,2-xylose.

(a) Preparation of the Host Cell for the Production of the Antibody Variant Composition of the Present Invention by the Antisense Method or the Ribozyme Method The host cell used for the production of the antibody variant composition of the present invention can be prepared by the antisense method or the ribozyme method described in *Cell Technology,* 12, 239 (1993); *BIO/TECHNOLOGY,* 17, 1097 (1999); *Hum. Mol. Genet.,* 5, 1083 (1995); *Cell Technology,* 13, 255 (1994); *Proc. Natl. Acad. Sci. USA.,* 96, 1886 (1999); and the like targeting at a gene encoding an enzyme relating to the fucose modification in the following manner.

A cDNA or a genomic DNA encoding an enzyme relating to the sugar chain modification of a core fucose is prepared. The nucleotide sequence of the prepared cDNA or genomic DNA is determined. Based on the determined DNA sequence, an antisense gene or a ribozyme of appropriate length is designed which comprises a DNA moiety encoding the enzyme relating to the fucose modification, non-translated regions or introns.

In order to express the antisense gene or ribozyme in a cell, a recombinant vector is prepared by inserting a fragment or full-length of the prepared DNA into a site downstream of a promoter in an appropriate expression vector. A transformant can be obtained by introducing the recombinant vector into a host cell suited for the expression vector.

The host cell used for the production of the antibody variant composition of the present invention can be obtained by selecting a transformant using, as an index, the activity of the enzyme relating to the fucose modification. The host cell used for the production of the antibody variant composition of the present invention can also be obtained by selecting a transformant using, as an index, the sugar chain structure of a glycoprotein on the cell membrane or the sugar chain structure of the produced antibody molecule.

The expression vectors that can be employed are those capable of autonomous replication or integration into the chromosome in the above host cells and comprising a promoter at a position appropriate for the transcription of the designed antisense gene or ribozyme. Examples of the expression vectors include those described in 3 below.

Introduction of a gene into various host cells can be carried out by the methods suitable for introducing a recombinant vector into various host cells described in 2 below.

Selection of a transformant using, as an index, the activity of an enzyme relating to the fucose modification can be carried out by the following methods.

Methods for Selecting a Transformant

A cell in which the activity of an enzyme relating to the fucose modification is deleted can be selected by measuring the activity of the enzyme relating to the fucose modification using biochemical methods or genetic engineering techniques described in *Shin Seikagaku Jikken Koza* (*New Lectures on Experiments in Biochemistry*) 3-*Saccharides Glycoprotein* (Tokyo Kagaku Dojin), edited by The Japanese Biochemical Society (1988); *Cell Technology, Extra Edition, Experimental Protocol Series, Glycobiology Experimental Protocol, Glycoprotein, Glycolipid and Proteoglycan* (Shujunsha), edited by Naoyuki Taniguchi, Akemi Suzuki, Kiyoshi Furukawa and Kazuyuki Sugawara (1996); *Molecular Cloning*, Second Edition; *Current Protocols in Molecular Biology*; and the like.

An example of the biochemical methods is a method in which the enzyme activity is evaluated using an enzyme-specific substrate. Examples of the genetic engineering techniques include Northern analysis and RT-PCR in which the amount of mRNA for a gene encoding the enzyme is measured.

Selection of a transformant using the sugar chain structure of a glycoprotein on the cell membrane as an index can be carried out, for example, by the method described in 5 below. Selection of a transformant using, the sugar chain structure of a produced antibody molecule as an index can be carried out, for example, by the methods described in 5 below.

Preparation of a cDNA Encoding an Enzyme Relating to the Fucose modification can be carried out, for example, by the following method.

Preparation Method of cDNA

Total RNA or mRNA is prepared from a various host cell tissue or cell. A cDNA library is prepared from the obtained total RNA or mRNA. Degenerative primers are prepared based on the amino acid sequence of an enzyme relating to the fucose modification. A gene fragment encoding the enzyme relating to the sugar chain modification of a core fucose is obtained by PCR using the prepared cDNA library as a template.

A DNA encoding the enzyme relating to the fucose modification can be obtained by screening the cDNA library using the obtained gene fragment as a probe. As the mRNA of a human or non-human animal tissue or cell, commercially available one (for example, manufactured by Clontech) may be used, or it may be prepared from a human or non-human animal tissue or cell in the following manner.

The methods for preparing total RNA from a human or non-human animal tissue or cell include the guanidine thiocyanate-cesium trifluoroacetate method [*Methods in Enzymology*, 154, 3 (1987)], the acidic guanidine thiocyanate-phenol-chloroform (AGPC) method [*Analytical Biochemistry*, 162, 156 (1987); *Experimental Medicine*, 9, 1937 (1991)] and the like.

The methods for preparing mRNA as poly(A)$^+$RNA from the total RNA include the oligo (dT) immobilized cellulose column method (*Molecular Cloning*, Second Edition).

It is also possible to prepare mRNA by using a commercially available kit such as Fast Track mRNA Isolation Kit (manufactured by Invitrogen) or Quick Prep mRNA Purification Kit (manufactured by Pharmacia).

A cDNA library is prepared from the obtained mRNA of a human or non-human animal tissue or cell. The methods for preparing the cDNA library include the methods described in *Molecular Cloning*, Second Edition; *Current Protocols in Molecular Biology; A Laboratory Manual*, 2nd Ed. (1989); and the like, and methods using commercially available kits such as SuperScript Plasmid System for cDNA Synthesis and Plasmid Cloning (manufactured by Life Technologies) and ZAP-cDNA Synthesis Kit (manufactured by STRATAGENE).

As the cloning vector for preparing the cDNA library, any vectors, e.g. phage vectors and plasmid vectors, can be used so long as they are autonomously replicable in *Escherichia coli* K12.

Examples of suitable vectors include ZAP Express [manufactured by STRATAGENE; *Strategies*, 5, 58 (1992)], pBluescript II SK(+) [*Nucleic Acids Research*, 17, 9494 (1989)], λZAP II (manufactured by STRATAGENE), λgt10, λgt11 [*DNA Cloning, A Practical Approach*, 1, 49 (1985)], λTriplEx (manufactured by Clontech), λExCell (manufactured by Pharmacia), pT7T318U (manufactured by Pharmacia), pcD2 [*Mol. Cell. Biol.*, 3, 280 (1983)], pUC18 [*Gene*, 33, 103 (1985)], and the like.

Any microorganism can be used as the host microorganism for preparing the cDNA library, but *Escherichia coli* is preferably used. Examples of suitable host microorganisms are *Escherichia coli* XL1-Blue MRF' [manufactured by STRATAGENE; *Strategies*, 5, 81 (1992)], *Escherichia coli* C600 [*Genetics*, 39, 440 (1954)], *Escherichia coli* Y1088 [*Science*, 222, 778 (1983)], *Escherichia coli* Y1090 [*Science*, 222, 778 (1983)], *Escherichia coli* NM522 [*J. Mol. Biol.*, 166, 1 (1983)], *Escherichia coli* K802 [*J. Mol. Biol.*, 16, 118 (1966)], *Escherichia coli* JM105 [*Gene*, 38, 275 (1985)], and the like.

The cDNA library may be used as such in the following analysis. Alternatively, in order to efficiently obtain full-length cDNAs by decreasing the ratio of partial cDNAs, a cDNA library prepared using the oligo-cap method developed by Sugano, et al. [*Gene*, 138, 171 (1994); *Gene*, 200, 149 (1997); *Protein, Nucleic Acid and Enzyme*, 41, 603 (1996); *Experimental Medicine*, 11, 2491 (1993); *cDNA Cloning* (Yodosha) (1996); *Methods for Preparing Gene Libraries* (Yodosha) (1994)] may be used in the following analysis.

Degenerative primers specific for the 5'-terminal and 3'-terminal nucleotide sequences are prepared based on a nucleotide sequence presumed to encode the amino acid sequence of an enzyme relating to fucose modification. Then the gene fragments encoding the enzyme relating to fucose modification are obtained by amplyfing DNA by the PCR method [PCR Protocals, Academic Press, (1990)] using prepared cDNA librarie and primers.

It can be confirmed that the obtained gene fragment is a DNA encoding the enzyme relating to the sugar chain modification of a core fucose by analyzing the nucleotide sequence by generally employed nucleotide sequence analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

A DNA encoding the enzyme relating to the fucose modification can be obtained from the cDNA or cDNA library synthesized from the mRNA contained in a human or non-human animal tissue or cell by colony hybridization or plaque hybridization (*Molecular Cloning*, Second Edition) using the above gene fragment as a probe.

A cDNA encoding the enzyme relating to the fucose modification can also be obtained by amplification by PCR using the cDNA or cDNA library synthesized from the mRNA contained in a human or non-human animal tissue or cell as a template and using the primers used for obtaining the gene fragment encoding the enzyme relating to the fucose modification.

The nucleotide sequence of the DNA encoding the enzyme relating to the fucose modification can be determined by generally employed nucleotide sequence analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the cDNA, it can be confirmed that the obtained DNA is a gene encoding the enzyme relating to the fucose modification among the genes in the nucleotide sequence database.

Examples of the nucleotide sequences of the genes encoding the enzyme relating to the synthesis of GDP-L-fucose obtained by the above methods include the nucleotide sequence of GMD and the nucleotide sequence of Fx disclosed in WO2005/035741.

Examples of the nucleotide sequences of the genes encoding the enzyme relating to the sugar chain modification of a core fucose in a complex-type N-glycoside-linked sugar chain obtained by the above methods include the nucleotide sequence of FUT8 disclosed in U.S. Pat. No. 7,393,683.

Examples of the nucleotide sequences of the genes encoding the enzyme relating to the transport of GDP-L-fucose to Golgi body obtained by the above methods include the nucleotide sequence of GDP-L-fucose transporter disclosed in U.S. Application Publication No. 2004/0110282.

The cDNA encoding the enzyme relating to the fucose modification can also be obtained by chemical synthesis with a DNA synthesizer such as DNA Synthesizer Model 392 (manufactured by Perkin Elmer) utilizing the phosphoamidite method based on the determined nucleotide sequence of the desired DNA.

Preparation of a Genomic DNA Encoding the Enzyme Relating to the Fucose modification can be carried out by the following method.

Method for Preparing Genomic DNA

The genomic DNA can be prepared by known methods described in *Molecular Cloning*, Second Edition, *Current Protocols in Molecular Biology*, and the like In addition, the genomic DNA encoding the enzyme relating to the sugar chain modification of a core fucose can also be obtained by using a kit such as Genomic DNA Library Screening System (manufactured by Genome Systems) or Universal GenomeWalker™ Kits (manufactured by CLONTECH).

The nucleotide sequence of the DNA encoding the enzyme relating to the fucose modification can be determined by generally employed nucleotide analyzing methods such as the dideoxy method of Sanger, et al. [*Proc. Natl. Acad. Sci. U.S.A.*, 74, 5463 (1977)] or by use of nucleotide sequence analyzers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the genomic DNA, it can be confirmed that the obtained DNA is a gene encoding the e enzyme relating to the fucose modification among the genes in the nucleotide sequence database.

The genomic DNA encoding the enzyme relating to the enzyme relating to the sugar chain modification of a core fucose can also be obtained by chemical synthesis with a DNA synthesizer such as DNA Synthesizer Model 392 (manufactured by Perkin Elmer) utilizing the phosphoamidite method based on the determined nucleotide sequence of the DNA.

The host cell used for the production of the antibody variant composition of the present invention can also be obtained without using an expression vector by directly introducing into a host cell an antisense oligonucleotide or ribozyme designed based on the nucleotide sequence encoding the enzyme relating to the fucose modification. The antisense oligonucleotide or ribozyme can be prepared by known methods or by using a DNA synthesizer.

Specifically, based on the sequence information on an oligonucleotide having a sequence corresponding to preferably 5 to 150, more preferably 5 to 60, further preferably 10 to 40 continuous nucleotides in the nucleotide sequence of the cDNA and genomic DNA encoding the enzyme relating to the fucose modification, an oligonucleotide corresponding to the sequence complementary to the above oligonucleotide (antisense oligonucleotide) or a ribozyme comprising the oligonucleotide sequence can be synthesized.

The oligonucleotide includes oligo RNA and derivatives of the oligonucleotide (hereinafter referred to as oligonucleotide derivatives).

The oligonucleotide derivatives include an oligonucleotide derivative wherein the phosphodiester bond in the oligonucleotide is converted to a phosophorothioate bond, an oligonucleotide derivative wherein the phosphodiester bond in the oligonucleotide is converted to an N3'-P5' phosphoamidate bond, an oligonucleotide derivative wherein the ribose-phosphodiester bond in the oligonucleotide is converted to a peptide-nucleic acid bond, an oligonucleotide derivative wherein the uracil in the oligonucleotide is substituted with C-5 propynyluracil, an oligonucleotide derivative wherein the uracil in the oligonucleotide is substituted with C-5 thiazolyluracil, an oligonucleotide derivative wherein the cytosine in the oligonucleotide is substituted with C-5 propynylcytosine, an oligonucleotide derivative wherein the cytosine in the oligonucleotide is substituted with phenoxazine-modified cytosine, an oligonucleotide derivative wherein the ribose in the oligonucleotide is substituted with 2'-O-propylribose, and an oligonucleotide derivative wherein the ribose in the oligonucleotide is substituted with 2'-methoxyethoxyribose [*Saibou Kogaku (Cell Technology)*, 16, 1463 (1997)].

(b) Preparation of the Host Cell Used for the Production of the Antibody Variant Composition of the Present Invention by the Homologous Recombination Method The host cell used for the production of the antibody variant composition of the present invention can be prepared by modifying a target gene on the chromosome by the homologous recombination method targeting a gene encoding an enzyme relating to the fucose modification.

Modification of the target gene on the chromosome can be carried out by using the methods described in *Manipulating* the Mouse Embryo, A Laboratory Manual, Second Edition, Cold Spring Harbor Laboratory Press (1994) (hereinafter referred to as "Manipulating the Mouse Embryo, A Laboratory Manual"; Gene Targeting, A Practical Approach, IRL Press at Oxford University Press (1993); Biomanual Series 8, Gene Targeting, Preparation of Mutant Mice Using ES Cells, Yodosha (1995) (hereinafter referred to as Preparation of Mutant Mice Using ES Cells); and the like, for example, in the following manner.

A genomic DNA encoding the enzyme relating to the fucose modification is prepared. Based on the nucleotide sequence of the genomic DNA, a target vector is prepared for homologous recombination of a target gene to be modified (e.g., the structural gene or promoter gene for the enzyme relating to the fucose modification of a core fucose).

The host cell used for the production of the high ADCC activity antibody-producing cell can be prepared by introducing the prepared target vector into a host cell and selecting a cell in which homologous recombination occurred between the target gene on the chromosome and the target vector.

As the host cell, any yeast, animal cells, insect cells, plant cells, or the like can be used so long as it has a gene encoding the enzyme relating to the fucose modification. Examples of the host cells include those described in 2 below.

The genomic DNA encoding the enzyme relating to the sugar chain modification of a core fucose can be prepared by the methods for preparing a genomic DNA described in the above 1 (1) (a).

The target vector for use in the homologous recombination of the target gene on the chromosome can be prepared according to the methods described in Gene Targeting, A Practical Approach, IRL Press at Oxford University Press (1993); Biomanual Series 8, Gene Targeting, Preparation of Mutant Mice Using ES Cells, Yodosha (1995); and the like.

The target vector may be either a replacement type or an insertion type.

Introduction of the target vector into various host cells can be carried out by the methods suitable for introducing a recombinant vector into various host cells described in 3 below.

The methods for efficiently selecting a homologous recombinant include positive selection, promoter selection, negative selection and polyA selection described in Gene Targeting, A Practical Approach, IRL Press at Oxford University Press (1993); Biomanual Series 8, Gene Targeting, Preparation of Mutant Mice Using ES Cells, Yodosha (1995); and the like The methods for selecting the desired homologous recombinant from the selected cell lines include Southern hybridization (Molecular Cloning, Second Edition) and PCR method [PCR Protocols, Academic Press (1990)] for the genomic DNA.

(c) Preparation of the Host Cell Used for the Antibody Variant Composition of the Present Invention by The RDO Method The host cell used for the production of the antibody variant composition of the present invention can be prepared by the RDO method targeting a gene encoding an enzyme relating to the fucose modification, in the following manner.

A cDNA or a genomic DNA encoding an enzyme relating to the enzyme relating to the fucose modification is prepared by the methods described in the above 1 (a). The nucleotide sequence of the prepared cDNA or genomic DNA is determined. Based on the determined DNA sequence, an RDO construct of appropriate length which comprises a part encoding the enzyme relating to the fucose modification, a part of its non-translated region or a part of introns is designed and synthesized.

The host cell can be obtained by introducing the synthesized RDO into a host cell and then selecting a transformant in which a mutation occurred in the target enzyme, that is, the enzyme relating to the fucose modification.

As the host cell, any yeast, animal cell, insect cell, plant cell, or the like can be used so long as it has a gene encoding the enzyme relating to the fucose modification. Examples of the host cells include those described in 3 below.

Introduction of the RDO into various host cells can be carried out by the methods suitable for introducing a recombinant vector into various host cells described in 3 below.

The cDNA encoding the enzyme relating to the fucose modification can be prepared by the methods for preparing a cDNA described in the above 1 (a) or the like.

The genomic DNA encoding the enzyme relating to the fucose modification can be prepared by the methods for preparing a genomic DNA described in the above 1 (a) or the like.

After DNA is cleaved with appropriate restriction enzymes, the nucleotide sequence of the DNA can be determined by subcloning the DNA fragments into a plasmid such as pBluescript SK(-) (manufactured by Stratagene), subjecting the clones to the reaction generally used as a method for analyzing a nucleotide sequence such as the dideoxy method of Sanger et al. [Proc. Natl. Acad. Sci., USA, 74, 5463 (1977)] or the like, and then analyzing the clones by using an automatic nucleotide sequence analyzer such as ABI PRISM 377 DNA Sequencer (manufactured by Applied Biosystems) or the like.

The RDO can be prepared by conventional methods or by using a DNA synthesizer.

The methods for selecting a cell in which a mutation occurred by introducing the RDO into the host cell, in the gene encoding the enzyme relating to the fucose modification include the methods for directly detecting mutations in chromosomal genes described in Molecular Cloning, Second Edition, Current Protocols in Molecular Biology, and the like.

For the selection of the transformant, the following methods can also be employed: the method using, as an index, the activity of the enzyme relating to the fucose modification described in the above; the method using, as an index, the sugar chain structure of a glycoprotein on the cell membrane as described below; and the method using, as an index, the sugar chain structure of a produced antibody molecule described below.

The construct of RDO can be designed according to the descriptions in Science, 273, 1386 (1996); Nature Medicine, 4, 285 (1998); Hepatology, 25, 1462 (1997); Gene Therapy, 5, 1960 (1999); Gene Therapy, 5, 1960 (1999); J. Mol. Med., 75, 829 (1997); Proc. Natl. Acad. Sci. USA, 96, 8774 (1999); Proc. Natl. Acad. Sci. USA, 96, 8768 (1999); Nuc. Acids Res., 27, 1323 (1999); Invest. Dermatol., 111, 1172 (1998); Nature Biotech., 16, 1343 (1998); Nature Biotech., 18, 43 (2000); Nature Biotech., 18, 555 (2000); and the like.

(d) Preparation of the Host Cell for the Production of the Antibody Variant Composition of the Present Invention by the RNAi Method The host cell used for the production of the antibody variant composition of the present invention can be prepared by the RNAi method targeting the gene encoding the enzyme relating to the fucose modification in the following manner.

A cDNA encoding an enzyme relating to the fucose modification is prepared by the methods described in the above 1. The nucleotide sequence of the prepared cDNA is determined. Based on the determined cDNA sequence, an RNAi gene of appropriate length is designed which comprises a part encoding the enzyme relating to the fucose modification, or a part of non-translated regions.

In order to express the RNAi gene in a cell, a recombinant vector is prepared by inserting a fragment or full-length of the prepared cDNA into a site downstream of a promoter in an appropriate expression vector.

The recombinant vector is introduced into a host cell suitable for the expression vector to obtain a transformant.

The host cell used for the preparation of the antibody variant composition of the present invention can be obtained by selecting a transformant using, as an index, the activity of the enzyme relating to the fucose modification, or the sugar chain structure of a produced antibody molecule or a glycoprotein on the cell membrane.

As the host cell, any yeast, animal cells, insect cells, plant cells, or the like can be used so long as it has a gene encoding the enzyme relating to the fucose modification. Examples of the host cells include those described in 3 below.

The expression vectors that can be employed are those capable of autonomous replication or integration into the chromosome in the above host cells and comprising a promoter at a position appropriate for the transcription of the designed RNAi gene. Examples of the expression vectors include those described in 3 below.

Introduction of a gene into various host cells can be carried out by the methods suitable for introducing a recombinant vector into various host cells described in 3 below.

The methods for selecting the transformant using, as an index, the activity of the enzyme relating to the fucose modification include the methods described in the above 1.

The methods for selecting the transformant using, as an index, the sugar chain structure of a produced glycoprotein molecule on the cell membrane include the method described in 1 (a) below. The methods for selecting the transformant using, as an index, the sugar chain structure of a produced antibody molecule include the methods described in 5 below.

The methods for preparing cDNA encoding the enzyme relating to the fucose modification include the methods for preparing a cDNA described in the above 1 (a), and the like.

The host cell used for the production of the antibody variant composition of the present invention can also be obtained, without using an expression vector, by directly introducing into a host cell the RNAi gene designed based on the nucleotide sequence encoding the enzyme relating to the fucose modification.

The RNAi gene can be prepared by known methods or by using a DNA synthesizer. The RNAi gene construct can be designed according to the descriptions in *Nature*, 391, 806 (1998); *Proc. Natl. Acad. Sci. USA*, 95, 15502 (1998); *Nature*, 395, 854 (1998); *Proc. Natl. Acad. Sci. USA*, 96, 5049 (1999); *Cell*, 95, 1017 (1998); *Proc. Natl. Acad. Sci. USA*, 96, 1451 (1999); *Proc. Natl. Acad. Sci. USA*, 95, 13959 (1998); *Nature Cell Biol.*, 2, 70 (2000); and the like.

(e) Preparation of the Host Cell for the Production of the Antibody Variant Composition of the Present Invention by the Method Using a Transposon The host cell used for the production of the antibody variant composition of the present invention can be prepared by using the transposon system described in *Nature Genet.*, 25, 35 (2000), and the like, and then selecting a mutant using, as an index, the activity of the enzyme relating to the fucose modification, or the sugar chain structure of a produced glycoprotein molecule or a glycoprotein on the cell membrane.

The transposon system is a system for inducing a mutation by random insertion of an exogenous gene into the chromosome. In the system, an exogenous gene inserted into a transposon is usually used as a vector for inducing a mutation and a transposase expression vector for randomly inserting the gene into the chromosome is introduced into the cell at the same time.

Any transposase can be used so long as it is suitable for the sequence of the transposon to be used.

As the exogenous gene, any gene can be used so long as it can induce a mutation in the DNA of a host cell.

As the host cell, any yeast, animal cells, insect cells, plant cells or the like can be used so long as it has a gene encoding the enzyme relating to the fucose modification. Examples of the host cells include those described in the above 1. Introduction of the gene into various host cells can be carried out by the methods suitable for introducing a recombinant vector into various host cells described in 2 below.

The methods for selecting the mutant using, as an index, the activity of the enzyme relating to the fucose modification include the methods described in 2 below.

The methods for selecting the mutant using, as an index, the sugar chain structure of a glycoprotein on the cell membrane include the method described in 1 (a). The methods for selecting the mutant using, as an index, the sugar chain structure of a produced glycoprotein molecule include the methods described in 5 below.

(2) Technique of Introducing a Dominant-Negative Mutant of a Gene Encoding an Enzyme The host cell used for the production of the antibody variant composition of the present invention can be prepared by using the technique of introducing a dominant-negative mutant of a target gene, i.e., a gene encoding an enzyme relating to the fucose modification.

Examples of the enzymes relating to the synthesis of GDP-L-fucose include GMD and Fx.

Examples of the enzymes relating to the sugar chain modification of a core fucose at the reducing terminal of a complex-type N-glycoside-linked sugar chain include $\alpha 1,6$-fucosyltransferase.

Examples of the protein relating to the transport of GDP-L-fucose to Golgi body include GDP-L-fucose transporter.

These enzymes or proteins have substrate specificity and catalyze specific reactions. By disrupting the active center of such enzymes or proteins having substrate specificity and catalytic activity, their dominant-negative mutants can be prepared.

Preparation of a Dominant-Negative Mutant is Described in Detail Below, using GMD as an example among the target enzymes.

As a result of the analysis of the three-dimensional structure of GMD derived from *Escherichia coli*, it has been found that four amino acids (Thr at position 133, Glu at position 135, Tyr at position 157 and Lys at position 161) have an important function for the enzyme activity (*Structure*, 8, 2, 2000).

That is, the mutants prepared by substituting the above four amino acids by other amino acids based on the three-dimensional structure information all showed significantly decreased enzyme activity.

On the other hand, little change was observed in the ability of the mutants to bind to the GMD coenzyme NADP or the substrate GDP-mannose. Accordingly, a dominant-negative mutant can be prepared by substituting the four amino acids which are responsible for the enzyme activity of GMD.

On the basis of the result of preparation of a dominant-negative mutant of GMD derived from *Escherichia coli*, dominant-negative mutants can be prepared by performing homology comparison and three-dimensional structure prediction using the amino acid sequence information. For example, in the case of GMD derived from CHO cell, a dominant-negative mutant can be prepared by substituting Thr at position 155, Glu at position 157, Tyr at position 179 and Lys at position 183 by other amino acids.

Preparation of Such a Gene Carrying Introduced Amino Acid Substitutions can be carried out by site-directed mutagenesis described in *Molecular Cloning*, Second Edition, *Current Protocols in Molecular Biology*, and the like.

The host cell used for the production of the high ADCC activity antibody-producing cell can be prepared according to the method of gene introduction described in *Molecular Cloning*, Second Edition, *Current Protocols in Molecular Biology*, *Manipulating the Mouse Embryo*, Second Edition, and the like using a gene encoding a dominant-negative mutant of a target enzyme (hereinafter abbreviated as dominant-negative mutant gene) prepared as above, for example, in the following manner.

A dominant-negative mutant gene encoding the enzyme relating to the sugar chain modification of a core fucose at the reducing terminal of a complex-type N-glycoside-linked sugar chain or the enzyme relating to the synthesis of GDP-L-fucose is prepared.

Based on the full-length DNA of the prepared dominant-negative mutant gene, a DNA fragment of appropriate length containing a region encoding the protein is prepared according to need.

A recombinant vector is prepared by inserting the DNA fragment or full-length DNA into a site downstream of a promoter in an appropriate expression vector. The recombinant vector is introduced into a host cell suited for the expression vector to obtain a transformant.

The host cell used for the preparation of the high ADCC activity antibody-producing cell can be obtained by selecting a transformant using, as an index, the activity of the enzyme relating to the synthesis of GDP-L-fucose, the activity of the enzyme relating to the sugar chain modification of a core fucose at the reducing terminal of a complex-type N-glycoside-linked sugar chain, or the sugar chain structure of a produced antibody molecule or a glycoprotein on the cell membrane.

As the host cell, any yeast, animal cell, insect cell, plant cell, or the like can be used so long as it has a gene encoding the enzyme relating to the fucose modification. Examples of the host cells include those described in the above 1.

The expression vectors that can be employed are those capable of autonomous replication or integration into the chromosome in the above host cells and comprising a promoter at a position appropriate for the transcription of the DNA encoding the desired dominant-negative mutant. Examples of the expression vectors include those described in the above 1.

Introduction of a gene into various host cells can be carried out by the methods suitable for introducing a recombinant vector into various host cells described in the above 1.

The methods for selecting the transformant using, as an index, the activity of the enzyme relating to the synthesis of an intracellular sugar nucleotide, GDP-L-fucose or the activity of the enzyme relating to the sugar chain modification of a core fucose at the reducing terminal of a complex-type N-glycoside-linked sugar chain include the methods described in 2 (1) (a) below.

The methods for selecting the transformant using, as an index, the sugar chain structure of a glycoprotein on the cell membrane include the method described in 2 (5) below. The methods for selecting the transformant using, as an index, the sugar chain structure of a produced antibody molecule include the methods described in 4 or 5 below.

(3) Technique of Introducing a Mutation into an Enzyme

The host cell used for the preparation of the high ADCC activity antibody-producing cell can be prepared by introducing a mutation into a gene encoding the enzyme relating to the synthesis of GDP-L-fucose or the enzyme relating to the sugar chain modification of a core fucose at the reducing terminal of a complex-type N-glycoside-linked sugar chain, and then selecting a desired cell line in which the mutation occurred in the enzyme.

Examples of the enzymes relating to the synthesis of GDP-L-fucose include GMD, Fx, and the like.

Examples of the enzymes relating to the sugar chain modification of a core fucose in the reducing terminal of a complex-type N-glycoside-linked sugar chain include α1,6-fucosyltransferase, α-L-fucosidase, and the like.

The methods for introducing a mutation into the enzyme include: 1) a method in which a desired cell line is selected from mutants obtained by subjecting a parent cell line to the treatment of mutagenesis or by spontaneous mutation using, as an index, the activity of the enzyme relating to the synthesis of GDP-L-fucose or the activity of the enzyme relating to the sugar chain modification of a core fucose in the reducing terminal of a complex-type N-glycoside-linked sugar chain; 2) a method in which a desired cell line is selected from mutants obtained by subjecting a parent cell line to the treatment of mutagenesis or by spontaneous mutation using, as an index, the sugar chain structure of a produced antibody molecule; and 3) a method in which a desired cell line is selected from mutants obtained by subjecting a parent cell line to the treatment of mutagenesis or by spontaneous mutation using, as an index, the sugar chain structure of a glycoprotein on the cell membrane.

Mutagenesis may be carried out by any method capable of inducing a point mutation, a deletion mutation or a frame-shift mutation in DNA of a parent cell line. Suitable methods include treatment with ethyl nitrosourea, nitrosoguanidine, benzopyrene or an acridine dye and irradiation. Various alkylating agents and carcinogens are also useful as mutagens. A mutagen is allowed to act on a cell by the methods described in *Soshiki Baiyo no Gijutsu* (*Tissue Culture Techniques*), Third Edition (Asakura Shoten), edited by The Japanese Tissue Culture Association (1996); *Nature Genet.*, 24, 314 (2000); and the like.

Examples of the mutants generated by spontaneous mutation include spontaneous mutants obtained by continuing subculture under usual cell culture conditions without any particular treatment for mutagenesis.

(4) Technique of Suppressing Transcription or Translation of a Gene Encoding an Enzyme The host cell used for the preparation of the high ADCC activity antibody-producing cell can be prepared by suppressing transcription or translation of a target gene, i.e., a target gene encoding an enzyme relating to the synthesis of GDP-L-fucose or an enzyme relating to the sugar chain modification of a core fucose in the reducing terminal of a complex-type N-glycoside-linked sugar chain using the antisense RNA/DNA technique [*Bioscience and Industry*, 50, 322 (1992); *Chemistry*, 46, 681 (1991); *Biotechnology*, 9, 358 (1992); *Trends in Biotechnology*, 10, 87 (1992); *Trends in Biotechnology*, 10, 152 (1992); *Cell Technology*, 16, 1463 (1997)], the triple helix technique [*Trends in Biotechnology*, 10, 132 (1992)], and the like.

(5) Technique of Selecting a Cell Line Resistant to a Lectin which Recognizes a Core Fucose in the Reducing Terminal of a N-Glycoside-Linked Sugar Chain The host cell used for the preparation of the high ADCC activity antibody-producing cell can be prepared by selecting a cell line resistant to a lectin which recognizes a sugar chain structure in which 1-position of fucose is bound to 6-position of N-acetylglucosamine through α-bond in the reducing terminal of a N-glycoside-linked sugar chain.

Selection of the cell line resistant to the lectin which recognizes the core fucose in the reducing terminal of a N-glycoside-linked sugar chain can be carried out, for example, by the method using a lectin described in *Somatic Cell Mol. Genet.*, 12, 51 (1986), and the like.

As the lectin, any lectin can be used so long as it recognizes the sugar chain structure in which 1-position of fucose is bound to 6-position of N-acetylglucosamine in the reducing terminal through α-bond in a N-glycoside-linked sugar chain.

Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

Specifically, cells are cultured in a medium containing the above lectin at a concentration of 1 μg/ml to 1 mg/ml for one day to two weeks, preferably one day to one week, subculturing surviving cells or picking up a colony and transferring it into a culture vessel. By subsequently continuing the culturing using the medium containing the lectin, the cell line resistant to the lectin which recognizes the sugar chain structure in which 1-position of fucose is bound to 6-position of N-acetylglucosamine in the reducing terminal through α-bond in a N-glycoside-linked sugar chain can be selected.

3. Evaluation of the Activity of the Antibody Composition

The protein amount, FcR binding activity, C1q binding activity, antigen binding activity or cytotoxic activity, such as ACDD activity and CDC activity of the purified antibody variant composition can be measured using the known methods described in *Monoclonal Antibodies, Antibody Engineering*, or the like.

Specifically, when the antibody composition is a human chimeric antibody or a humanized antibody, the binding activity to an antigen or the binding activity to cultured cell line which is antigen-positive can be measured by ELISA, the fluorescent antibody technique [*Cancer Immunol. Immunother.*, 36, 373 (1993)], and the like.

The cytotoxic activity to cultured cell line which is antigen-positive can be evaluated by measuring CDC activity, ADCC activity, or the like [*Cancer Immunol. Immunother.*, 36, 373 (1993), U.S. Application Publication No. 2004/0259150].

The FcR binding activity of the antibody variant composition of the present invention can be confirmed by producing a recombinant FcγRIIIA protein or a recombinant neonatal Fc receptor (FcRn) and then measuring a binding activity (U.S. Application Publication No. 2004/0259150).

The method for measuring ADCC activity includes a method in which a target cell labeled with a radioisotope, a fluorescent substance, a dye or the like is allowed to contact with an antibody and an effector cell, and then the activity of the labeled substance released from the injured target cell is measured; a method in which a target cell is allowed to contact with an antibody and an effector cell, and then the biological activity of an enzyme released from the injured target cell is measured; and the like.

The method for measuring CDC activity includes a method in which a target cell labeled with a radioisotope, a fluorescent substance, a dye or the like is allowed to contact with an antibody and a biological specimen such as serum containing a complement component, and then the activity of the labeled substance released from the injured target cell is measured; a method in which a target cell is allowed to contact with an antibody and a biological specimen such as serum containing a complement component, and then the biological activity of an enzyme released from the injured target cell is measured; and the like.

The FcγR binding activity, the ADCC activity and/or the CDC activity of the antibody variant composition of the present invention in which an undesirable sugar chain is not bound to amino acid residues other than Asn at position 297 by the amino acid substitution is equal to or higher than an antibody before carrying out the amino acid substitution.

Namely, the antibody variant composition of the present invention have equal to or higher FcγR binding activity, ADCC activity and/or CDC activity as compared with the antibody having the original Fc region even though the amino acid residue of the antibody variant composition is substituted in amino acid sequences other than Asn at position 297 to which a N-glycoside-linked sugar chain is bound in Fc region.

In addition, the antibody variant composition of the present invention has higher CDC activity than human IgG1 and human IgG3 and has substantially equal to or higher ADCC activity and/or CDC activity as compared with an antibody before carrying out the amino acid substitution.

Furthermore, the antibody variant composition of the present invention having a constant region comprising the amino acid sequence represented by SEQ ID NO:3 has higher CDC activity than human IgG1 and human IgG3 and has substantially equal to or higher ADCC activity and/or CDC activity as compared with an antibody before carrying out the amino acid substitution.

The safety and therapeutic effect of the antibody composition in human can be evaluated using an appropriate animal model of a species relatively close to human, e.g., cynomolgus monkey.

4. Analysis of Sugar Chains in the Antibody Composition

The sugar chain structure of the antibody molecule expressed in various cells can be analyzed according to general methods of analyzing the sugar chain structure of glycoprotein. For example, a sugar chain bound to an IgG molecule consists of neutral sugars such as galactose (Gal), mannose (Man) and fucose (Fuc), amino sugars such as N-acetylglucosamine (GlcNAc), and acidic sugars such as sialic acid (Sial), and can be analyzed by techniques such as sugar composition analysis and sugar chain structure analysis using two-dimensional sugar chain mapping.

(1) Analysis of Neutral Sugar and Amino Sugar Compositions

The sugar chain composition of an antibody composition can be analyzed by carrying out acid hydrolysis of sugar chains with trifluoroacetic acid or the like to release neutral sugars or amino sugars and analyzing the composition ratio.

Specifically, the analysis can be carried out by a method using a carbohydrate analysis device manufactured by Dionex. BioLC is a device for analyzing the sugar composition by HPAEC-PAD (high performance anion-exchange chromatography-pulsed amperometric detection) [*J. Liq. Chromatogr.*, 6, 1577 (1983)].

The composition ratio can also be analyzed by the fluorescence labeling method using 2-aminopyridine. Specifically, the composition ratio can be calculated by fluorescence labeling an acid-hydrolyzed sample by 2-aminopyridylation according to a known method [*Agric. Biol. Chem.*, 55(1), 283-284 (1991)] and then analyzing the composition by HPLC.

(2) Analysis of Sugar Chain Structures

The sugar chain structures of an antibody composition can be analyzed by two-dimensional sugar chain mapping [*Anal. Biochem.*, 171, 73 (1988); *Seibutsukagaku Jikkenho* (*Biochemical Experimentation Methods*) 23—*Totanpakushitsu Tosa Kenkyuho* (*Methods of Studies on Glycoprotein Sugar Chains*), Gakkai Shuppan Center, edited by Reiko Takahashi (1989)]. The two-dimensional sugar chain mapping is a method of deducing a sugar chain structure, for example, by plotting the retention time or elution position of a sugar chain by reversed phase chromatography as the X axis and the retention time or elution position of the sugar chain by normal phase chromatography as the Y axis, respectively, and comparing them with the results of known sugar chains.

Specifically, a sugar chain is released from an antibody by hydrazinolysis of the antibody and subjected to fluorescence labeling with 2-aminopyridine (hereinafter referred to as PA) [*J. Biochem.*, 95, 197 (1984)]. After being separated from an extra PA-treating reagent by gel filtration, the sugar chain is subjected to reversed phase chromatography.

Then, each peak of the fractionated sugar chain is subjected to normal phase chromatography. The sugar chain structure can be deduced by plotting the obtained results on a two-dimensional sugar chain map and comparing them with the spots of a sugar chain standard (manufactured by Takara Shuzo Co., Ltd.) or those in the document [*Anal. Biochem.*, 171, 73 (1988)].

The structure deduced by the two-dimensional sugar chain mapping can be confirmed by carrying out mass spectrometry, e.g., MALDI-TOF-MS, of each sugar chain.

The portion to which a sugar chain is bound in Fc region of the antibody can be confirmed by carrying out reductive amination of the antibody, then carrying out endoprotease treatment of the obtained antibody using such as trypsin, pepsin, Lys-C or Asp-N, and separating the obtained fragment using reverse phase chromatography (LC) to analyze them using such as mass spectrometer (MS).

Namely, one can be confirm if a sugar chain is actually bound or not by checking if the molecular weights of obtainable peptides by protease treatment and the molecular weight of peptide to which a sugar chain is bound correspond to analysis values of MS based on the amino acid sequence of the objective Fc region.

5. Method for Determining the Sugar Chain Structure of an Antibody Molecule

The antibody composition of the present invention comprises antibody molecules having different sugar chain structures binding to Asn at position 297 in the Fc region of the antibody. Among the antibody variant compositions of the present invention, the antibody variant composition in which the ratio of sugar chains with no core fucose among the total complex-type N-glycoside-linked sugar chains which bind to Fc of the antibody variant composition of the present invention is 20% or more, shows high ADCC activity. Such an antibody composition can be determined using the method for analyzing the sugar chain structure of an antibody molecule described in the above 4. Further, it can also be determined by an immunological quantative method using lectins.

Determination of the sugar chain structure of an antibody molecule by an immunological quantative method using lectins can be made according to the immunoassays such as Western staining, RIA (radioimmunoassay), VIA (viroimmunoassay), EIA (enzymeimmunoassay), FIA (fluoroimmunoassay) and MIA (metalloimmunoassay) described in the document [*Monoclonal Antibodies: Principles and Applications*, Wiley-Liss, Inc. (1995); *Enzyme Immunoassay*, 3rd Ed., Igaku Shoin (1987); *Enzyme Antibody Technique*, Revised Edition, Gakusai Kikaku (1985); and the like], for example, in the following manner.

A lectin recognizing the sugar chain structure of an antibody molecule constituting an antibody composition is labeled, and the labeled lectin is subjected to the reaction with a sample antibody composition, followed by measurement of the amount of a complex of the labeled lectin with the antibody molecule.

Examples of lectins useful for determining the sugar chain structure of an antibody molecule include WGA (wheat-germ agglutinin derived from *T. vulgaris*), ConA (concanavalin A derived from *C. ensiformis*), RIC (toxin derived from *R. communis*), L-PHA (leukoagglutinin derived from *P. vulgaris*), LCA (lentil agglutinin derived from *L. culinaris*), PSA (pea lectin derived from *P. sativum*), AAL (*Aleuria aurantia* lectin), ACL (*Amaranthus caudatus* lectin), BPL (*Bauhinia purpurea* lectin), DSL (*Datura stramonium* lectin), DBA (*Dolichos biflorus* agglutinin), EBL (Elderberry balk lectin), ECL (*Erythrina cristagalli* lectin), EEL (*Euonymus europaeus* lectin), GNL (*Galanthus nivalis* lectin), GSL (*Griffonia simplicifolia* lectin), HPA (*Helix pomatia* agglutinin), HHL (*Hippeastrum hybrid* lectin), Jacalin, LTL (*Lotus tetragonolobus* lectin), LEL (*Lycopersicon esculentum* lectin), MAL (*Maackia amurensis* lectin), MPL (*Madura pomifera* lectin), NPL (*Narcissus pseudonarcissus* lectin), PNA (peanut agglutinin), E-PHA (*Phaseolus vulgaris* erythroagglutinin), PTL (*Psophocarpus tetragonolobus* lectin), RCA (*Ricinus communis* agglutinin), STL (*Solanum tuberosum* lectin), SJA (*Sophora japonica* agglutinin), SBA (soybean agglutinin), UEA (*Ulex europaeus* agglutinin), VVL (*Vicia villosa* lectin) and WFA (*Wisteria floribunda* agglutinin).

The use of a lectin which specifically recognizes a core fucose is preferable. Examples of such lectins include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

6. Use of the Recombinant Antibody Composition of the Present Invention

Since the antibody variant composition of the present invention is a composition comprising single antibody variant molecules in which sugar chains which binds to Asn other than at position 297 are decreased or deleted, the antibody variant composition of the present invention is very useful for production of protein pharmaceutical which is required to produce single antibody molecules.

Also, among the antibody compositions of the present invention, since the antibody variant composition comprising an Fc variant in which Asn at position 392 is substituted with Lys in the Fc region comprising the amino acid sequence of SEQ ID NO:1 wherein the ratio of sugar chains with no core fucose among the total sugar chains in the composition is 20% or more is a composition comprising single antibody variant molecules in which sugar chains bound to Asn at position other than position 297 in Fc region are decreased or deleted and has higher ADCC activity, it has more excellent property in therapeutic effects than conventional antibody compositions.

In addition, among the antibody compositions of the present invention, since the antibody variant composition comprising an Fc variant in which Asn at position 392 is substituted with Lys in the Fc region comprising the amino acid sequence of SEQ ID NO:1 wherein the ratio of sugar chains with no core fucose among the total sugar chains in the composition is 20% or more is a composition comprising single antibody variant molecules in which sugar chains bound to Asn at position other than position 297 in Fc region are decreased or deleted and has higher CDC activity than human IgG1 antibody and human IgG3 antibody and has higher ADCC activity, it has more excellent property in therapeutic effects than conventional antibody compositions.

Furthermore, since the antibody variant composition comprising an antibody comprising a Fc variant in which Asn at position 392 is substituted with Lys in the Fc region comprising the amino acid sequence of SEQ ID NO:1 wherein the ratio of sugar chains without a core fucose is 100% is a composition comprises single antibody variant molecules in which sugar chains bound to Asn at position other than position 297 in the Fc region are decreased or deleted, has higher CDC activity than human IgG1 and human IgG3 and has the highest ADCC activity, the above antibody can be expected to have high clinical effects.

A medicament comprising the antibody variant composition of the present invention may be administered alone as a therapeutic agent. However, it is preferably mixed with one or more pharmaceutically acceptable carriers and provided as a pharmaceutical preparation produced by an arbitrary method well known in the technical field of pharmaceutics.

It is desirable to administer the medicament by the route that is most effective for the treatment. Suitable administration routes include oral administration and parenteral administration such as intraoral administration, intratracheal administration, intrarectal administration, subcutaneous administration, intramuscular administration and intravenous administration. In the case of an antibody preparation, intravenous administration is preferable.

The medicament may be in the form of spray, capsules, tablets, granules, syrup, emulsion, suppository, injection, ointment, tape, and the like.

The preparations suitable for oral administration include emulsions, syrups, capsules, tablets, powders and granules.

Liquid preparations such as emulsions and syrups can be prepared using, as additives, water, sugars (e.g., sucrose, sorbitol and fructose), glycols (e.g., polyethylene glycol and propylene glycol), oils (e.g., sesame oil, olive oil and soybean oil), antiseptics (e.g., p-hydroxybenzoates), flavors (e.g., strawberry flavor and peppermint), and the like.

Capsules, tablets, powders, granules, and the like can be prepared using, as additives, excipients (e.g., lactose, glucose, sucrose and mannitol), disintegrating agents (e.g., starch and sodium alginate), lubricants (e.g., magnesium stearate and talc), binders (e.g., polyvinyl alcohol, hydroxypropyl cellulose and gelatin), surfactants (e.g., fatty acid esters), plasticizers (e.g., glycerin), and the like.

The pharmaceutical preparations suitable for parenteral administration include injections, suppositories and sprays. Injections can be prepared using carriers comprising a salt solution, a glucose solution, or a mixture thereof, and the like. It is also possible to prepare powder injections by freeze-drying the antibody composition according to a conventional method and adding sodium chloride thereto.

Suppositories can be prepared using carriers such as cacao butter, hydrogenated fat and carboxylic acid.

The antibody composition may be administered as such in the form of spray, or sprays may be prepared using carriers which do not stimulate the oral or airway mucous membrane of a recipient and which can disperse the antibody composition as fine particles to facilitate absorption thereof.

Suitable carriers include lactose, glycerin and the like. It is also possible to prepare aerosols, dry powders, and the like according to the properties of the antibody composition and the carriers used. In preparing these parenteral preparations, the above-mentioned additives for the oral preparations may also be added.

The dose and administration frequency will vary depending on the desired therapeutic effect, the administration route, the period of treatment, the patient's age, body weight, and the like. However, an appropriate dose of the active ingredient for an adult person is generally 10 μg/kg to 20 mg/kg per day.

Furthermore, the anti-tumor effect of the antibody composition against various tumor cells can be examined by in vitro tests such as CDC activity measurement and ADCC activity measurement. In addition, examples of in vivo tests include anti-tumor experiments using tumor systems in an experimental animal such as mouse.

The CDC activity and ADCC activity measurements and anti-tumor experiments can be carried out according to the methods described in the document [*Cancer Immunology Immunotherapy*, 36, 373 (1993); *Cancer Research*, 54, 1511 (1994); and the like].

EXAMPLES

The following describes the invention based on examples, but the invention is not limited thereto.

In addition, in the following examples, each amino acid residue is shown by the three letter code or single letter code, N392K represents the antibody variant in which the amino acid substitution of Asn (N) at position 392 according to the EU index to Lys (K) was carried out.

Example 1

Sugar Chain Analysis of High CDC Activity Antibodies

In the human antibody Fc region, it is known that the sugar chain bind to Asn of the Asn-X-Ser/Thr (X is amino acid residues other than Pro) sequence at positions 297 to 299 according to the EU index, but it is not known that sugar chains bind to an N-glycoside-linked sugar chain consensus sequence at positions other than positions 297 to 299.

Each of the antibodies 1133, 113D, 113E, 113F, 113G and 113H having a high CDC activity type CH sequence described in WO2007/011041 is an antibody in which entire or partial domains of the human IgG1 Fc region and human IgG3 Fc region are replaced, and since the position 392 according to the EU index in the CH3 domain is Asn, the N-glycoside-linked sugar chain consensus sequence Asn-X-Ser/Thr is present.

In addition, the natural human IgG3 antibody also has the same N-glycoside-linked sugar chain consensus sequence Asn-X-Ser/Thr. Accordingly, in order to examine whether or not a sugar chain is bound to the Asn392 of the human IgG3 antibody and the IgG1/IgG3 domain swapped antibody described in WO2007/011041, sugar chain analysis of these antibodies was carried out.

As the IgG1/IgG3 domain swapped antibody, the 113F type anti-GM2 antibody GM2-113F described in WO2008/090960 was used. As schematically shown in FIG. 2(a) to (c), the structure of the 113F antibody is an antibody having a structure in which the amino acid sequence at positions 118 to 230 in the CH comprise a human IgG1 antibody-derived amino acid sequence, and the amino acid sequence at positions 231 to 422 comprises a human IgG3 antibody-derived amino acid sequence and the amino acid sequence at positions 423 to 447 comprises a human IgG1 antibody-derived amino acid sequence (SEQ ID NO:2).

As the human IgG3 type antibody, KM3523 in which the CH of an IgG1/K type anti-CD20 chimeric antibody Rituximab (U.S. Pat. No. 5,736,137) was modified so as to be a human IgG3 type (*Journal of Immunological Methods*, 2005, 306: 151-60) and the naturally existing human IgG3 antibody purified from IVIG (intravenous immunoglobulins) preparation were used.

Firstly, SDS-PAGE of GM2-113F and KM3523 was carried out under reducing conditions using 8% gel (Novex). The results are shown in FIG. 3.

As shown in FIG. 3, a minor band (band A) was detected at just over the band of H chain of GM2-113F (band B). Also, when the molecular weight of the GM2-113F was measured using liquid chromatograph mass spectrometer (LC-MS), a component having about 1380 Da larger molecular weight was detected in addition to the molecular weight corresponding to GM2-113F (about 148 kDa).

On the other hand, the band of H chain of KM3523 and naturally existing a human IgG3 antibody showed single molecular weight.

Since Asn392 and Thr394 are N-glycoside-linked sugar chain consensus sequences as described above, a possibility that a high mannose type N type sugar chain ($Man_6GlcNAc_2$, molecular weight 1378.48, hereinafter referred to as Man6 type sugar chain) is bound to the Asn392 of 113F type antibody was suggested, a detailed analysis was carried out in the following.

GM2-113F and KM3523 were dissolved in 0.1 mol/l Tris-HCl (pH 8.0) buffer containing 6 mol/l guanidine hydrochloride, dithiothreitol (manufactured by nacalai tesque) was added thereto to give a final concentration of 1.8 mg/ml, and the reduction reaction was carried out at 56° C. for 1 hour. Iodoacetamide (manufactured by nacalai tesque) was added to the solution after the reaction to give a final concentration of 11 mg/ml and alkylation reaction was carried out at 37° C. for 1 hour under shade.

Next, the reaction liquid was replaced with a buffer for enzyme digestion (1 mol/l of urea, 0.1 mol/l of $NH_4HCO_3$) using an ultrafiltration membrane, an Asp-N solution (sequencing grade, manufactured by Roche) was further added (E/S=1/50), followed by digestion at 37° C. for 16 hours, and the reaction was stopped by adding an appropriate amount of 1 mol/l HCl.

The peptide fragments obtained by the Asp-N digestion were analyzed using LC-MS. That is, the peptide fragment mixture was separated by a linear density gradient of mobile phase A (0.1% TFA) to mobile phase B (0.1% TFA, 90% $CH_3CN$), using a reverse HPLC (used column: YMC Pro C18, 1 mm i/d.×250 mm, manufactured by YMC, flow rate 60 µl/min).

The eluates were examined using a mass spectrometer (LTQ Orbitrap, manufactured by Thermo Scientific) by electrospraying, and the molecular weight of each peptide fragment was measured.

The obtained data were analyzed using a software (Xcalibur Qual Browser) attached to the mass spectrometer, and peaks of a molecular ion (m/z=1296.58, z=2) of a peptide fragment containing Asn392 (sequence DIAVEWESS-GQPFNNYNTTPPML) and a molecular ion (m/z=1985.81, z=2) in which a molecular weight (m/z=689.24, z=2) corresponding to the Man6 type sugar chain was bound to the peptide fragment were extracted and their signal intensities were numerically expresses as values. The results are shown in Table 1.

Table 1 shows a result of LC-MS analysis of Asn392-containing peptide fragments, obtained by the peptide mapping of GM2-113F and KM3523. Each numerical value in Table 1 shows signal intensity by the mass spectrometer. N.D. indicates that a signal was not detected.

TABLE 1

The results of LC-MS analysis of Asn-containing peptide fragments of GM-2-113F and KM3523

| | Signal intensity of peptide to which no N-glycoside type sugar chain is bound | Signal intensity of peptide to which Man6 type sugar chain is bound |
|---|---|---|
| GM2-113F | $2.42 \times 10^6$ | $1.16 \times 10^5$ |
| KM3523 | $3.03 \times 10^6$ | N.D. |

As shown in Table 1, a molecular ion to which the Man6 type sugar chain was added was detected in GM2-113F. On the other hand, the sugar chain addition signal was not detected in KM3523. Based on this, it was considered that modification of sugar chain to Asn392 is a phenomenon specific to GM2-113F.

Assuming that one molecule of the Man6 type sugar chain is linked to one antibody molecule based on the results of LC-MS measurement of GM2-113F, it was considered from the results shown in Table 1 that the Man6 type sugar chain-linked antibody is about 10% of the entire antibody composition.

Based on the above, it was revealed that in spite of each antibody having the same N-glycoside-linked sugar chain consensus sequence, each the N-glycoside type sugar chain was not bound to the Asn392 of H chain constant region of human IgG3 antibody, but on the other hand, the Man6 type sugar chain was bound to Asn at position 392 of the 113F type antibody at a constant ratio.

Example 2

Designing and Preparation of Antibody Variants

1. Designing of Variant Sequences

In order to avoid the sugar chain bound to Asn392 of 113F type H chain constant region as shown in Example 1, 46 kinds of amino acid substituted antibody variants were made as deleting the N-glycoside-linked sugar chain consensus sequence by substituting of Asn392, Thr393 and/or Thr394 by other amino acids (Table 2 and Table 3 below).

Also, in some antibody variants, influences upon biological activities of the antibody variants were verified by modifying human IgG3 antibody-specific amino acid residues, positions 276, 339 and 397 of Fc region of the 113F type.

FIG. 4 is alignment of amino acid sequences of H chain constant regions of human IgG1 antibody, human IgG3 antibody and 113F type antibody, and shows 6 amino acid sequences of 113F type Fc regions which was modified in this study.

Among these, four residues of Lys276, Thr339, Asn392 and Met397 are the amino acid residues different between human IgG1 antibody and human IgG3 antibody.

In this connection, a human κ type sequence was used as the DNA sequence of the CL, and a sequence identical to the anti-human CD20 antibody Rituximab (U.S. Pat. No. 5,736,137) was used as the DNA sequence of the V region.

2. Preparation of Antibody Variants (1) Construction of Expression Vector

An outline of the expression vector construction is shown in FIG. 5.

PrimeSTAR Mutagenesis Basal Kit (Takara Shuzo Co. Led.) was used in the introduction of site directed mutagenesis into a DNA encoding the CH of antibody variants described in the following. As the primers, sequences for introducing substitution of various amino acid residues into the CH region (Table 1) were designed and synthesized in accordance with the instructions attached to the kit (manufactured by Invitrogen).

The pKTX93/113F vector described in WO2007/011041 was used as the template. By carrying out PCR using these primers and template, a vector having desired mutation in the H chain constant region gene sequence was obtained.

The amino acid sequence of an antibody having two amino acid substitutions, in which the amino acid substitution of N392K was combined with one amino acid residue substitution selected from 276, 339, 393 and 397 was obtained by using the antibody variant expression vector having an N392K mutation (pKTX93/113F—N392K) as the template by the above-mentioned procedure and carrying out the same operation.

The nucleotide sequence of the H chain constant region comprising the mutation of interest was transferred to pKTX93/113F using ApaI and NruI (manufactured by New England Biolabs).

(2) Preparation of Antibody-Producing Cell

The cells were cultured at 37° C. in a 5% $CO_2$ incubator. In order to obtain a high ADCC type de-fucosylation antibody, a CHO/DG44 cell in which α1,6-fucosyltransferase was knocked out (hereinafter referred to as FUT8KO cell) (U.S. Pat. No. 6,946,292) was used.

Into $1.6 \times 10^6$ cells of the FUT8KO cell, 4 μg of the expression vector was introduced by the electroporation method [*Cytotechnology*, 3, 133 (1990)], followed by culturing using IMDM-(10) [IMDM medium (GIBCO) containing 10% dialyzed bovine serum (dFBS)]. Two days after the culturing, the medium was replaced with IMDM-(10) comprising G418 sulfate (manufactured by nacalai tesque) at a concentration of 0.5 mg/ml [hereinafter referred to as IMDM-(10G)], the cell was continued to culture and a resulting cell was recognized as a G418 resistant cell.

(3) Expression and Purification of Antibodies

Purified 113F type antibody and the purified antibody variants shown in Table 2 and were obtained by the following method. After the G418 resistant cells obtained in the above paragraph were suspended in IMDM-(10G) to give a density of $3 \times 10^5$ cells/ml and cultured for 3 days, the medium with Ex-cell 302 (SAFC Biosciences) and the cells were cultured for 7 to 11 days, followed by recovering the culture supernatant.

The culture supernatant obtained in the above paragraph was passed through a column filled with 0.5 ml of MabSelect SuRe (GE Healthcare) carrier at a flow rate of 0.5 ml/min to 1.0 ml/min. After washing by adding 3 ml of a borate buffer (0.2 M sodium borate and 150 mM sodium chloride) and 0.25 ml of 0.1M sodium citrate solution (pH 3.6) in order, the fraction eluted with 1.5 ml of 0.1M sodium citrate solution (pH 3.6) was recovered as a crude elution fraction.

Through a column filled with 10 ml of Econo-Pac 10DG (BIO RAT)), 1.5 ml of the crude elution fraction was passed. After washing with 1.5 ml of a citrate buffer (150 mM sodium chloride and 10 mM sodium citrate, adjusted to pH 6.0 with sodium hydroxide), the fraction eluted with 3.0 ml of the same citrate buffer was recovered as an antibody solution.

(4) SDS-PAGE Analysis of Antibody Variants

Among the antibody variants shown in Table 2 and Table 3, SDS-PAGE analysis of the purified antibodies other than N392K/K276S was carried out by the following method. Each antibody solution prepared into 0.1 mg/ml with a sample buffer containing 0 mM (non-reducing conditions) or 10 mM (reducing conditions) of dithiothreitol [0.3 M of Tris-HCl (pH 6.8), 10% of sodium dodecyl sulfate and 50% of glycerol] and treated at 100° C. for 5 minutes was applied to polyacrylamide gel (Atto Corp.) at a volume of 10 μl per lane portion and subjected to electrophoresis at 20 mA per 1 plate of the gel for 2 hours. The gel was recovered and then stained using CBB stain one (nacalai tesque) in accordance with the instructions attached to the manufacture article.

By the SDS-PAGE of samples under non-reducing conditions, band patterns similar to that of the 113F type antibody were found in all antibody variants, thus showing that there are no problems in purity of purified products. As a result of SDS-PAGE of the reduction-treated samples, a minor band was found at the high molecular weight side of that of the H chain in 113F lane. However, the same band was disappeared in the lane of the antibody variant, it was found that the sugar chain bound to the Asn residue at position 392 was removed from the prepared antibody variants.

Example 3

Activity Evaluation of Antibody Variants

1. Measurement of CDC Activity

CDC activity of antibody variants was measured using a transformed cell, KC1156 prepared by introducing human CD20 gene into a mouse thymoma cell line EL4 [*Clin. Cancer Res.*, 11, 2327 (2005)] and CD20-positive tumor cell, Daudi cell (JCRB), Raji (JCRB), ST486 (ATCC), EHEB (DSMZ) and MEC-1 (DSMZ) as the target cell.

An anti-CD20 antibody Rituximab (U.S. Pat. No. 5,736,137) was used as the control of antibodies comprising an IgG1 type H chain constant region. Each target cell was diluted to give a density of $1.0 \times 10^6$ cells/ml using RPMI 1640 (Wako Pure Chemical Industries, Ltd.) containing 10% FBS (JRH), 50 μl of each diluted cell, 50 μl of antibody solution adjusted 3-fold of the final concentration and 50 μl of a human complement (SIGMA) diluted 2-fold or 8-fold in the case of EL4/CD20-A were dispensed, respectively, into each of wells of a 96-well flat bottom plate (Sumitomo Bakelite Co., Ltd.).

In addition, a well which does not contain antibody was prepared as a 0% reaction well, and a well which does not contain target cell was prepared as a 100% reaction well. After culturing at 37° C. (5% $CO_2$) for 2 hours, WST-1 (ROCHE) was added in 15 µl to each of reaction wells and cultured at 37° C. (5% $CO_2$) for 3 hours. After completion of the reaction, OD450 of each well was measured and the cytotoxicity (%) was calculated using the following formula.

Cytotoxicity(%)=100×{1−(absorbance of reaction well−absorbance of 100% reaction well)/(absorbance of 0% reaction well−absorbance of 100% reaction well)}

In order to compare CDC activity of all antibody variants under the same conditions, CDC activity using KC1156 at an antibody concentration of 1 µg/ml was measured by all samples on the same plate, with the results shown in Table 2 and Table 3.

TABLE 2

| Antibody variant | Amino Acid Residue | | | | | | CDC activity* |
|---|---|---|---|---|---|---|---|
| | Lys276 | Thr339 | Asn392 | Thr393 | Thr394 | Met397 | |
| N392F | | | Phe | | | | + |
| N392L | | | Leu | | | | + |
| N392I | | | Ile | | | | + |
| N392M | | | Met | | | | + |
| N392V | | | Val | | | | + |
| N392P | | | Pro | | | | + |
| N392A | | | Ala | | | | + |
| N392Y | | | Tyr | | | | + |
| N392H | | | His | | | | + |
| N392Q | | | Gln | | | | + |
| N392K | | | Lys | | | | + |
| N392D | | | Asp | | | | + |
| N392E | | | Glu | | | | + |
| N392W | | | Trp | | | | + |
| N392R | | | Arg | | | | + |
| N392G | | | Gly | | | | + |
| T393P | | | | Pro | | | ++ |
| T394Y | | | | | Tyr | | ++ |
| T394L | | | | | Leu | | + |
| T394F | | | | | Phe | | ++ |
| T394D | | | | | Asp | | + |
| T394K | | | | | Lys | | + |
| T394N | | | | | Asn | | + |

*The case where the CDC activity of the antibody variant was equal to or higher than that of 113F type antibody was represented by "++" or "+", and the case where the CDC activity was lower than that of 113F type antibody was represented by "−".

TABLE 3

| Antibody variant | Amino Acid Residue | | | | | | CDC activity* |
|---|---|---|---|---|---|---|---|
| | Lys276 | Thr339 | Asn392 | Thr393 | Thr394 | Met397 | |
| N392K/T393A | | | Lys | Ala | | | + |
| N392K/K276F | Phe | | Lys | | | | − |
| N392K/K276S | Ser | | Lys | | | | − |
| N392K/T339N | | Asn | Lys | | | | − |
| N392K/T339Y | | Tyr | Lys | | | | ++ |
| N392K/M397F | | | Lys | | | Phe | + |
| N392K/M397L | | | Lys | | | Leu | − |
| N392K/M397I | | | Lys | | | Ile | − |
| N392K/M397V | | | Lys | | | Val | − |
| N392K/M397S | | | Lys | | | Ser | − |
| N392K/M397P | | | Lys | | | Pro | − |
| N392K/M397T | | | Lys | | | Thr | − |
| N392K/M397A | | | Lys | | | Ala | − |
| N392K/M397Y | | | Lys | | | Tyr | − |
| N392K/M397H | | | Lys | | | His | − |
| N392K/M397Q | | | Lys | | | Gln | + |
| N392K/M397K | | | Lys | | | Lys | − |
| N392K/M397D | | | Lys | | | Asp | + |
| N392K/M397E | | | Lys | | | Glu | − |
| N392K/M397W | | | Lys | | | Trp | − |
| N392K/M397R | | | Lys | | | Arg | − |
| N392K/M397G | | | Lys | | | Gly | − |
| N392K/M397N | | | Lys | | | Asn | + |

*The case where the CDC activity of the antibody variant was equal to or higher than that of 113F type antibody was represented by "++" or "+", and the case where the CDC activity was lower than that of 113F type antibody was represented by "−".

As shown in Table 2 and Table 3, the CDC activity of T393P, T394Y, T394F and N392K/T339Y was higher than that of the 113F before substitution. Also, substitutions at position 392 and 397 were exhaustively carried out, and it was found that antibody variants of Asn392 shows a CDC activity level of equal to or higher than that of 113F and some of the antibody variants of Met397 have a tendency of lowering the activity.

Measurement of the CDC activity for the CD20 transfectant KC1156 was carried out further in detail on N392K, T394Y and T394F. The results are shown in FIGS. 6(a) and (b).

As shown in FIG. 6, CDC activity of N392K was equivalent to that of the 113F type antibody before substitution. In addition, significant increase in the CDC activity was found in T394Y and T394F in comparison with 113F type antibody.

The CDC activity of N392K, T394Y, T394F and N392K/T339Y for the CD20-positive tumor cells was measured, with the results shown in FIG. 7(a) to (e).

As shown in FIG. 7(a) to (e), similar to the CDC activity for CD20-positive tumor cells, N392K exhibited the CDC activity level equivalent to that of the 113F type antibody, and increase in the CDC activity was found in T394Y, T394F and N392K/T339Y as compared with the 113F type antibody substitution.

2. Complement Binding Activity

Binding activity of a first complement component C1q with antibody variants was measured using a flow cytometer. As comparative controls, the 113F type antibody and an IgG1 type antibody Rituximab were used. With RPMI 1640 (GIBCO), 50 µA of Daudi cell diluted to $1.5 \times 10^7$ cells/ml and 50 µl of each antibody solution adjusted 3-fold of the final concentration were dispensed into each of wells of a 96-well U bottom plate (FALCON) and allowed to stand still at 37° C. (5% $CO_2$) for 10 minutes, and then human serum (SIGMA) diluted to 6% was added at a volume of 50 to each of wells and allowed to stand still at 37° C. (5% $CO_2$) for 15 minutes.

After washing twice with PBS, an FITC-labeled antihuman C1q antibody (Dako Cytomation) diluted 100 times with a buffer for FACS [1% BSA, 0.02% ethylenediaminetetraacetic acid and 0.05% sodium azide, dissolved in PBS] was added at 50 µl to respective wells and allowed to react at 4° C. for 30 minutes under shade.

The cells were washed twice with 200 µl of the buffer for FACS and suspended in 200 µl of the buffer for FACS, and the fluorescence intensity was measured using Cytomics FC 500 MPL (Beckman Coulter).

Figure 8:
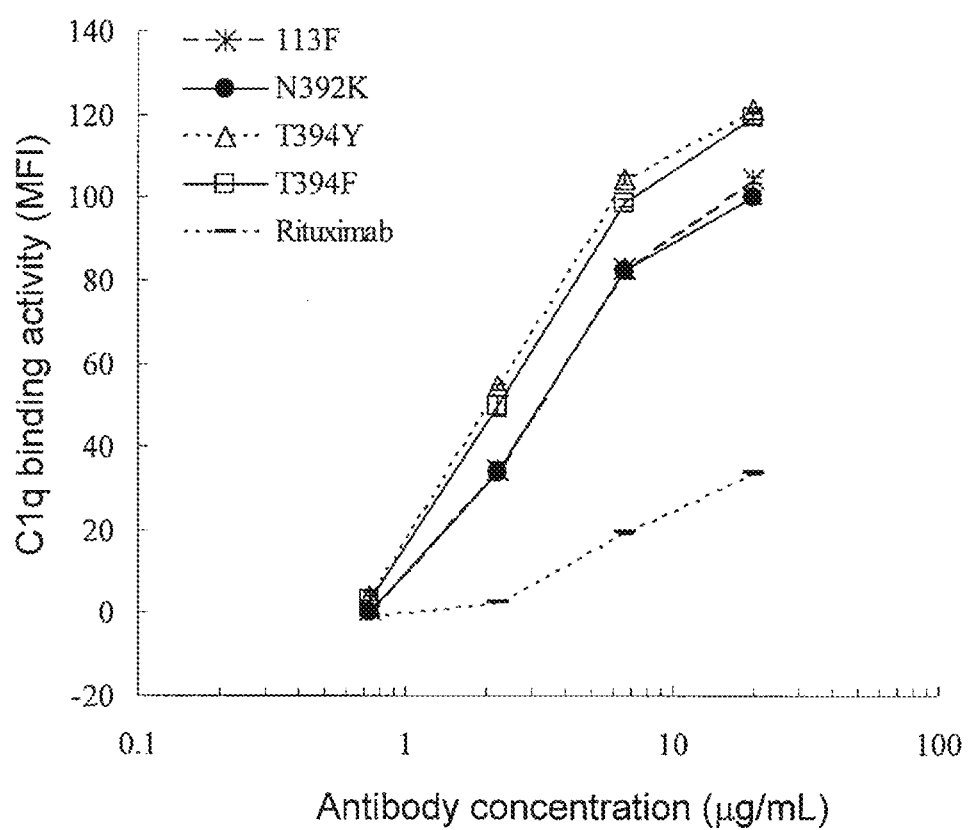
FIG. 8 shows a measurement result of C1q binding activity of the 113F antibody, N392K, T394Y and T394F, using a flow cytometer. A CD20-positive tumor cell Daudi was used in the test, and after each antibody was allowed to react with human serum, binding of C1q was detected by FITC labeled anti-human C1q antibody. In the graph, the ordinate represents mean fluorescence intensity (MFI) and the abscissa represents antibody concentration. The test was carried out by N=3.

In this connection, 50% effective concentration ($EC_{50}$) of the reaction was calculated by fixing the minimum value to 0 based on the administration reaction logistic (dosersplgst) of KaleidaGraph (HULINKS, Inc.). The results are shown in FIG. 8.

Also, the values of $EC_{50}$ calculated from the graph are shown in Table 4. The Ymax in Table 4 represents maximum value of approximate curve.

TABLE 4

| Antibody variant | C1q binding activity | |
|---|---|---|
| | $EC_{50}$ (µg/mL) | Ymax (MFI) |
| 113F | 3.39 | 106.6 |
| N392K | 3.19 | 101.3 |
| T394Y | 2.52 | 120.7 |
| T394F | 2.77 | 119.6 |
| Rituximab | 6.16 | 35.3 |

As shown in FIG. 8 and Table 4, C1q binding activity of N392K was equivalent to that of 113F. By this analysis, C1q binding activity of T394F and T394Y was further increased than that of the 113F type antibody before substitution.

3. ADCC Activity

ADCC activity of the antibody variants prepared in the above-mentioned Example 2 was measured by the method described in described in WO2007/011041. Since all of the prepared antibody variants were high ADCC type antibodies having no core fucose, Rituximab was used as the negative control.

The CD20-positive tumor cells Daudi, Raji and ST486 were used as the target cells, and PBMC prepared from a healthy donor was used as the effector cell.

The test was carried out at a ratio of effector cell to target cell of 1:20, 1:25 or 1:30, and the cytotoxicity (%) was calculated by the following formula.

$$\text{Cytotoxicity}(\%) = 100 \times (S-Ab)/(\text{Max}-T)$$

S=absorbance of sample reaction well−absorbance of medium well
Ab=absorbance of antibody no addition well−medium well absorbance
T=absorbance of target well−absorbance of medium well
Max=absorbance of 100% reaction well−absorbance of 100% reaction control well As a result, the ADCC activity of N392K, T394F and T394Y was equivalent to that of the 113F type antibody and significantly increased as compared with Rituximab.

4. Preparation of FcRn and $\beta_2$-Microglobulin Protein

In order to prepare a protein having histidine tag (an amino acid sequence in which 6 His residues are continued) on the C-terminus of a soluble human fetal Fc receptor (FcRn), a cDNA encoding a protein having histidine tag on the C-terminus of the cell membrane domain of FcRn a chain was amplified by carrying out PCR using a primer FcRn fw (SEQ ID NO:4) and a primer FcRn rv (SEQ ID NO:5) and using a human placenta-derived cDNA library (manufactured by Clontech) as the template.

PCR was carried out based on the instructions attached to KOD polymerase (manufactured by Toyobo Co., Ltd.) thereby obtaining a plasmid pCRFcRnα comprising a cDNA encoding a protein containing histidine tag on the C-terminus of FcRnα.

On the other hand, construction of a cDNA encoding human $\beta_2$-microglobulin was carried out based on the following procedure. By preparing four synthetic DNAs covering the DNA sequence of human $\beta_2$-microglobulin, PCR was carried out in the same manner as described above to obtain a plasmid pCRB2M comprising a DNA encoding the cDNA of human $\beta_2$-microglobulin.

Next, the humanized antibody expression vector for animal cells, pKANTEX93, described in WO97/10354 was digested with restriction enzymes NotI and BamHI to recover a DNA fragment of about 11 Kbp in which a cDNA region encoding the heavy chain constant region of the human antibody was removed.

On the other hand, a DNA fragment of about 400 bp encoding human β₂-microglobulin was obtained by digesting the pCRB2M with restriction enzymes NotI and BamHI. These DNA fragment of about 11 Kbp and DNA fragment of about 400 bp were ligated using Ligation High (manufactured by Toyobo Co., Ltd.) and the obtained DNA was introduced into *Escherichia coli* DH5a (manufactured by Toyobo Co., Ltd.), thereby constructing a plasmid pKANTEXB2M.

Next, the pKANTEXB2M was digested with restriction enzymes EcoRI and DraIII to recover a plasmid fragment of about 11 Kbp in which a cDNA encoding the light chain constant region of the human antibody was removed. On the other hand, a cDNA encoding an FcRnα chain of about 0.9 Kbp which is obtained by digesting the plasmid pCRFcRnα with EcoRI and DraIII was recovered.

The above-mentioned DNA fragment of about 11 Kbp and DNA fragment of about 0.9 Kbp were ligated using Ligation High and then the obtained DNA was introduced into the *E. coli* DH5a, thereby obtaining a plasmid pKANTEXFcRn-His.

The thus obtained plasmid was converted into a linear chain by digesting with a restriction enzyme AatII (manufactured by New England BioLab), and then used for introduction into a cell. After the digestion, the reaction liquid was subjected to agarose gel electrophoresis to confirm that the plasmid is accurately converted into a linear chain.

A cell in which FcRn and β-microglobulin were co-expressed was prepared in the same manner as described above and cultured. After the culturing, the culture supernatant was recovered, and purification of the soluble type FcRn was carried out using a Ni-NTA agarose (manufactured by QIAGEN) column in accordance with the instructions attached thereto to obtain a complex protein of the soluble FcRn protein and β-microglobulin.

The thus obtained complex protein of soluble FcRn protein and β₂-microglobulin was used as a soluble FcRn.

5. FcRn Binding Activity

It is known that blood half-life of an antibody is related to its binding activity to neonatal Fc receptor (FcRn) existing in endosome at pH 6.0 and pH 7.4 [*J. Immunol.*, 176, 346 (2006)].

In order to examine influence of amino acid substitutions into the antibody variants upon blood half life, FcRn binding activity of antibody variants at pH 6.0 or pH 7.4 was evaluated by Biacore T-100 (GE Healthcare).

Rituximab and Rituximab comprising an IgG1 variant sequence (T250Q/M428L) [*J. Immunol.*, 176, 346 (2006)] and having increased binding activity to FcRn disclosed in known references were used as the controls.

Anti-β₂-microgloblin antibody (manufactured by Abeam) diluted to 10 μg/ml with Acetate 5.5 was allowed to react at a flow rate of 10 μl/min for 420 seconds and fixed to a CM5 sensor chip (GE Healthcare) by the amine coupling method (target amount: 10,000 RU).

Also, using HBS-EP+ Buffer (GE Healthcare) adjusted to pH 6.0 or pH 7.4, 1 μg/ml of soluble FcRn was allowed to react at a flow rate of 5 μl/min for 24 seconds to capture at the sensor chip surface (target amount: 100 RU).

Each antibody was diluted with HBS-EP+ Buffer of pH 6.0 or pH 7.4 and allowed to react at a flow rate of 30 μl/min for 120 seconds, and the association dissociation reaction was measured. The sensor chip was regenerated by reacting with Glycine-HCl pH 2.0 at a flow rate of 60 μl/min for 60 seconds.

The $K_D$ value was calculated by the analysis with a T-100 Evaluation software (GE Healthcare) using the Bivalent binding model.

Various reaction constants of the antibody variants at pH 6.0 are shown in Table 5.

TABLE 5

|  | ka1 (×10⁵ 1/Ms) | kd1 (1/s) | $K_D$ (×10⁻⁸ M) |
|---|---|---|---|
| Assay 1 |  |  |  |
| T250Q/M428L | 5.23 | 0.021 | 3.99 |
| Rituximab | 3.25 | 0.127 | 38.9 |
| N392K | 4.71 | 0.166 | 35.2 |
| T394Y | 2.83 | 0.124 | 43.9 |
| T394F | 3.18 | 0.132 | 41.3 |
| Assay 2 |  |  |  |
| T250Q/M428L | 3.68 | 0.034 | 9.98 |
| Rituximab | 3.96 | 0.236 | 59.6 |
| 113F | 2.44 | 0.143 | 58.5 |
| N392K | 3.26 | 0.146 | 44.8 |

As shown in Table 5, the dissociation constant $K_D$ of N392K, T394Y and T394F at pH 6.0 was equivalent to that of 113F type antibody and Rituximab. In addition, the binding activity was not found at pH 7.4 in any one of the antibodies.

While the invention has been described in detail and with reference to specific embodiments thereof, it will be apparent to one skill in the art that various changes and substitutions can be made therein without departing from the spirit and scope thereof.

This application is based on U.S. provisional application No. 61/309,631, filed on Mar. 2, 2010, the entire contents of which are incorporated hereinto by reference. All references cited herein are incorporated in their entirety.

[Free Text of Sequence Listing]
SEQ NO:1: Amino acid sequence of Fc region of 113F
SEQ NO:2: Amino acid sequence of constant region of 113F
SEQ NO:3: Amino acid sequence of constant region of N392K
SEQ NO:4: Nucleotide sequence of fw primer of FcRn
SEQ NO:5: Nucleotide sequence of rv primer of FcRn

What is claimed is:

1. A composition comprising antibodies having an Fc region, wherein said Fc region comprises the amino acid sequence of SEQ ID NO: 1 but with one or more amino acid substitutions selected from the group consisting of:
    substitution of position 162 in SEQ ID NO: 1 with a residue other than Asn;
    substitution of position 163 in SEQ ID NO: 1 with a Pro or Ala residue;
    substitution of position 164 in SEQ ID NO: 1 with a residue other than Ser;
    substitution of position 109 in SEQ ID NO: 1 with a Tyr residue; and
    substitution of position 167 in SEQ ID NO: 1 with a Gln, Asn, Asp or Phe residue.

2. The composition according to claim 1, wherein said Fc region comprises the amino acid sequence of SEQ ID NO: 1 but with one or more amino acid substitutions selected from the group consisting of:
    substitution of position 162 in SEQ ID NO: 1 with a Gly, Ala, Val, Leu, Ile, Met, Pro, Asp, Gln, Glu, Lys, Arg, His, Phe, Tyr or Trp residue;
    substitution of position 163 in SEQ ID NO: 1 with a Pro residue; and
    substitution of position 164 in SEQ ID NO: 1 with a Leu, Asn, Asp, Lys, Phe, Tyr or Trp residue.

3. The composition according to claim 1, wherein said Fc region comprises the amino acid sequence of SEQ ID NO: 1 but with the following amino acid substitutions:
    (a) substitution of position 162 in SEQ ID NO: 1 with a residue other than Asn; and (b) one or more substitutions selected from the group consisting of:
- substitution of position 163 in SEQ ID NO: 1 with a Pro or Ala residue;
- substitution of position 164 in SEQ ID NO: 1 with a residue other than Ser;
- substitution of position 109 in SEQ ID NO: 1 with a Tyr residue; and
- substitution of position 167 in SEQ ID NO: 1 with a Gln, Asn, Asp or Phe residue.

4. The composition according to claim 1, wherein said antibodies comprise a CH1 domain and a hinge domain, and wherein the sequences of the CH1 domain and hinge domain of said antibodies are the same as the sequences of the CH1 domain and hinge domain of human IgG1, respectively.

* * * * *

SEQUENCE LISTING

<160> NUMBER OF SEQ ID NOS: 5

<210> SEQ ID NO 1
<211> LENGTH: 217
<212> TYPE: PRT
<213> ORGANISM: Artificial
<220> FEATURE:
<223> OTHER INFORMATION: Synthetic construction of 113F Fc region

<400> SEQUENCE: 1

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 2
<211> LENGTH: 330
<212> TYPE: PRT
<213> ORGANISM: Artificial
<220> FEATURE:
<223> OTHER INFORMATION: Synthetic construct of 113F constant region

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                    130                 135                 140
Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
                260                 265                 270

Asn Tyr Asn Thr Thr Pro Pro Met Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 330
<212> TYPE: PRT
<213> ORGANISM: Artificial
<220> FEATURE:
<223> OTHER INFORMATION: Synthetic construct of N392K constant region

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
```

```
                    165                 170                 175
Glu Gln Phe Asn Ser Thr Phe Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Thr Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
                260                 265                 270

Asn Tyr Lys Thr Thr Pro Pro Met Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 102
<212> TYPE: DNA
<213> ORGANISM: Artificial
<220> FEATURE:
<223> OTHER INFORMATION: FcRn fw primer

<400> SEQUENCE: 4
agtaaacctg aatctttgga gtacgctgga tagcctccag gccagaaaga gagagtagcg      60
cgagcacagc taaggccacg gagcgagaca tggtgagggg tc                       102

<210> SEQ ID NO 5
<211> LENGTH: 120
<212> TYPE: DNA
<213> ORGANISM: Artificial
<220> FEATURE:
<223> OTHER INFORMATION: FcRn rv primer

<400> SEQUENCE: 5
tccaaagatt caggtttact cacgtcatcc agcagagaat ggaaagtcaa atttcctgaa      60
ttgctatgtg tctgggtttc atccatccga cattgaagtt gacttactga agaatggaga    120
```